US012807951B2

(12) United States Patent
Nimjee et al.

(10) Patent No.: US 12,807,951 B2
(45) **Date of Patent: *Nov. 24, 2026**

(54) VON WILLEBRAND FACTOR (VWF)-TARGETING AGENTS AND METHODS OF USING THE SAME

(71) Applicants: Duke University, Durham, NC (US); Ohio State Innovation Foundation, Columbus, OH (US)

(72) Inventors: Shahid M. Nimjee, Columbus, OH (US); Bruce Sullenger, Durham, NC (US); George A. Pitoc, Durham, NC (US); Juliana Layzer, Durham, NC (US)

(73) Assignees: Duke University, Durham, NC (US); Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/622,413

(22) Filed: Mar. 29, 2024

(65) Prior Publication Data

US 2024/0318178 A1 Sep. 26, 2024

Related U.S. Application Data

(60) Continuation of application No. 17/146,147, filed on Jan. 11, 2021, now Pat. No. 11,965,160, which is a division of application No. 16/334,307, filed as application No. PCT/US2017/052063 on Sep. 18, 2017, now Pat. No. 10,889,816.

(60) Provisional application No. 62/395,642, filed on Sep. 16, 2016.

(51) Int. Cl.

| | |
|---|---|
| ***C07H 21/02*** | (2006.01) |
| ***A61K 31/7088*** | (2006.01) |
| ***A61K 31/7105*** | (2006.01) |
| ***A61K 31/7115*** | (2006.01) |
| ***A61K 45/06*** | (2006.01) |
| ***A61K 47/54*** | (2017.01) |
| ***A61K 47/60*** | (2017.01) |
| ***A61K 47/64*** | (2017.01) |
| ***A61P 7/02*** | (2006.01) |
| ***C07H 21/04*** | (2006.01) |
| ***C12N 15/113*** | (2010.01) |
| ***C12N 15/115*** | (2010.01) |

(52) U.S. Cl.

CPC ........ *C12N 15/113* (2013.01); *A61K 31/7088* (2013.01); *A61K 31/7105* (2013.01); *A61K 31/7115* (2013.01); *A61K 45/06* (2013.01); *A61K 47/554* (2017.08); *A61K 47/60* (2017.08); *A61K 47/64* (2017.08); *A61P 7/02* (2018.01); *C12N 15/115* (2013.01); *C12N 2310/113* (2013.01); *C12N 2310/16* (2013.01); *C12N 2310/317* (2013.01); *C12N 2310/3183* (2013.01); *C12N 2310/3515* (2013.01)

(58) Field of Classification Search

CPC ............................ C12N 15/113; C12N 15/115

See application file for complete search history.

(56) References Cited

U.S. PATENT DOCUMENTS

| | | | |
|---|---|---|---|
| 5,660,985 | A | 8/1997 | Pieken et al. |
| 5,756,291 | A | 5/1998 | Griffin et al. |
| 5,770,198 | A | 6/1998 | Coller et al. |
| 5,935,776 | A | 8/1999 | Green et al. |
| 5,958,691 | A | 9/1999 | Pieken et al. |
| 6,376,190 | B1 | 4/2002 | Gold et al. |
| 6,780,850 | B1 | 8/2004 | Dougan et al. |
| 6,855,496 | B2 | 2/2005 | Pagratis et al. |
| 7,300,922 | B2 | 11/2007 | Sullenger et al. |
| 7,304,041 | B2 | 12/2007 | Rusconi |
| 7,312,325 | B2 | 12/2007 | Sullenger et al. |
| 7,396,664 | B2 | 7/2008 | Daly et al. |
| 7,566,701 | B2 | 7/2009 | Diener et al. |
| 7,741,307 | B2 | 6/2010 | Sullenger et al. |
| 7,776,836 | B2 | 8/2010 | Sullenger et al. |
| 8,367,627 | B2 | 2/2013 | Sullenger et al. |
| 8,790,924 | B2 | 7/2014 | Sullenger et al. |
| 9,061,043 | B2 | 6/2015 | Sullenger et al. |
| 9,150,867 | B2 | 10/2015 | Maher, III |
| 9,687,529 | B2 | 6/2017 | Sullenger et al. |
| 9,873,727 | B2 | 1/2018 | Sullenger et al. |
| 9,958,448 | B2 | 5/2018 | Halbert |
| 10,350,158 | B2 | 7/2019 | Lee |
| 10,533,059 | B2 | 1/2020 | Sengupta et al. |
| 11,421,234 | B2 | 8/2022 | Ma et al. |

(Continued)

FOREIGN PATENT DOCUMENTS

| | | |
|---|---|---|
| AU | 2012244176 B8 * | 1/2016 |
| WO | 2002026932 | 4/2002 |

(Continued)

OTHER PUBLICATIONS

Oney et al. (Oligonucleotides, 17, 2007, 265-274).*

(Continued)

*Primary Examiner* — Amy Rose Hudson

(74) *Attorney, Agent, or Firm* — Quarles & Brady, LLP

(57) ABSTRACT

Provided herein are aptamers capable of inhibiting the activity of Von Willebrand Factor (VWF). Pharmaceutical compositions comprising these aptamers are also provided. Methods of preventing blood clot formation in a subject by administering the aptamers are provided and methods of treating a blood clot by administering a VWF-targeting agent are also provided.

20 Claims, 25 Drawing Sheets

Specification includes a Sequence Listing.

(56) References Cited

U.S. PATENT DOCUMENTS

| | | | |
|---|---|---|---|
| 2003/0083294 A1 | 5/2003 | Sullenger et al. |
| 2003/0143217 A1 | 7/2003 | Baird et al. |
| 2003/0153506 A1 | 8/2003 | Bylund et al. |
| 2003/0158120 A1 | 8/2003 | Mattsson |
| 2005/0176940 A1 | 8/2005 | King |
| 2006/0193821 A1 | 8/2006 | Diener et al. |
| 2006/0264369 A1 | 11/2006 | Diener et al. |
| 2008/0051339 A1 | 2/2008 | Sullenger et al. |
| 2008/0207546 A1 | 8/2008 | Sullenger |
| 2008/0220055 A1 | 9/2008 | Ludwig et al. |
| 2009/0048193 A1 | 2/2009 | Rusconi et al. |
| 2010/0003244 A1 | 1/2010 | Munch et al. |
| 2010/0076060 A1 | 3/2010 | Sullenger et al. |
| 2010/0184822 A1 | 7/2010 | Sullenger et al. |
| 2010/0249217 A1 | 9/2010 | Sullenger et al. |
| 2010/0297654 A1 | 11/2010 | Heyduk |
| 2010/0311820 A1 | 12/2010 | Layzer et al. |
| 2010/0324120 A1 | 12/2010 | Chen et al. |
| 2011/0118187 A1 | 5/2011 | Sullenger et al. |
| 2011/0160443 A1 | 6/2011 | Sullenger et al. |
| 2012/0183564 A1 | 7/2012 | Sullenger et al. |
| 2012/0264815 A1 | 10/2012 | Sullenger et al. |
| 2014/0050717 A1 | 2/2014 | Dockal et al. |
| 2014/0348755 A1 | 11/2014 | Weng |
| 2015/0307883 A1 | 10/2015 | Yarden |
| 2016/0130585 A1 | 5/2016 | Casella et al. |
| 2018/0117182 A1 | 5/2018 | Sullenger et al. |
| 2020/0095636 A1 | 3/2020 | Sullenger et al. |
| 2020/0353102 A1 | 11/2020 | Sullenger et al. |

FOREIGN PATENT DOCUMENTS

| | | | |
|---|---|---|---|
| WO | 2006/033854 | 3/2006 | |
| WO | 2006/067173 | 6/2006 | |
| WO | 2007/035532 | 3/2007 | |
| WO | 2008/066621 | 6/2008 | |
| WO | WO-2008150495 A2 * | 12/2008 | .......... C12N 15/115 |
| WO | 2014/169049 | 10/2014 | |
| WO | 2018053427 | 3/2018 | |
| WO | 2018175918 | 9/2018 | |
| WO | 2020086996 | 4/2020 | |

OTHER PUBLICATIONS

Kandimalla et al. (Nucleic Acids Research, 1995, 23, 17, 3578-3584).*

Collet et al. (Circulation Research, vol. 90, Issue 4, Mar. 8, 2002; pp. 428-434).*

Office Action for U.S. Appl. No. 12/311,943 mailed May 10, 2012.

Office Action for U.S. Appl. No. 13/296,045 mailed dated Oct. 22, 2013.

Office Action for U.S. Appl. No. 14/115,797 mailed Sep. 17, 2015.

Oney, et al., "Antidote-controlled platelet inhibition targeting von Willebrand factor with aptamers," (2007) Oligonucleotides 17(3):265-274—Abstract.

Oney, S. et al., "Development of universal antidotes to control aptamer activity," (2009) Nature Medicine, 15 (10): 1224-1229.

Orset et al., "Mouse model of in situ thromboembolic stroke and reperfusion," (2007) Stroke 38:2771-8.

Que-Gewirth, N.S. et al., "Gene therapy progress and prospects: RNA aptamers," (2007) Gene Therapy 14 (4):283-291.

Quinn et al, "A guide for diagnosis of patients with arterial and venous thrombosis," (2000) J. Clin. Lab. Sci. 13 (4):229-238.

Reikvam, H. et al. "Thrombelastography," (2009) Transfus Apher Sci; 40: 119-23.

Restriction Requirement dated Jan. 8, 2019 for U.S. Appl. No. 15/570,065.

Restriction Requirement dated Jun. 7, 2019 for U.S. Appl. No. 16/334,307.

Ruggeri, Z.M. et al., "Contribution of Distinct Adhesive Interactions to Platelet Aggregation in Flowing Blood" (1999) Blood 94:172-178.

Ruggeri, Z.M. et al. (2003) Current Opinion in Hematology 10:142-149.

Rusconi, C.P. et al., "Subcutaneous Administration of the Direct FIXa Inhibitor RB006 Provides Persistent Inhibition of Thrombin Generation," (2010) Circulation 122: A12822.

Rusconi, C.P. et al., "Antidote-mediated control of an anticoagulant aptamer in vivo," (2004) Nature Biotechnology 22(11):1423-1428.

Rusconi, C.P. et al., "Blocking the initiation of coagulation by RNA aptamers to factor VIIa.," (2000) Thromb Haemost 84(5):841-8.

Rusconi, C.P. et al., "RNA aptamers as reversible antagonists of coagulation factor IXa," (2002) Nature 419(5):90-94.

Steen-Burrell, K.A. et al., "Development of an Antidote-Controlled RNA Probe for Molecular Thrombi Imaging," Abstract submitted to Arteriosclerosis, Thrombosis and Vascular Biology (ATVB) Meeting. May 2015.

The National Institute of Neurological Disorders and Stroke rt-PA Stroke Study Group. "Tissue Plasminogen Activator for Acute Ischemic Stroke," (1995) New England Journal of Medicine 333:1581-8.

Wang et al., "A DNA aptamer which binds to and inhibits thrombin exhibits a new structural motif for DNA," (1993) Biochemistry 32:1899-1904.

Wang et al., "Aptamers as therapeutics in cardiovascular diseases," (2011) Curr Med Chem 18:4169-74.

Werstrick et al., "Murine Models of Vascular Thrombosis," (2007)Arterioscler Thromb Vasc Biol 27:2079-2093.

White, R. et al., "Generation of Species Cross-reactive Aptamers Using Toggle SELEX," (2001) Molecular Therapy 4 (6):567-573.

Wolberg, "Thrombin generation and fibrin clot structure," (2007) Blood Rev 21: 131-42.

Wong et al., "A double-filter method for nitrocellulose-filter binding: application to protein-nucleic acid interactions," (1993) Proc Natl Acad Sci USA 90(12): 5428-5432.

Woodruff, R.S. & Sullenger, B.A. "Modulation of the Coagulation Cascade Using Aptamers" Arteriosclerosis, Thrombosis, and Vascular Biology, 35(10):2083-2091 (2015).

Office Action for U.S. Appl. No. 16/334,307, mailed Dec. 13, 2019.

Office Action for U.S Appl. No. 17/146,147, mailed May 1, 2023.

Kandimalla, E.R. et al. "Design, biochemical, biophysical and biological properties of cooperative antisense oligonucleotides." Nucleic Acids Res. Sep. 11, 1995; 23(17): 3578-3584.

Becker et al., "Nucleic acid aptamers in therapeutic anticoagulation. Technology, development and clinical application," (2005) Thromb. Haemost. 93: 1014-1020.

Berkhemer et al., "A randomized trial of intraarterial treatment for acute ischemic stroke," (2015) The New England journal of medicine 372:11-20.

Bompiani et al., "A high affinity, antidote-controllable prothrombin and thrombin-binding RNA aptamer inhibits thrombin generation and thrombin activity," (2012) J Thromb Haemost 10:870-80.

Bompiani et al., "Probing the Coagulation Pathway with Aptamers Identifies Combinations that Synergistically Inhibit Blood Clot Formation" (2014) Chemistry & Biology 21: 935-944.

Buddai et al., "An anticoagulant RNA aptamer that inhibits proteinase-cofactor interactions within prothrombinase," (2010) J Biol Chem 285:5212-23.

Chan et al. "Phase 1b Randomized Study of Antidote-Controlled Modulation of Factor IXa Activity in Patients With Stable Coronary Artery Disease" (2008) Circulation 117:2865-2874.

Chan et al., "A randomized, repeat-dose, pharmacodynamic and safety study of an antidote-controlled factor IXa inhibitor," (2008) Journal of Thrombosis & Haemostasis 6:789-796.

Cohen et al., "First clinical application of an actively reversible direct factor IXa inhibitor as an anticoagulation strategy in patients undergoing percutaneous coronary intervention," (2010) Circulation 122: 614-22.

Cosmi, "ARC-1779, a PEGylated aptamer antagonist of von Willebrand factor for potential use as an anticoagulant or antithrombotic agent," (2009) Curr Opin Molec Therap 11 :322-328.

Diaz et al., "P-selectin inhibition therapeutically promotes thrombus resolution and prevents vein wall fibrosis better than enoxaparin and an inhibitor to von Willebrand factor," (2015) Arteriosclerosis, thrombosis, and vascular biology 35:829-37.

(56) References Cited

OTHER PUBLICATIONS

Diener et al., ""Inhibition of von Willebrand factor-mediated platelet activation and thrombosis by the anti-von Willebrand factor A1-domain aptamer ARC1779,"" (2009) J. Thromb. Haemost 7:1155-1162.
Dougan et al., "Evaluation of DNA aptamers directed to thrombin as potnetial thrombus imaging agents," (2003) Nuclear Medicine and Biology 30:61-72.
Dyke et al., "First-in-human experience of an antidote-controlled anticoagulant using RNA aptamer technology: a phase 1a pharmacodynamic evaluation of a drug-antidote pair for the controlled regulation of factor IXa activity," (2006) Circulation 114:2490-2497.
Edmunds and Coleman, "Thrombin During Cardiopulmonary Bypass," (2006) The Annals of Thoracic Surgery 82:2315-22.
Ellington et al., "In vitro selection of RNA molecules that bind specific ligands." (1990) Nature 346:818-22.
Franciscis et al., "Nucleic Acid Aptamers for In Vivo Molecular Imaging," (2012) Molecular Imaging Chapter 5.
GenBank Accession No. CP000494 "BTAi1, complete genome" Jan. 28, 2014.
Gilbert et al., "First-in-Human Evaluation of Anti-von Willebrand Factor Therapeutic Aptamer ARC1779 in Healthy Volunteers," (2007) Circulation 116:2678-2686.
Hemker et al., "Calibrated automated thrombin generation measurement in clotting plasma," (2003) Pathophysiol Haemost Thromb 33: 4-15.
International Search Report and Written Opinion for PCT/US2006/036109 dated Sep. 5, 2007.
International Search Report and Written Opinion for PCT/US2007/022358 dated Aug. 18, 2008.
International Search Report and Written Opinion for PCT/US2008/004119 dated Jun. 26, 2008.
International Search Report and Written Opinion for PCT/US2012/036783 dated Nov. 23, 2012.
International Search Report and Written Opinion for PCT/US2016/029745 dated Oct. 7, 2016.
International Search Report and Written Opinion for PCT/US2017/052063 dated Jan. 30, 2018.
James et al., "A molecular imaging primer: modalities, imaging agents, and applications," (2012) Physiol Rev 92 (2):897-965.
Joachimi, A. et al., "A new anticoagulant-antidote pair: Control of thrombin activity by aptamers and porphyrins," (2007) Journal of the American Chemical Society 129(11):3036-3037.
Kiefer, T.L. et al., "Inhibitors of platelet adhesion," (2009) Circulation 120:2488-2495.
Koster et al., "High antithrombin III levels attenuate hemostatic activation and leukocyte activation during cardiopulmonary bypass," (2003) Journal of Thoracic & Cardiovascular Surgery 126: 906-7.
Lansberg et al., "Efficacy and safety of tissue plasminogen activator 3 to 4.5 hours after acute ischemic stroke: a metaanalysis," (2009) Stroke 40:2438-41.
Li, M. et al., "Selecting aptamers for a glycoprotein through the incorporation of the boronic acid moiety," (2008) J. Am. Chem. Soc.130(38):12636-12638.
Long, S.B., et al., "Crystal Structure of an RNA aptamer bound to thrombin," (2008) RNA 14:2504-2512.
Mackman, N., "Triggers, targets and treatments for thrombosis," (2008) Nature 451(7181):914-918.
Markus et al., "The von Willebrand inhibitor ARC1779 reduces cerebral embolization after carotid endarterectomy: a randomized trial," (2011) Stroke 42:2149-53.
Mayr et al., "The aptamer ARC1779 blocks von Willebrand factor-dependent platelet function in patients with thrombotic thrombocytopenia purpura ex vivo," (2010) Transfusion 50:1079-1087.
Monroe et al., "A mouse bleeding model to study oral anticoagulants," (2014) Thrombosis research 133 Suppl 1: S6-8.
Monroe et al., "Platelets and thrombin generation," (2002) Arterioscler Thromb Vasc Biol 22:138 1-9.
Mozaffarian et al., "Heart Disease and Stroke Statistics—2016 Update: A Report From the American Heart Association," (2016) Circulation 133:e38-60.
Nimjee et al., "A novel antidote-controlled anticoagulant reduces thrombin generation and inflammation and improves cardiac function in cardiopulmonary bypass surgery," (2006) Mol. Ther. 14:408-45.
Nimjee et al., "Aptamers as Therapeutics," (2017) Annual review of pharmacology and toxicology 57:61-79.
Nimjee et al., "Aptamers: an emerging class of therapeutics," (2005) Annual review of medicine 56:555-83.
Nimjee et al., "Rapidly regulating platelet activity in vivo with an antidote controlled platelet inhibitor," (2012) Molecular therapy : the journal of the American Society of Gene Therapy 20:391-7.
Nimjee et al., "Synergistic effect of aptamers that inhibit exosites 1 and 2 on thrombin," (2009) RNA 15:2105-11.
Nimjee et al., "The potential of aptamers as anticoagulants," (2005) Trends in cardiovascular medicine 15:41-5.
Office Action for U.S. Appl. No. 11/992,125 mailed Apr. 9, 2012.
Office Action for U.S. Appl. No. 11/992,125 mailed Aug. 16, 2011.
Office Action for U.S. Appl. No. 13/296,045 mailed Aug. 6, 2012.
Office Action for U.S. Appl. No. 13/878,539 mailed Dec. 8, 2014.
Office Action for U.S. Appl. No. 13/878,539 mailed Jul. 22, 2014.
Office Action for U.S. Appl. No. 12/311,943 mailed Jun. 21, 2013.
Keefe, A.D. et al. (2010). Aptamers as therapeutics. Nature reviews Drug discovery, 9(7), 537-550.
Leebeek et al., "Von Willebrand's Disease," (2016) The New England journal of medicine 375:2067-2080.
Soule, E.E. et al. "Targeting Two Coagulation Cascade Proteases with a Bivalent Aptamer Yields a Potent and Antidote-Controllable Anticoagulant" Nucleic Acid Ther. Feb. 1, 2016; 26(1): 1-9.

* cited by examiner

Figure 2
T59; SEQ ID NO: 4
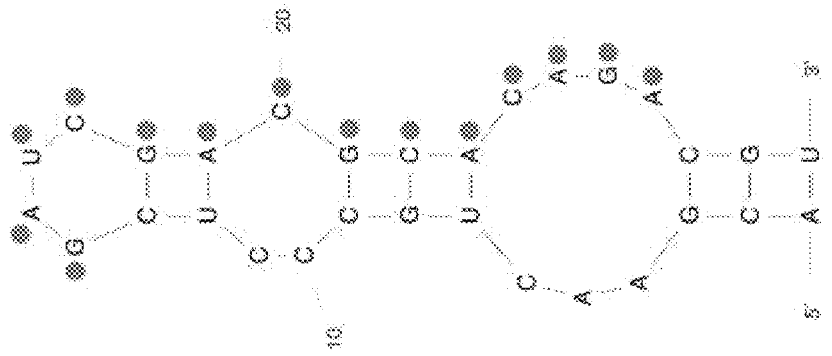
Dots: Antidote: AO11; SEQ ID NO: 113
T79; SEQ ID NO: 3
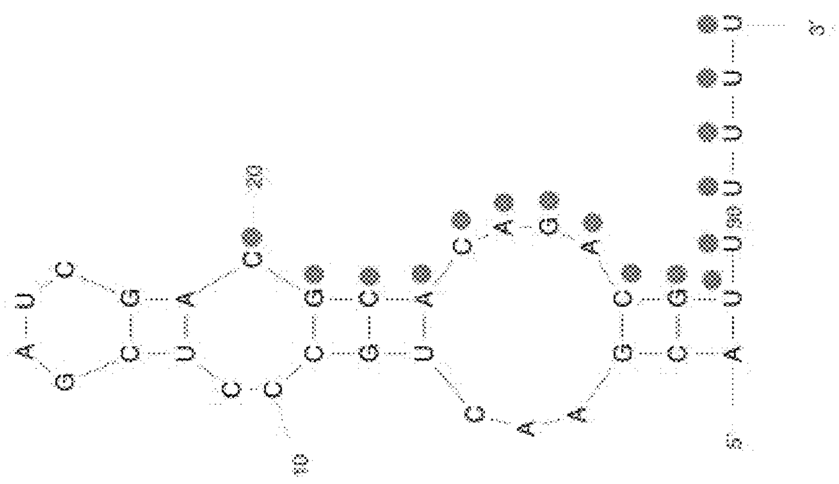
Dots: Antidote: AO55; SEQ ID NO: 157

T79 VRT7; SEQ ID NO: 7

$B_{max}$ = 56%
$K_d$ = 11.2nM

- Vessel occluded in ~4-5 minutes 0.375 mg/kg

Figure 12
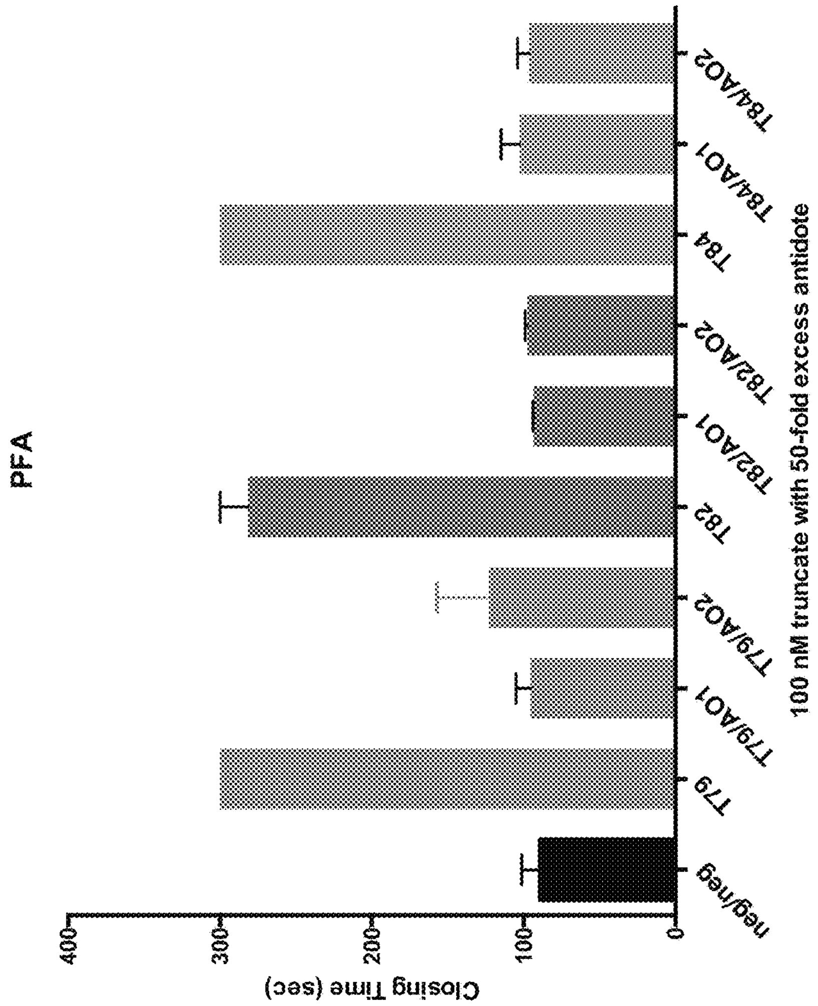
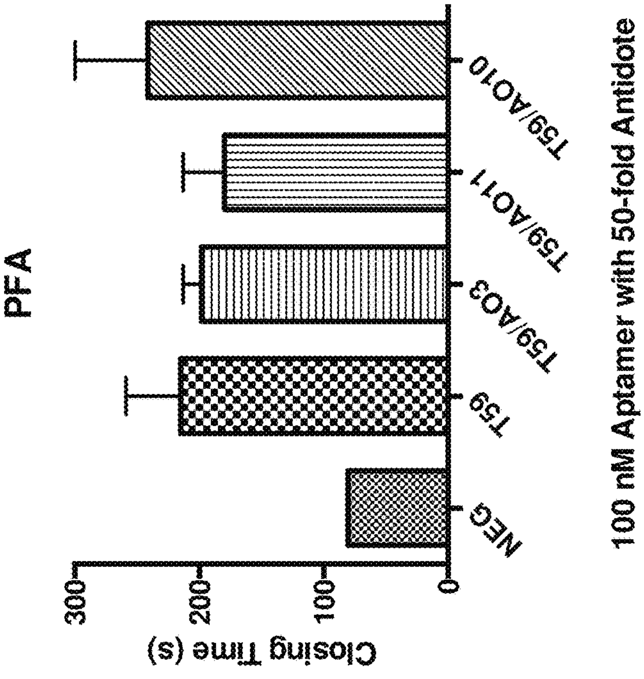

DTRI-038: SEQ ID NO: 180

5' mAmAmAmAmCmGmUmCmUmGmUmGmCmG 3'

Figure 15

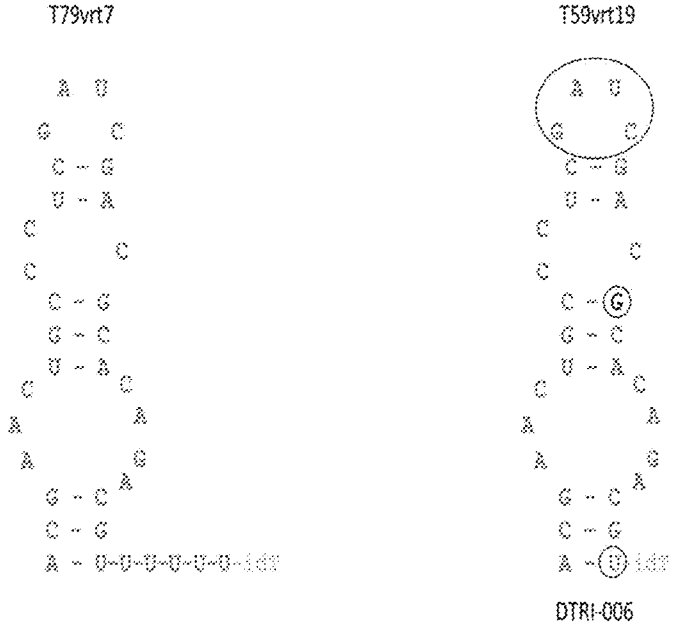

Red= 2'OMethyl Blue= 2'F Black=2'OH Green=idT

| Sequence ID | Target | Description | Sequence |
|---|---|---|---|
| DTRI-006 | VWF | T59VRT19 | mAmCmGmAmAmCmUmGfCfCfCmUmCmGmAmUmCmGmAfCrGfCmAmCmAmGmAmCmGfUidT |
| DTRI-007 | VWF | DTRI006 S2fG | mAmCmGmAmAmCmUmGfCfCfCmUmCmGmAmUmCmGmAfCfGfCmAmCmAmGmAmCmGfUidT |
| DTRI-008 | VWF | DTRI006 S1mU | mAmCmGmAmAmCmUmGfCfCfCmUmCmGmAmUmCmGmAfCrGfCmAmCmAmGmAmCmGmUidT |
| DTRI-009 | VWF | DTRI006 L3spacer | mAmCmGmAmAmCmUmGfCfCfCmUmC(c6spacer)mGmAfCrGfCmAmCmAmGmAmCmGfUidT |
| DTRI-010 | VWF | DTRI006 S2dG | mAmCmGmAmAmCmUmGfCfCfCmUmCmGmAmUmCmGmAfCdGfCmAmCmAmGmAmCmGfUidT |
| DTRI-011 | VWF | DTRI006 L3 GUAA | mAmCmGmAmAmCmUmGfCfCfCmUmCmGmUmAmAmGmAfCrGfCmAmCmAmGmAmCmGfUidT |
| DTRI-012 | VWF | DTR1011 3'5U tail | mAmCmGmAmAmCmUmGfCfCfCmUmCmGmUmAmAmGmAfCrGfCmAmCmAmGmAmCmGfUmUmUmUmUmUidT |
| DTRI-013 | VWF | DTRI006 s1 b1 sub | mCmCmGmAmAmCmUmGfCfCfCmUmCmGmAmUmCmGmAfCrGfCmAmCmAmGmAmCmGmGidT |

Figure 16
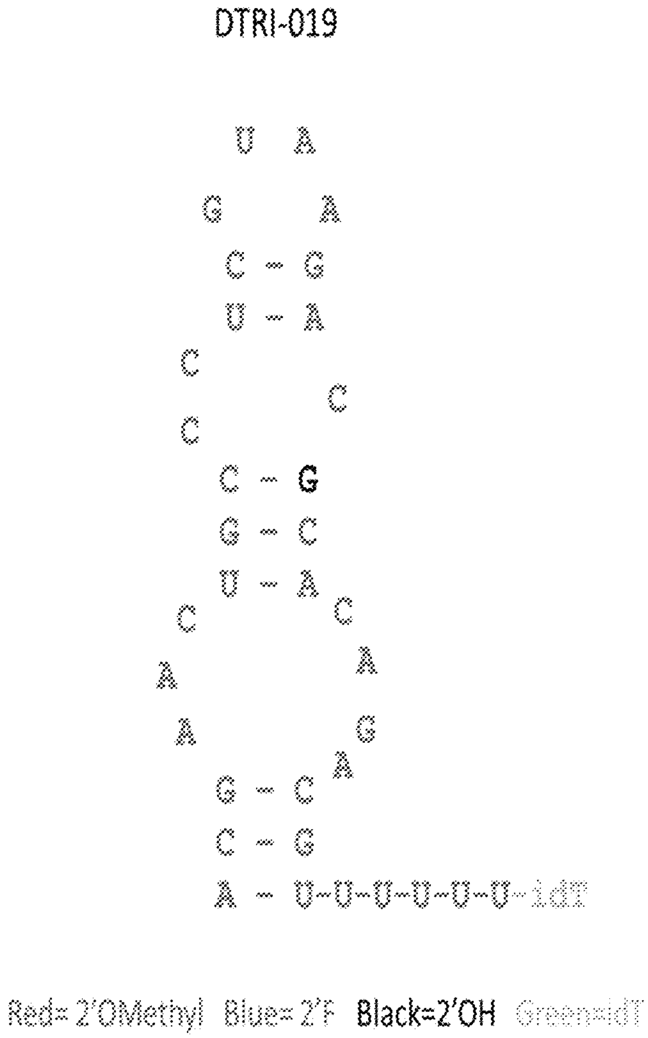
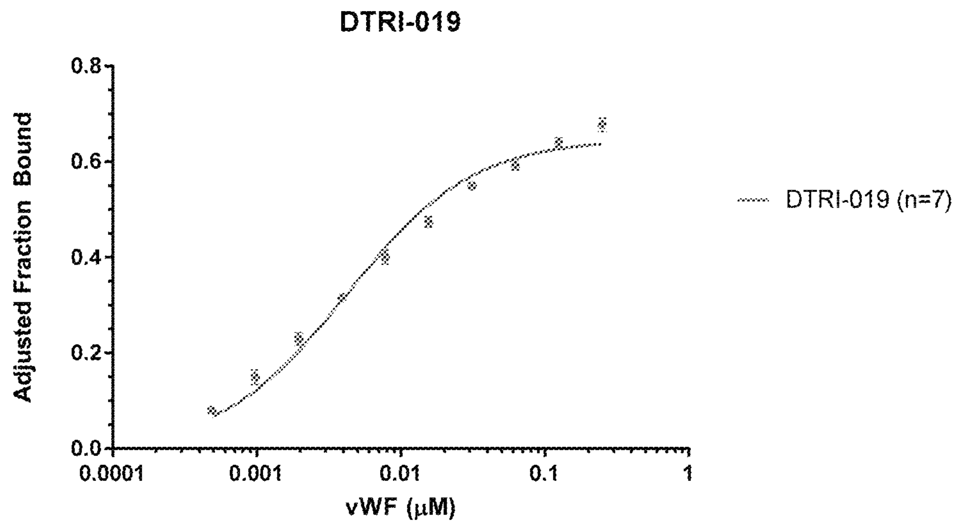
| | |
|---|---|
| One site binding (hyperbola) | |
| Best-fit values | |
| Bmax | 0.6483 |
| Kd | 0.004258 |

| One site binding (hyperbola) | |
|---|---|
| Best-fit values | |
| Bmax | 0.5639 |
| Kd | 0.01119 |

Figure 20A-E

Figure 23A-D
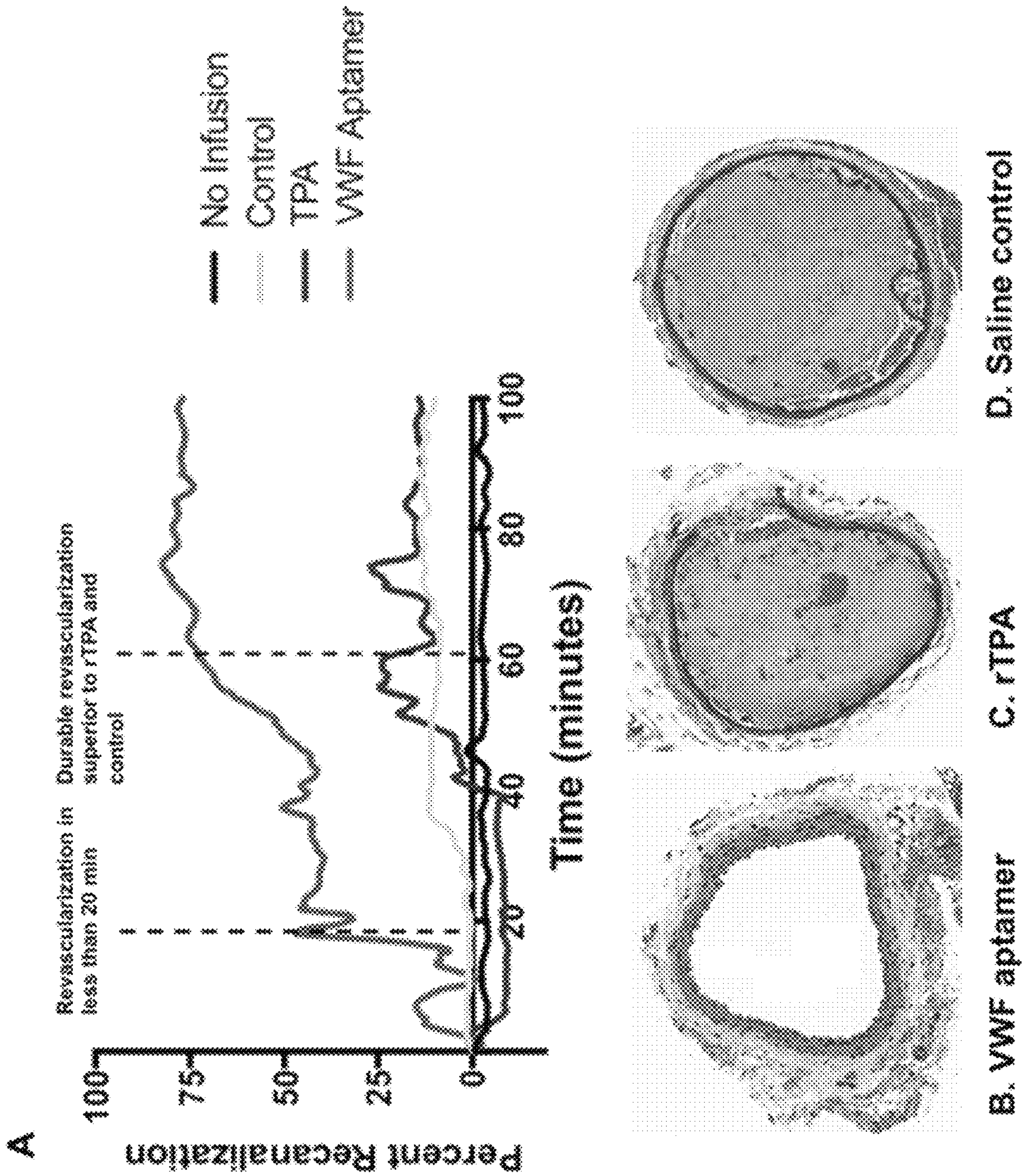

Figure 24A-B
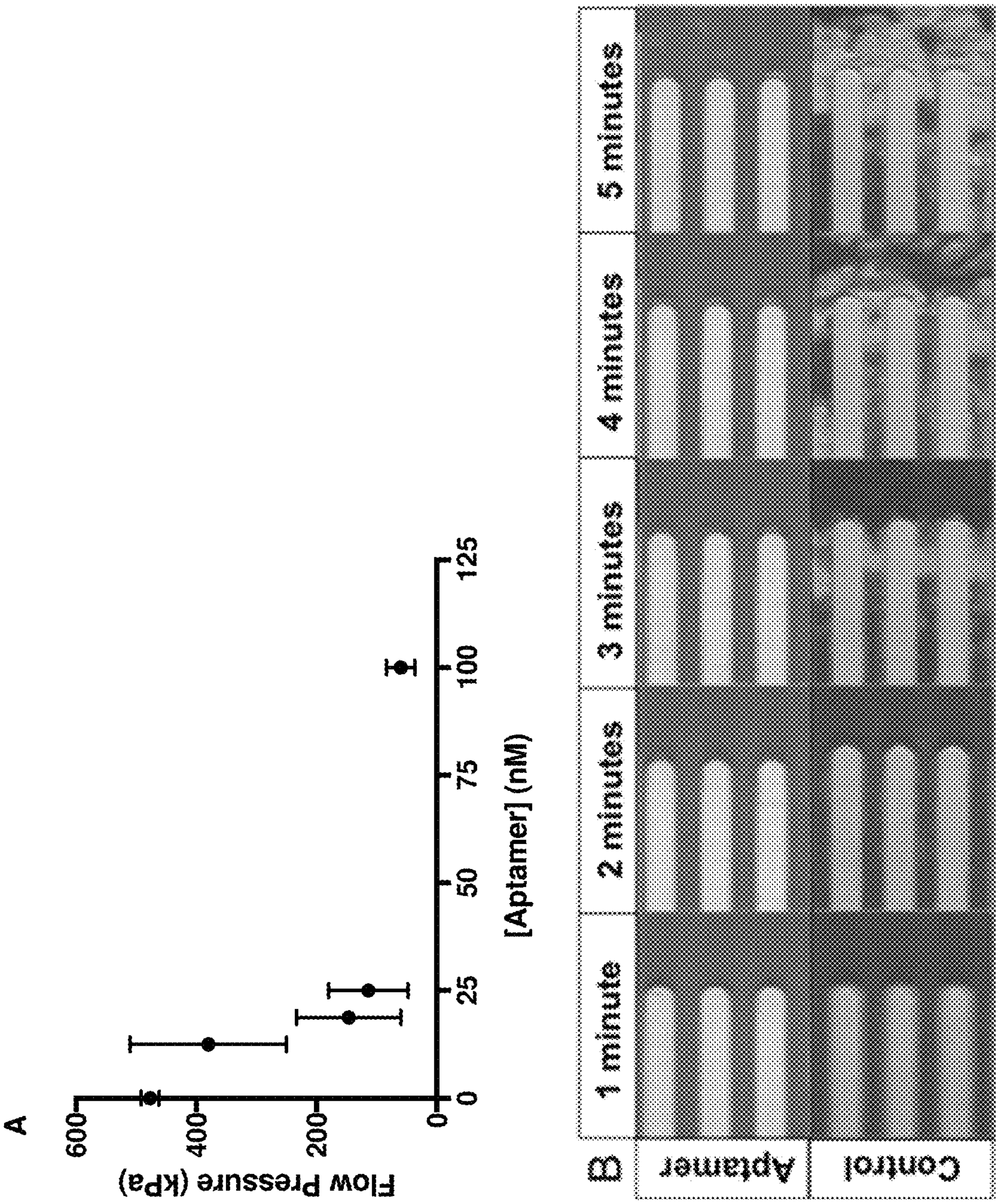

SEQUENCE LISTING

```
Sequence total quantity: 180
SEQ ID NO: 1            moltype = DNA  length = 12
FEATURE                 Location/Qualifiers
misc_feature            1..12
                        note = Synthetic
misc_feature            6
                        note = Mixed DNA/RNA - every T can be U
source                  1..12
                        mol_type = other DNA
                        organism = synthetic construct
misc_feature            11
                        note = mixed RNA/DNA- every T can be a U
SEQUENCE: 1
cgaactgccc tc                                                      12

SEQ ID NO: 2            moltype = DNA  length = 12
FEATURE                 Location/Qualifiers
misc_feature            1..12
                        note = Synthetic
source                  1..12
                        mol_type = other DNA
                        organism = synthetic construct
SEQUENCE: 2
gacgcacaga cg                                                      12

SEQ ID NO: 3            moltype = RNA  length = 35
FEATURE                 Location/Qualifiers
misc_feature            1..35
                        note = Synthetic
```

```
source                  1..35
                        mol_type = other RNA
                        organism = synthetic construct
SEQUENCE: 3
acgaactgcc ctcgatcgac gcacagacgt ttttt                             35

SEQ ID NO: 4            moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 4
acgaactgcc ctcgatcgac gcacagacgt                                   30

SEQ ID NO: 5            moltype = RNA  length = 34
FEATURE                 Location/Qualifiers
misc_feature            1..34
                        note = Synthetic
source                  1..34
                        mol_type = other RNA
                        organism = synthetic construct
SEQUENCE: 5
acgaactgcc ctcgattatt cgacgcacag acgt                              34

SEQ ID NO: 6            moltype = RNA  length = 44
FEATURE                 Location/Qualifiers
misc_feature            1..44
                        note = Synthetic
source                  1..44
                        mol_type = other RNA
                        organism = synthetic construct
SEQUENCE: 6
acgaactgcc ctcagctact ttcatgttgc tgacgcacag acgt                   44

SEQ ID NO: 7            moltype = RNA  length = 35
FEATURE                 Location/Qualifiers
misc_feature            1..35
                        note = Synthetic
modified_base           1..8
                        mod_base = OTHER
                        note = 2' O-methyl nucleotide
modified_base           9..11
                        mod_base = OTHER
                        note = 2' Fluoro nucleotide
modified_base           12..19
                        mod_base = OTHER
                        note = 2' O-methyl nucleotide
modified_base           20..22
                        mod_base = OTHER
                        note = 2' Fluoro nucleotide
modified_base           23..35
                        mod_base = OTHER
                        note = 2' O-methyl nucleotide
source                  1..35
                        mol_type = other RNA
                        organism = synthetic construct
SEQUENCE: 7
acgaactgcc ctcgatcgac gcacagacgt ttttt                             35

SEQ ID NO: 8            moltype = RNA  length = 35
FEATURE                 Location/Qualifiers
misc_feature            1..35
                        note = Synthetic
modified_base           1..8
                        mod_base = OTHER
                        note = 2' O-methyl nucleotide
modified_base           9..11
                        mod_base = OTHER
                        note = 2' Fluoro nucleotide
modified_base           12..19
                        mod_base = OTHER
                        note = 2' O-methyl nucleotide
modified_base           20
                        mod_base = OTHER
                        note = 2' Fluoro nucleotide
modified_base           21
                        mod_base = OTHER
```

```
                        note = 2 Ribo nucleotide
modified_base           22
                        mod_base = OTHER
                        note = 2' Fluoro nucleotide
modified_base           23..35
                        mod_base = OTHER
                        note = 2' O-methyl nucleotide
source                  1..35
                        mol_type = other RNA
                        organism = synthetic construct
SEQUENCE: 8
acgaactgcc ctcgtaagac gcacagacgt ttttt                         35

SEQ ID NO: 9            moltype = RNA  length = 35
FEATURE                 Location/Qualifiers
misc_feature            1..35
                        note = Synthetic
modified_base           1..8
                        mod_base = OTHER
                        note = 2' O-methyl nucleotide
modified_base           9..11
                        mod_base = OTHER
                        note = 2' Fluoro nucleotide
modified_base           12..19
                        mod_base = OTHER
                        note = 2' O-methyl nucleotide
modified_base           20
                        mod_base = OTHER
                        note = 2' Fluoro nucleotide
modified_base           21
                        mod_base = OTHER
                        note = 2 Ribo nucleotide
modified_base           22
                        mod_base = OTHER
                        note = 2' Fluoro nucleotide
modified_base           23..35
                        mod_base = OTHER
                        note = 2' O-methyl nucleotide
source                  1..35
                        mol_type = other RNA
                        organism = synthetic construct
SEQUENCE: 9
acgaactgcc ctcgtaagac gcacagacgt ttttt                         35

SEQ ID NO: 10           moltype = RNA  length = 80
FEATURE                 Location/Qualifiers
misc_feature            1..80
                        note = Synthetic
source                  1..80
                        mol_type = other RNA
                        organism = synthetic construct
SEQUENCE: 10
gggaggacga tgcggtggac gaactgccct cagctacttt catgttgctg acgcacagac  60
gactcgctga ggatccgaga                                          80

SEQ ID NO: 11           moltype = RNA  length = 60
FEATURE                 Location/Qualifiers
misc_feature            1..60
                        note = Synthetic
source                  1..60
                        mol_type = other RNA
                        organism = synthetic construct
SEQUENCE: 11
gggaggtgga cgaactgccc tcagctactt tcatgttgct gacgcacaga cgactcgctg  60

SEQ ID NO: 12           moltype = RNA  length = 57
FEATURE                 Location/Qualifiers
misc_feature            1..57
                        note = Synthetic
source                  1..57
                        mol_type = other RNA
                        organism = synthetic construct
SEQUENCE: 12
gggaggacga actgccctca gctactttca tgttgctgac gcacagacga ctcgctg     57

SEQ ID NO: 13           moltype = RNA  length = 54
FEATURE                 Location/Qualifiers
misc_feature            1..54
                        note = Synthetic
```

```
source                  1..54
                        mol_type = other RNA
                        organism = synthetic construct
SEQUENCE: 13
gggaggaact gccctcagct actttcatgt tgctgacgca cagacgactc gctg        54

SEQ ID NO: 14           moltype = RNA  length = 51
FEATURE                 Location/Qualifiers
misc_feature            1..51
                        note = Synthetic
source                  1..51
                        mol_type = other RNA
                        organism = synthetic construct
SEQUENCE: 14
gggaggtgcc ctcagctact ttcatgttgc tgacgcacag acgactcgct g           51

SEQ ID NO: 15           moltype = RNA  length = 28
FEATURE                 Location/Qualifiers
misc_feature            1..28
                        note = Synthetic
source                  1..28
                        mol_type = other RNA
                        organism = synthetic construct
SEQUENCE: 15
gggaggtcag ctactttcat gttgctga                                     28

SEQ ID NO: 16           moltype = RNA  length = 57
FEATURE                 Location/Qualifiers
misc_feature            1..57
                        note = Synthetic
source                  1..57
                        mol_type = other RNA
                        organism = synthetic construct
SEQUENCE: 16
gggaggtgga cgaactgccc tcagctacca tgttgctgac gcacagacga ctcgctg     57

SEQ ID NO: 17           moltype = RNA  length = 54
FEATURE                 Location/Qualifiers
misc_feature            1..54
                        note = Synthetic
source                  1..54
                        mol_type = other RNA
                        organism = synthetic construct
SEQUENCE: 17
gggaggtgga cgaactgccc tcagctacgt tgctgacgca cagacgactc gctg        54

SEQ ID NO: 18           moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 18
gggaggtgga cgaactgccc tacgcacaga cgactcgctg                        40

SEQ ID NO: 19           moltype = RNA  length = 57
FEATURE                 Location/Qualifiers
misc_feature            1..57
                        note = Synthetic
source                  1..57
                        mol_type = other RNA
                        organism = synthetic construct
SEQUENCE: 19
gggaggtgga cgaactgccc tctactttca tgttgctgac gcacagacga ctcgctg     57

SEQ ID NO: 20           moltype = RNA  length = 54
FEATURE                 Location/Qualifiers
misc_feature            1..54
                        note = Synthetic
source                  1..54
                        mol_type = other RNA
                        organism = synthetic construct
SEQUENCE: 20
gggaggtgga cgaactgccc tctttcatgt tgctgacgca cagacgactc gctg        54

SEQ ID NO: 21           moltype = RNA  length = 54
FEATURE                 Location/Qualifiers
misc_feature            1..54
```

```
                        note = Synthetic
source                  1..54
                        mol_type = other RNA
                        organism = synthetic construct
SEQUENCE: 21
gggaggtgga cgaactgccc tctactttca tgttgacgca cagacgactc gctg        54

SEQ ID NO: 22           moltype = RNA  length = 46
FEATURE                 Location/Qualifiers
misc_feature            1..46
                        note = Synthetic
source                  1..46
                        mol_type = other RNA
                        organism = synthetic construct
SEQUENCE: 22
gggaggtcag ctactttcat gttgctgacg cacagacgac tcgctg                 46

SEQ ID NO: 23           moltype = RNA  length = 53
FEATURE                 Location/Qualifiers
misc_feature            1..53
                        note = Synthetic
source                  1..53
                        mol_type = other RNA
                        organism = synthetic construct
SEQUENCE: 23
ggacgaactg ccctcagcta ctttcatgtt gctgacgcac agacgactcg ctg         53

SEQ ID NO: 24           moltype = RNA  length = 51
FEATURE                 Location/Qualifiers
misc_feature            1..51
                        note = Synthetic
source                  1..51
                        mol_type = other RNA
                        organism = synthetic construct
SEQUENCE: 24
acgaactgcc ctcagctact ttcatgttgc tgacgcacag acgactcgct g           51

SEQ ID NO: 25           moltype = RNA  length = 48
FEATURE                 Location/Qualifiers
misc_feature            1..48
                        note = Synthetic
source                  1..48
                        mol_type = other RNA
                        organism = synthetic construct
SEQUENCE: 25
ggacgaactg ccctcagcta ctttcatgtt gctgacgcac agacgtcc               48

SEQ ID NO: 26           moltype = RNA  length = 44
FEATURE                 Location/Qualifiers
misc_feature            1..44
                        note = Synthetic
source                  1..44
                        mol_type = other RNA
                        organism = synthetic construct
SEQUENCE: 26
ccgaactgcc ctcagctact ttcatgttgc tgacgcacag acgg                   44

SEQ ID NO: 27           moltype = RNA  length = 55
FEATURE                 Location/Qualifiers
misc_feature            1..55
                        note = Synthetic
source                  1..55
                        mol_type = other RNA
                        organism = synthetic construct
SEQUENCE: 27
gggaggacga actgccctca gctacttatg ttgctgacgc acagacgact cgctg       55

SEQ ID NO: 28           moltype = RNA  length = 56
FEATURE                 Location/Qualifiers
misc_feature            1..56
                        note = Synthetic
source                  1..56
                        mol_type = other RNA
                        organism = synthetic construct
SEQUENCE: 28
gggaggacga actgccctca gctacttcat gttgctgacg cacagacgac tcgctg      56

SEQ ID NO: 29           moltype = RNA  length = 53
FEATURE                 Location/Qualifiers
```

```
misc_feature           1..53
                       note = Synthetic
source                 1..53
                       mol_type = other RNA
                       organism = synthetic construct
SEQUENCE: 29
gggaggacga actgccctca gctattatta gctgacgcac agacgactcg ctg        53

SEQ ID NO: 30          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 30
ccgaactgcc ctcagctatt attagctgac gcacagacgg                      40

SEQ ID NO: 31          moltype = RNA  length = 44
FEATURE                Location/Qualifiers
misc_feature           1..44
                       note = Synthetic
source                 1..44
                       mol_type = other RNA
                       organism = synthetic construct
SEQUENCE: 31
gggaactgcc ctcagctact ttcatgttgc tgacgcacag accc                 44

SEQ ID NO: 32          moltype = RNA  length = 48
FEATURE                Location/Qualifiers
misc_feature           1..48
                       note = Synthetic
source                 1..48
                       mol_type = other RNA
                       organism = synthetic construct
SEQUENCE: 32
ggacgaactg ccctcagcta ctttcatgtt gctgacgcac agacgact             48

SEQ ID NO: 33          moltype = RNA  length = 42
FEATURE                Location/Qualifiers
misc_feature           1..42
                       note = Synthetic
source                 1..42
                       mol_type = other RNA
                       organism = synthetic construct
SEQUENCE: 33
acgaactgcc ctcagcactt tcatgtgctg acgcacagac gt                   42

SEQ ID NO: 34          moltype = RNA  length = 42
FEATURE                Location/Qualifiers
misc_feature           1..42
                       note = Synthetic
source                 1..42
                       mol_type = other RNA
                       organism = synthetic construct
SEQUENCE: 34
acgaactgcc ctcgctactt tcatgttgcg acgcacagac gt                   42

SEQ ID NO: 35          moltype = RNA  length = 42
FEATURE                Location/Qualifiers
misc_feature           1..42
                       note = Synthetic
source                 1..42
                       mol_type = other RNA
                       organism = synthetic construct
SEQUENCE: 35
acgaactgcc ctcagtactt tcatgttctg acgcacagac gt                   42

SEQ ID NO: 36          moltype = RNA  length = 42
FEATURE                Location/Qualifiers
misc_feature           1..42
                       note = Synthetic
source                 1..42
                       mol_type = other RNA
                       organism = synthetic construct
SEQUENCE: 36
acgaactgcc ctcagctatt tcatttgctg acgcacagac gt                   42

SEQ ID NO: 37          moltype = RNA  length = 42
```

```
FEATURE                Location/Qualifiers
misc_feature           1..42
                       note = Synthetic
source                 1..42
                       mol_type = other RNA
                       organism = synthetic construct
SEQUENCE: 37
acgaactgcc ctcagctact tatgttgctg acgcacagac gt                        42

SEQ ID NO: 38          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 38
acgaactgcc ctcgcacttt catgtgcgac gcacagacgt                           40

SEQ ID NO: 39          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 39
acgaactgcc ctcagacttt catgtctgac gcacagacgt                           40

SEQ ID NO: 40          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 40
acgaactgcc ctcagcattt cattgctgac gcacagacgt                           40

SEQ ID NO: 41          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 41
acgaactgcc ctcagcactt atgtgctgac gcacagacgt                           40

SEQ ID NO: 42          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 42
acgaactgcc ctcgtacttt catgttcgac gcacagacgt                           40

SEQ ID NO: 43          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 43
acgaactgcc ctcgctattt catttgcgac gcacagacgt                           40

SEQ ID NO: 44          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 44
acgaactgcc ctcgctactt atgttgcgac gcacagacgt                           40
```

```
SEQ ID NO: 45          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 45
acgaactgcc ctcagtattt catttctgac gcacagacgt                        40

SEQ ID NO: 46          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 46
acgaactgcc ctcagtactt atgttctgac gcacagacgt                        40

SEQ ID NO: 47          moltype = RNA  length = 40
FEATURE                Location/Qualifiers
misc_feature           1..40
                       note = Synthetic
source                 1..40
                       mol_type = other RNA
                       organism = synthetic construct
SEQUENCE: 47
acgaactgcc ctcagctatt atttgctgac gcacagacgt                        40

SEQ ID NO: 48          moltype = RNA  length = 36
FEATURE                Location/Qualifiers
misc_feature           1..36
                       note = Synthetic
source                 1..36
                       mol_type = other RNA
                       organism = synthetic construct
SEQUENCE: 48
acgaactgcc ctcgacttat gtcgacgcac agacgt                            36

SEQ ID NO: 49          moltype = RNA  length = 38
FEATURE                Location/Qualifiers
misc_feature           1..38
                       note = Synthetic
source                 1..38
                       mol_type = other RNA
                       organism = synthetic construct
SEQUENCE: 49
acgaactgcc ctcgcactta tgtgcgacgc acagacgt                          38

SEQ ID NO: 50          moltype = RNA  length = 38
FEATURE                Location/Qualifiers
misc_feature           1..38
                       note = Synthetic
source                 1..38
                       mol_type = other RNA
                       organism = synthetic construct
SEQUENCE: 50
acgaactgcc ctcagactta tgtctgacgc acagacgt                          38

SEQ ID NO: 51          moltype = RNA  length = 38
FEATURE                Location/Qualifiers
misc_feature           1..38
                       note = Synthetic
source                 1..38
                       mol_type = other RNA
                       organism = synthetic construct
SEQUENCE: 51
acgaactgcc ctcagcatta ttgctgacgc acagacgt                          38

SEQ ID NO: 52          moltype = RNA  length = 43
FEATURE                Location/Qualifiers
misc_feature           1..43
                       note = Synthetic
source                 1..43
                       mol_type = other RNA
                       organism = synthetic construct
SEQUENCE: 52
acgaactgcc ctcagctact ttcatgttgc tgacgcacaa cgt                    43
```

```
SEQ ID NO: 53          moltype = RNA  length = 43
FEATURE                Location/Qualifiers
misc_feature           1..43
                       note = Synthetic
source                 1..43
                       mol_type = other RNA
                       organism = synthetic construct
SEQUENCE: 53
acgaactgcc ctcagctact ttcatgttgc tgacgcacga cgt                43

SEQ ID NO: 54          moltype = RNA  length = 41
FEATURE                Location/Qualifiers
misc_feature           1..41
                       note = Synthetic
source                 1..41
                       mol_type = other RNA
                       organism = synthetic construct
SEQUENCE: 54
acgactgccc tcagctactt tcatgttgct gacgcacacg t                  41

SEQ ID NO: 55          moltype = RNA  length = 24
FEATURE                Location/Qualifiers
misc_feature           1..24
                       note = Synthetic
source                 1..24
                       mol_type = other RNA
                       organism = synthetic construct
SEQUENCE: 55
acgaactgcc ctacgcacag acgt                                     24

SEQ ID NO: 56          moltype = RNA  length = 26
FEATURE                Location/Qualifiers
misc_feature           1..26
                       note = Synthetic
source                 1..26
                       mol_type = other RNA
                       organism = synthetic construct
SEQUENCE: 56
acgaactgcc ctcgacgcac agacgt                                   26

SEQ ID NO: 57          moltype = RNA  length = 28
FEATURE                Location/Qualifiers
misc_feature           1..28
                       note = Synthetic
source                 1..28
                       mol_type = other RNA
                       organism = synthetic construct
SEQUENCE: 57
acgaactgcc ctcgcgacgc acagacgt                                 28

SEQ ID NO: 58          moltype = RNA  length = 32
FEATURE                Location/Qualifiers
misc_feature           1..32
                       note = Synthetic
source                 1..32
                       mol_type = other RNA
                       organism = synthetic construct
SEQUENCE: 58
acgaactgcc ctcgatttcg acgcacagac gt                            32

SEQ ID NO: 59          moltype = RNA  length = 22
FEATURE                Location/Qualifiers
misc_feature           1..22
                       note = Synthetic
source                 1..22
                       mol_type = other RNA
                       organism = synthetic construct
SEQUENCE: 59
acgaactgcc ccgcacagac gt                                       22

SEQ ID NO: 60          moltype = RNA  length = 32
FEATURE                Location/Qualifiers
misc_feature           1..32
                       note = Synthetic
source                 1..32
                       mol_type = other RNA
                       organism = synthetic construct
SEQUENCE: 60
```

```
acgaactccc tcgattattc gacgacagac gt                          32

SEQ ID NO: 61          moltype = RNA  length = 32
FEATURE                Location/Qualifiers
misc_feature           1..32
                       note = Synthetic
source                 1..32
                       mol_type = other RNA
                       organism = synthetic construct
SEQUENCE: 61
acgaacgccc tcgattattc gacgcacgac gt                          32

SEQ ID NO: 62          moltype = RNA  length = 30
FEATURE                Location/Qualifiers
misc_feature           1..30
                       note = Synthetic
source                 1..30
                       mol_type = other RNA
                       organism = synthetic construct
SEQUENCE: 62
acgaactgcc ctattattac gcacagacgt                             30

SEQ ID NO: 63          moltype = RNA  length = 28
FEATURE                Location/Qualifiers
misc_feature           1..28
                       note = Synthetic
source                 1..28
                       mol_type = other RNA
                       organism = synthetic construct
SEQUENCE: 63
acgaactgcc ctttatacgc acagacgt                               28

SEQ ID NO: 64          moltype = RNA  length = 31
FEATURE                Location/Qualifiers
misc_feature           1..31
                       note = Synthetic
source                 1..31
                       mol_type = other RNA
                       organism = synthetic construct
SEQUENCE: 64
acgaactgct cgattattcg agcacagacg t                           31

SEQ ID NO: 65          moltype = RNA  length = 33
FEATURE                Location/Qualifiers
misc_feature           1..33
                       note = Synthetic
source                 1..33
                       mol_type = other RNA
                       organism = synthetic construct
SEQUENCE: 65
acgaactgcc ctcgattatt cgaccacaga cgt                         33

SEQ ID NO: 66          moltype = RNA  length = 30
FEATURE                Location/Qualifiers
misc_feature           1..30
                       note = Synthetic
source                 1..30
                       mol_type = other RNA
                       organism = synthetic construct
SEQUENCE: 66
acgaactgcc ctcttatgac gcacagacgt                             30

SEQ ID NO: 67          moltype = RNA  length = 32
FEATURE                Location/Qualifiers
misc_feature           1..32
                       note = Synthetic
source                 1..32
                       mol_type = other RNA
                       organism = synthetic construct
SEQUENCE: 67
acgaactgcc ctgattattc acgcacagac gt                          32

SEQ ID NO: 68          moltype = RNA  length = 32
FEATURE                Location/Qualifiers
misc_feature           1..32
                       note = Synthetic
source                 1..32
                       mol_type = other RNA
                       organism = synthetic construct
```

```
SEQUENCE: 68
acgaactgcc ctcattattg acgcacagac gt                               32

SEQ ID NO: 69          moltype = RNA  length = 32
FEATURE                Location/Qualifiers
misc_feature           1..32
                       note = Synthetic
source                 1..32
                       mol_type = other RNA
                       organism = synthetic construct
SEQUENCE: 69
acgaactgcc ctcgttatcg acgcacagac gt                               32

SEQ ID NO: 70          moltype = RNA  length = 35
FEATURE                Location/Qualifiers
misc_feature           1..35
                       note = Synthetic
source                 1..35
                       mol_type = other RNA
                       organism = synthetic construct
SEQUENCE: 70
gcataacgaa ctgccctcga tcgacgcaca gacgt                            35

SEQ ID NO: 71          moltype = RNA  length = 33
FEATURE                Location/Qualifiers
misc_feature           1..33
                       note = Synthetic
source                 1..33
                       mol_type = other RNA
                       organism = synthetic construct
SEQUENCE: 71
cccacgaact gccctcgatc gacgcacaga cgt                              33

SEQ ID NO: 72          moltype = RNA  length = 35
FEATURE                Location/Qualifiers
misc_feature           1..35
                       note = Synthetic
source                 1..35
                       mol_type = other RNA
                       organism = synthetic construct
SEQUENCE: 72
cccccacgaa ctgccctcga tcgacgcaca gacgt                            35

SEQ ID NO: 73          moltype = RNA  length = 35
FEATURE                Location/Qualifiers
misc_feature           1..35
                       note = Synthetic
source                 1..35
                       mol_type = other RNA
                       organism = synthetic construct
SEQUENCE: 73
cacacacgaa ctgccctcga tcgacgcaca gacgt                            35

SEQ ID NO: 74          moltype = RNA  length = 34
FEATURE                Location/Qualifiers
misc_feature           1..34
                       note = Synthetic
source                 1..34
                       mol_type = other RNA
                       organism = synthetic construct
SEQUENCE: 74
aaaaacgaac tgccctcgat cgacgcacag acgt                             34

SEQ ID NO: 75          moltype = RNA  length = 36
FEATURE                Location/Qualifiers
misc_feature           1..36
                       note = Synthetic
source                 1..36
                       mol_type = other RNA
                       organism = synthetic construct
SEQUENCE: 75
cccaaaacga actgccctcg atcgacgcac agacgt                           36

SEQ ID NO: 76          moltype = RNA  length = 33
FEATURE                Location/Qualifiers
misc_feature           1..33
                       note = Synthetic
source                 1..33
                       mol_type = other RNA
```

```
                       organism = synthetic construct
SEQUENCE: 76
acgaactgcc ctcgatcgac gcacagacgt aaa                              33

SEQ ID NO: 77          moltype = RNA  length = 35
FEATURE                Location/Qualifiers
misc_feature           1..35
                       note = Synthetic
source                 1..35
                       mol_type = other RNA
                       organism = synthetic construct
SEQUENCE: 77
acgaactgcc ctcgatcgac gcacagacgt acaca                            35

SEQ ID NO: 78          moltype = RNA  length = 35
FEATURE                Location/Qualifiers
misc_feature           1..35
                       note = Synthetic
source                 1..35
                       mol_type = other RNA
                       organism = synthetic construct
SEQUENCE: 78
acgaactgcc ctcgatcgac gcacagacgt acccg                            35

SEQ ID NO: 79          moltype = RNA  length = 35
FEATURE                Location/Qualifiers
misc_feature           1..35
                       note = Synthetic
source                 1..35
                       mol_type = other RNA
                       organism = synthetic construct
SEQUENCE: 79
acgaactgcc ctcgatcgac gcacagacgt aaaaa                            35

SEQ ID NO: 80          moltype = RNA  length = 35
FEATURE                Location/Qualifiers
misc_feature           1..35
                       note = Synthetic
source                 1..35
                       mol_type = other RNA
                       organism = synthetic construct
SEQUENCE: 80
acgaactgcc ctcgatcgac gcacagacgt acacg                            35

SEQ ID NO: 81          moltype = RNA  length = 36
FEATURE                Location/Qualifiers
misc_feature           1..36
                       note = Synthetic
source                 1..36
                       mol_type = other RNA
                       organism = synthetic construct
SEQUENCE: 81
acgaactgcc ctcgatttca ttcgacgcac agacgt                           36

SEQ ID NO: 82          moltype = RNA  length = 34
FEATURE                Location/Qualifiers
misc_feature           1..34
                       note = Synthetic
source                 1..34
                       mol_type = other RNA
                       organism = synthetic construct
SEQUENCE: 82
acgaactgcc ctcgtttcat cgacgcacag acgt                             34

SEQ ID NO: 83          moltype = RNA  length = 32
FEATURE                Location/Qualifiers
misc_feature           1..32
                       note = Synthetic
source                 1..32
                       mol_type = other RNA
                       organism = synthetic construct
SEQUENCE: 83
acgaactgcc ctctttcatg acgcacagac gt                               32

SEQ ID NO: 84          moltype = RNA  length = 38
FEATURE                Location/Qualifiers
misc_feature           1..38
                       note = Synthetic
source                 1..38
```

```
                        mol_type = other RNA
                        organism = synthetic construct
SEQUENCE: 84
acgaactgcc ctcgatatta ttttcgacgc acagacgt                          38

SEQ ID NO: 85           moltype = RNA  length = 36
FEATURE                 Location/Qualifiers
misc_feature            1..36
                        note = Synthetic
source                  1..36
                        mol_type = other RNA
                        organism = synthetic construct
SEQUENCE: 85
acgaactgcc ctcgtattat ttcgacgcac agacgt                            36

SEQ ID NO: 86           moltype = RNA  length = 34
FEATURE                 Location/Qualifiers
misc_feature            1..34
                        note = Synthetic
source                  1..34
                        mol_type = other RNA
                        organism = synthetic construct
SEQUENCE: 86
acgaactgcc ctctattatt tgacgcacag acgt                              34

SEQ ID NO: 87           moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 87
acgaactgcc ctcgatattt cattttcgac gcacagacgt                        40

SEQ ID NO: 88           moltype = RNA  length = 38
FEATURE                 Location/Qualifiers
misc_feature            1..38
                        note = Synthetic
source                  1..38
                        mol_type = other RNA
                        organism = synthetic construct
SEQUENCE: 88
acgaactgcc ctcgtatttc atttcgacgc acagacgt                          38

SEQ ID NO: 89           moltype = RNA  length = 36
FEATURE                 Location/Qualifiers
misc_feature            1..36
                        note = Synthetic
source                  1..36
                        mol_type = other RNA
                        organism = synthetic construct
SEQUENCE: 89
acgaactgcc ctctatttca tttgacgcac agacgt                            36

SEQ ID NO: 90           moltype = RNA  length = 32
FEATURE                 Location/Qualifiers
misc_feature            1..32
                        note = Synthetic
source                  1..32
                        mol_type = other RNA
                        organism = synthetic construct
SEQUENCE: 90
acgaactgcc ctcttttttg acgcacagac gt                                32

SEQ ID NO: 91           moltype = RNA  length = 34
FEATURE                 Location/Qualifiers
misc_feature            1..34
                        note = Synthetic
source                  1..34
                        mol_type = other RNA
                        organism = synthetic construct
SEQUENCE: 91
acgaactgcc ctcttttttt tgacgcacag acgt                              34

SEQ ID NO: 92           moltype = RNA  length = 34
FEATURE                 Location/Qualifiers
misc_feature            1..34
                        note = Synthetic
```

```
source                  1..34
                        mol_type = other RNA
                        organism = synthetic construct
SEQUENCE: 92
acgaactgcc ctcttttttt tgacgcaccc ccgt                              34

SEQ ID NO: 93           moltype = RNA  length = 34
FEATURE                 Location/Qualifiers
misc_feature            1..34
                        note = Synthetic
source                  1..34
                        mol_type = other RNA
                        organism = synthetic construct
SEQUENCE: 93
acgaactgcc ctcgtttcat cgacgcaccc ccgt                              34

SEQ ID NO: 94           moltype = RNA  length = 32
FEATURE                 Location/Qualifiers
misc_feature            1..32
                        note = Synthetic
source                  1..32
                        mol_type = other RNA
                        organism = synthetic construct
SEQUENCE: 94
acgaactgcc ctctttcatg acgcaccccc gt                                32

SEQ ID NO: 95           moltype = RNA  length = 34
FEATURE                 Location/Qualifiers
misc_feature            1..34
                        note = Synthetic
source                  1..34
                        mol_type = other RNA
                        organism = synthetic construct
SEQUENCE: 95
acgaactgcc ctctattatt tgacgcaccc ccgt                              34

SEQ ID NO: 96           moltype = RNA  length = 36
FEATURE                 Location/Qualifiers
misc_feature            1..36
                        note = Synthetic
source                  1..36
                        mol_type = other RNA
                        organism = synthetic construct
SEQUENCE: 96
acgaactgcc ctctatttca tttgacgcac ccccgt                            36

SEQ ID NO: 97           moltype = RNA  length = 32
FEATURE                 Location/Qualifiers
misc_feature            1..32
                        note = Synthetic
source                  1..32
                        mol_type = other RNA
                        organism = synthetic construct
SEQUENCE: 97
acgaactgcc ctcttttttg acgcaccccc gt                                32

SEQ ID NO: 98           moltype = RNA  length = 26
FEATURE                 Location/Qualifiers
misc_feature            1..26
                        note = Synthetic
misc_feature            13..14
                        note = Site of hexaethylene glycol
source                  1..26
                        mol_type = other RNA
                        organism = synthetic construct
SEQUENCE: 98
acgaactgcc ctcgacgcac agacgt                                       26

SEQ ID NO: 99           moltype = RNA  length = 30
FEATURE                 Location/Qualifiers
misc_feature            1..30
                        note = Synthetic
source                  1..30
                        mol_type = other RNA
                        organism = synthetic construct
SEQUENCE: 99
acgaactgcc ctcgtaagac gcacagacgt                                   30

SEQ ID NO: 100          moltype = RNA  length = 35
```

```
FEATURE                Location/Qualifiers
misc_feature           1..35
                       note = Synthetic
source                 1..35
                       mol_type = other RNA
                       organism = synthetic construct
SEQUENCE: 100
acgaactgcc ctcgtaagac gcacagacgt ttttt                              35

SEQ ID NO: 101         moltype = RNA  length = 30
FEATURE                Location/Qualifiers
misc_feature           1..30
                       note = Synthetic
source                 1..30
                       mol_type = other RNA
                       organism = synthetic construct
SEQUENCE: 101
ccgaactgcc ctcgatcgac gcacagacgg                                    30

SEQ ID NO: 102         moltype = RNA  length = 35
FEATURE                Location/Qualifiers
misc_feature           1..35
                       note = Synthetic
source                 1..35
                       mol_type = other RNA
                       organism = synthetic construct
SEQUENCE: 102
acgaaatgga atcgtaagaa ccacagacgt ttttt                              35

SEQ ID NO: 103         moltype = RNA  length = 15
FEATURE                Location/Qualifiers
misc_feature           1..15
                       note = Synthetic
source                 1..15
                       mol_type = other RNA
                       organism = synthetic construct
SEQUENCE: 103
tcgagggcag ttcgt                                                    15

SEQ ID NO: 104         moltype = RNA  length = 17
FEATURE                Location/Qualifiers
misc_feature           1..17
                       note = Synthetic
source                 1..17
                       mol_type = other RNA
                       organism = synthetic construct
SEQUENCE: 104
gatcgagggc agttcgt                                                  17

SEQ ID NO: 105         moltype = RNA  length = 14
FEATURE                Location/Qualifiers
misc_feature           1..14
                       note = Synthetic
source                 1..14
                       mol_type = other RNA
                       organism = synthetic construct
SEQUENCE: 105
gatcgagggc agtt                                                     14

SEQ ID NO: 106         moltype = RNA  length = 16
FEATURE                Location/Qualifiers
misc_feature           1..16
                       note = Synthetic
source                 1..16
                       mol_type = other RNA
                       organism = synthetic construct
SEQUENCE: 106
tcgatcgagg gcagtt                                                   16

SEQ ID NO: 107         moltype = RNA  length = 17
FEATURE                Location/Qualifiers
misc_feature           1..17
                       note = Synthetic
source                 1..17
                       mol_type = other RNA
                       organism = synthetic construct
SEQUENCE: 107
gtcgatcgag ggcagtt                                                  17
```

```
SEQ ID NO: 108          moltype = RNA  length = 14
FEATURE                 Location/Qualifiers
misc_feature            1..14
                        note = Synthetic
source                  1..14
                        mol_type = other RNA
                        organism = synthetic construct
SEQUENCE: 108
gtcgatcgag ggca                                                       14

SEQ ID NO: 109          moltype = RNA  length = 17
FEATURE                 Location/Qualifiers
misc_feature            1..17
                        note = Synthetic
source                  1..17
                        mol_type = other RNA
                        organism = synthetic construct
SEQUENCE: 109
tgcgtcgatc gagggca                                                    17

SEQ ID NO: 110          moltype = RNA  length = 17
FEATURE                 Location/Qualifiers
misc_feature            1..17
                        note = Synthetic
source                  1..17
                        mol_type = other RNA
                        organism = synthetic construct
SEQUENCE: 110
tgtgcgtcga tcgaggg                                                    17

SEQ ID NO: 111          moltype = RNA  length = 19
FEATURE                 Location/Qualifiers
misc_feature            1..19
                        note = Synthetic
source                  1..19
                        mol_type = other RNA
                        organism = synthetic construct
SEQUENCE: 111
tctgtgcgtc gatcgaggg                                                  19

SEQ ID NO: 112          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 112
tctgtgcgtc gatcga                                                     16

SEQ ID NO: 113          moltype = RNA  length = 14
FEATURE                 Location/Qualifiers
misc_feature            1..14
                        note = Synthetic
source                  1..14
                        mol_type = other RNA
                        organism = synthetic construct
SEQUENCE: 113
tctgtgcgtc gatc                                                       14

SEQ ID NO: 114          moltype = RNA  length = 17
FEATURE                 Location/Qualifiers
misc_feature            1..17
                        note = Synthetic
source                  1..17
                        mol_type = other RNA
                        organism = synthetic construct
SEQUENCE: 114
acgtctgtgc gtcgatc                                                    17

SEQ ID NO: 115          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 115
aatgagggca gttcgt                                                     16
```

```
SEQ ID NO: 116          moltype = RNA  length = 18
FEATURE                 Location/Qualifiers
misc_feature            1..18
                        note = Synthetic
source                  1..18
                        mol_type = other RNA
                        organism = synthetic construct
SEQUENCE: 116
ataatgaggg cagttcgt                                               18

SEQ ID NO: 117          moltype = RNA  length = 13
FEATURE                 Location/Qualifiers
misc_feature            1..13
                        note = Synthetic
source                  1..13
                        mol_type = other RNA
                        organism = synthetic construct
SEQUENCE: 117
aatgagggca gtt                                                    13

SEQ ID NO: 118          moltype = RNA  length = 15
FEATURE                 Location/Qualifiers
misc_feature            1..15
                        note = Synthetic
source                  1..15
                        mol_type = other RNA
                        organism = synthetic construct
SEQUENCE: 118
ataatgaggg cagtt                                                  15

SEQ ID NO: 119          moltype = RNA  length = 18
FEATURE                 Location/Qualifiers
misc_feature            1..18
                        note = Synthetic
source                  1..18
                        mol_type = other RNA
                        organism = synthetic construct
SEQUENCE: 119
tcaataatga gggcagtt                                               18

SEQ ID NO: 120          moltype = RNA  length = 19
FEATURE                 Location/Qualifiers
misc_feature            1..19
                        note = Synthetic
source                  1..19
                        mol_type = other RNA
                        organism = synthetic construct
SEQUENCE: 120
gtcaataatg agggcagtt                                              19

SEQ ID NO: 121          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 121
gtcaataatg agggca                                                 16

SEQ ID NO: 122          moltype = RNA  length = 19
FEATURE                 Location/Qualifiers
misc_feature            1..19
                        note = Synthetic
source                  1..19
                        mol_type = other RNA
                        organism = synthetic construct
SEQUENCE: 122
tgcgtcaata atgagggca                                              19

SEQ ID NO: 123          moltype = RNA  length = 13
FEATURE                 Location/Qualifiers
misc_feature            1..13
                        note = Synthetic
source                  1..13
                        mol_type = other RNA
                        organism = synthetic construct
SEQUENCE: 123
```

```
gtcaataatg agg                                                      13

SEQ ID NO: 124          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 124
tgcgtcaata atgagg                                                   16

SEQ ID NO: 125          moltype = RNA  length = 15
FEATURE                 Location/Qualifiers
misc_feature            1..15
                        note = Synthetic
source                  1..15
                        mol_type = other RNA
                        organism = synthetic construct
SEQUENCE: 125
tctgtgcgtc aataa                                                    15

SEQ ID NO: 126          moltype = RNA  length = 18
FEATURE                 Location/Qualifiers
misc_feature            1..18
                        note = Synthetic
source                  1..18
                        mol_type = other RNA
                        organism = synthetic construct
SEQUENCE: 126
acgtctgtgc gtcaataa                                                 18

SEQ ID NO: 127          moltype = RNA  length = 17
FEATURE                 Location/Qualifiers
misc_feature            1..17
                        note = Synthetic
source                  1..17
                        mol_type = other RNA
                        organism = synthetic construct
SEQUENCE: 127
aatcgagggc agttcgt                                                  17

SEQ ID NO: 128          moltype = RNA  length = 19
FEATURE                 Location/Qualifiers
misc_feature            1..19
                        note = Synthetic
source                  1..19
                        mol_type = other RNA
                        organism = synthetic construct
SEQUENCE: 128
ataatcgagg gcagttcgt                                                19

SEQ ID NO: 129          moltype = RNA  length = 14
FEATURE                 Location/Qualifiers
misc_feature            1..14
                        note = Synthetic
source                  1..14
                        mol_type = other RNA
                        organism = synthetic construct
SEQUENCE: 129
aatcgagggc agtt                                                     14

SEQ ID NO: 130          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 130
ataatcgagg gcagtt                                                   16

SEQ ID NO: 131          moltype = RNA  length = 20
FEATURE                 Location/Qualifiers
misc_feature            1..20
                        note = Synthetic
source                  1..20
                        mol_type = other RNA
                        organism = synthetic construct
```

```
SEQUENCE: 131
tcgaataatc gagggcagtt                                              20

SEQ ID NO: 132          moltype = RNA  length = 21
FEATURE                 Location/Qualifiers
misc_feature            1..21
                        note = Synthetic
source                  1..21
                        mol_type = other RNA
                        organism = synthetic construct
SEQUENCE: 132
gtcgaataat cgagggcagt t                                            21

SEQ ID NO: 133          moltype = RNA  length = 18
FEATURE                 Location/Qualifiers
misc_feature            1..18
                        note = Synthetic
source                  1..18
                        mol_type = other RNA
                        organism = synthetic construct
SEQUENCE: 133
gtcgaataat cgagggca                                                18

SEQ ID NO: 134          moltype = RNA  length = 21
FEATURE                 Location/Qualifiers
misc_feature            1..21
                        note = Synthetic
source                  1..21
                        mol_type = other RNA
                        organism = synthetic construct
SEQUENCE: 134
tgcgtcgaat aatcgagggc a                                            21

SEQ ID NO: 135          moltype = RNA  length = 15
FEATURE                 Location/Qualifiers
misc_feature            1..15
                        note = Synthetic
source                  1..15
                        mol_type = other RNA
                        organism = synthetic construct
SEQUENCE: 135
gtcgaataat cgagg                                                   15

SEQ ID NO: 136          moltype = RNA  length = 18
FEATURE                 Location/Qualifiers
misc_feature            1..18
                        note = Synthetic
source                  1..18
                        mol_type = other RNA
                        organism = synthetic construct
SEQUENCE: 136
tgcgtcgaat aatcgagg                                                18

SEQ ID NO: 137          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 137
tctgtgcgtc gaataa                                                  16

SEQ ID NO: 138          moltype = RNA  length = 19
FEATURE                 Location/Qualifiers
misc_feature            1..19
                        note = Synthetic
source                  1..19
                        mol_type = other RNA
                        organism = synthetic construct
SEQUENCE: 138
acgtctgtgc gtcgaataa                                               19

SEQ ID NO: 139          moltype = RNA  length = 22
FEATURE                 Location/Qualifiers
misc_feature            1..22
                        note = Synthetic
source                  1..22
                        mol_type = other RNA
```

```
                        organism = synthetic construct
SEQUENCE: 139
gatcgagggc agttcgttat gc                                              22

SEQ ID NO: 140          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 140
gatcgagggc agttcgtggg                                                 20

SEQ ID NO: 141          moltype = RNA  length = 22
FEATURE                 Location/Qualifiers
misc_feature            1..22
                        note = Synthetic
source                  1..22
                        mol_type = other RNA
                        organism = synthetic construct
SEQUENCE: 141
gatcgagggc agttcgtggg gg                                              22

SEQ ID NO: 142          moltype = RNA  length = 22
FEATURE                 Location/Qualifiers
misc_feature            1..22
                        note = Synthetic
source                  1..22
                        mol_type = other RNA
                        organism = synthetic construct
SEQUENCE: 142
gatcgagggc agttcgtgtg tg                                              22

SEQ ID NO: 143          moltype = RNA  length = 21
FEATURE                 Location/Qualifiers
misc_feature            1..21
                        note = Synthetic
source                  1..21
                        mol_type = other RNA
                        organism = synthetic construct
SEQUENCE: 143
gatcgagggc agttcgtttt t                                               21

SEQ ID NO: 144          moltype = RNA  length = 23
FEATURE                 Location/Qualifiers
misc_feature            1..23
                        note = Synthetic
source                  1..23
                        mol_type = other RNA
                        organism = synthetic construct
SEQUENCE: 144
gatcgagggc agttcgtttt ggg                                             23

SEQ ID NO: 145          moltype = RNA  length = 22
FEATURE                 Location/Qualifiers
misc_feature            1..22
                        note = Synthetic
source                  1..22
                        mol_type = other RNA
                        organism = synthetic construct
SEQUENCE: 145
aaaaaacgtc tgtgcgtcga tc                                              22

SEQ ID NO: 146          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 146
tttacgtctg tgcgtcgatc                                                 20

SEQ ID NO: 147          moltype = RNA  length = 22
FEATURE                 Location/Qualifiers
misc_feature            1..22
                        note = Synthetic
source                  1..22
```

```
                         mol_type = other RNA
                         organism = synthetic construct
SEQUENCE: 147
tgtgtacgtc tgtgcgtcga tc                                               22

SEQ ID NO: 148           moltype = RNA  length = 22
FEATURE                  Location/Qualifiers
misc_feature             1..22
                         note = Synthetic
source                   1..22
                         mol_type = other RNA
                         organism = synthetic construct
SEQUENCE: 148
cgggtacgtc tgtgcgtcga tc                                               22

SEQ ID NO: 149           moltype = RNA  length = 22
FEATURE                  Location/Qualifiers
misc_feature             1..22
                         note = Synthetic
source                   1..22
                         mol_type = other RNA
                         organism = synthetic construct
SEQUENCE: 149
tttttacgtc tgtgcgtcga tc                                               22

SEQ ID NO: 150           moltype = RNA  length = 22
FEATURE                  Location/Qualifiers
misc_feature             1..22
                         note = Synthetic
source                   1..22
                         mol_type = other RNA
                         organism = synthetic construct
SEQUENCE: 150
cgtgtacgtc tgtgcgtcga tc                                               22

SEQ ID NO: 151           moltype = RNA  length = 16
FEATURE                  Location/Qualifiers
misc_feature             1..16
                         note = Synthetic
source                   1..16
                         mol_type = other RNA
                         organism = synthetic construct
SEQUENCE: 151
gggcagttcg ttatgc                                                      16

SEQ ID NO: 152           moltype = RNA  length = 14
FEATURE                  Location/Qualifiers
misc_feature             1..14
                         note = Synthetic
source                   1..14
                         mol_type = other RNA
                         organism = synthetic construct
SEQUENCE: 152
gggcagttcg tggg                                                        14

SEQ ID NO: 153           moltype = RNA  length = 16
FEATURE                  Location/Qualifiers
misc_feature             1..16
                         note = Synthetic
source                   1..16
                         mol_type = other RNA
                         organism = synthetic construct
SEQUENCE: 153
gggcagttcg tggggg                                                      16

SEQ ID NO: 154           moltype = RNA  length = 16
FEATURE                  Location/Qualifiers
misc_feature             1..16
                         note = Synthetic
source                   1..16
                         mol_type = other RNA
                         organism = synthetic construct
SEQUENCE: 154
gggcagttcg tgtgtg                                                      16

SEQ ID NO: 155           moltype = RNA  length = 15
FEATURE                  Location/Qualifiers
misc_feature             1..15
                         note = Synthetic
```

```
source                  1..15
                        mol_type = other RNA
                        organism = synthetic construct
SEQUENCE: 155
gggcagttcg ttttt                                                              15

SEQ ID NO: 156          moltype = RNA  length = 17
FEATURE                 Location/Qualifiers
misc_feature            1..17
                        note = Synthetic
source                  1..17
                        mol_type = other RNA
                        organism = synthetic construct
SEQUENCE: 156
gggcagttcg ttttggg                                                            17

SEQ ID NO: 157          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 157
aaaaaacgtc tgtgcg                                                             16

SEQ ID NO: 158          moltype = RNA  length = 14
FEATURE                 Location/Qualifiers
misc_feature            1..14
                        note = Synthetic
source                  1..14
                        mol_type = other RNA
                        organism = synthetic construct
SEQUENCE: 158
tttacgtctg tgcg                                                               14

SEQ ID NO: 159          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 159
tgtgtacgtc tgtgcg                                                             16

SEQ ID NO: 160          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 160
cgggtacgtc tgtgcg                                                             16

SEQ ID NO: 161          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 161
tttttacgtc tgtgcg                                                             16

SEQ ID NO: 162          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 162
cgtgtacgtc tgtgcg                                                             16

SEQ ID NO: 163          moltype = RNA  length = 17
FEATURE                 Location/Qualifiers
misc_feature            1..17
```

```
                        note = Synthetic
source                  1..17
                        mol_type = other RNA
                        organism = synthetic construct
SEQUENCE: 163
tctgtgcgtc gatgaaa                                              17

SEQ ID NO: 164          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 164
tctgtgcgtc atgaaa                                               16

SEQ ID NO: 165          moltype = RNA  length = 19
FEATURE                 Location/Qualifiers
misc_feature            1..19
                        note = Synthetic
source                  1..19
                        mol_type = other RNA
                        organism = synthetic construct
SEQUENCE: 165
tctgtgcgtc gaaataata                                            19

SEQ ID NO: 166          moltype = RNA  length = 18
FEATURE                 Location/Qualifiers
misc_feature            1..18
                        note = Synthetic
source                  1..18
                        mol_type = other RNA
                        organism = synthetic construct
SEQUENCE: 166
tctgtgcgtc aaataata                                             18

SEQ ID NO: 167          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 167
tctgtgcgtc aaatgaaata                                           20

SEQ ID NO: 168          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 168
tctgtgcgtc aaaaaa                                               16

SEQ ID NO: 169          moltype = RNA  length = 18
FEATURE                 Location/Qualifiers
misc_feature            1..18
                        note = Synthetic
source                  1..18
                        mol_type = other RNA
                        organism = synthetic construct
SEQUENCE: 169
tctgtgcgtc aaaaaaaa                                             18

SEQ ID NO: 170          moltype = RNA  length = 18
FEATURE                 Location/Qualifiers
misc_feature            1..18
                        note = Synthetic
source                  1..18
                        mol_type = other RNA
                        organism = synthetic construct
SEQUENCE: 170
ggggtgcgtc aaaaaaaa                                             18

SEQ ID NO: 171          moltype = RNA  length = 17
FEATURE                 Location/Qualifiers
```

```
misc_feature          1..17
                      note = Synthetic
source                1..17
                      mol_type = other RNA
                      organism = synthetic construct
SEQUENCE: 171
ggggtgcgtc gatgaaa                                                    17

SEQ ID NO: 172        moltype = RNA  length = 16
FEATURE               Location/Qualifiers
misc_feature          1..16
                      note = Synthetic
source                1..16
                      mol_type = other RNA
                      organism = synthetic construct
SEQUENCE: 172
ggggtgcgtc atgaaa                                                     16

SEQ ID NO: 173        moltype = RNA  length = 18
FEATURE               Location/Qualifiers
misc_feature          1..18
                      note = Synthetic
source                1..18
                      mol_type = other RNA
                      organism = synthetic construct
SEQUENCE: 173
ggggtgcgtc aaataata                                                   18

SEQ ID NO: 174        moltype = RNA  length = 16
FEATURE               Location/Qualifiers
misc_feature          1..16
                      note = Synthetic
source                1..16
                      mol_type = other RNA
                      organism = synthetic construct
SEQUENCE: 174
ggggtgcgtc aaaaaa                                                     16

SEQ ID NO: 175        moltype = RNA  length = 17
FEATURE               Location/Qualifiers
misc_feature          1..17
                      note = Synthetic
source                1..17
                      mol_type = other RNA
                      organism = synthetic construct
SEQUENCE: 175
aaaaaacgtc tgtagtt                                                    17

SEQ ID NO: 176        moltype = RNA  length = 15
FEATURE               Location/Qualifiers
misc_feature          1..15
                      note = Synthetic
source                1..15
                      mol_type = other RNA
                      organism = synthetic construct
SEQUENCE: 176
aaaaaacgtc tggtt                                                      15

SEQ ID NO: 177        moltype = RNA  length = 20
FEATURE               Location/Qualifiers
misc_feature          1..20
                      note = Synthetic
source                1..20
                      mol_type = other RNA
                      organism = synthetic construct
SEQUENCE: 177
aaaaaacgtc tgtagttcgt                                                 20

SEQ ID NO: 178        moltype = RNA  length = 18
FEATURE               Location/Qualifiers
misc_feature          1..18
                      note = Synthetic
source                1..18
                      mol_type = other RNA
                      organism = synthetic construct
SEQUENCE: 178
aaaaaacgtc tggttcgt                                                   18

SEQ ID NO: 179        moltype = RNA  length = 12
```

-continued

```
FEATURE                 Location/Qualifiers
misc_feature            1..12
                        note = Synthetic
source                  1..12
                        mol_type = other RNA
                        organism = synthetic construct
SEQUENCE: 179
tctgtgcgtc ga                                                       12

SEQ ID NO: 180          moltype = RNA  length = 16
FEATURE                 Location/Qualifiers
misc_feature            1..16
                        note = Synthetic
source                  1..16
                        mol_type = other RNA
                        organism = synthetic construct
SEQUENCE: 180
aaaaaacgtc tgtgcg                                                   16
```

VON WILLEBRAND FACTOR (VWF)-TARGETING AGENTS AND METHODS OF USING THE SAME

CROSS-REFERENCE TO RELATED APPLICATIONS

This patent application is a continuation of U.S. patent application Ser. No. 17/146, 147, filed Jan. 11, 2021, which is a divisional application of U.S. patent application Ser. No. 16/334,307, filed on Mar. 18, 2019, and issuing as U.S. Pat. No. 10,889,816, on Jan. 12, 2021, which is a national stage filing under 35 U.S.C. § 371 of International Patent Application No. PCT/US2017/052063, filed Sep. 18, 2017, which application claims the benefit of priority of U.S. Provisional Patent Application No. 62/395,642, filed Sep. 16, 2016, all of which are incorporated herein by reference in their entirety.

STATEMENT REGARDING FEDERALLY SPONSORED RESEARCH

This invention was made with government support under NS080223, and HL112307 awarded by the National Institutes of Health. The government has certain rights in the invention.

SEQUENCE LISTING

This application is being filed electronically via Patent Center and includes an electronically submitted Sequence Listing in .xml format. The .xml file contains a sequence listing entitled "155554.00735.xml" created on Mar. 24, 2024, and is 240,169 bytes in size. The Sequence Listing contained in this .xml file is part of the specification and is hereby incorporated by reference herein in its entirety.

FIELD OF INVENTION

The invention generally relates to compositions and methods for preventing and treating thrombosis. More specifically, the invention relates to Von Willebrand Factor (VWF)-targeting agents and their use in preventing blood clotting (anti-thrombotic activity) and treating and/or reducing formed blood clots (thrombolytic activity).

INTRODUCTION

Thrombosis is a major underlying problem in many cardiovascular and cerebrovascular diseases and is also a major post-surgical complication. Antithromotic drugs have been developed over the past 25 years with the goal of reducing the complications associated with cerebrovascular and cardiovascular disease. However, while reducing thrombotic events in patients, these drugs create a challenge with regard to hemorrhagic risk due to the lack of rapid and predictable reversibility.

Aptamers are single-stranded nucleic acids that adopt specific secondary and tertiary structures based on their sequence which enables specific binding to their target. Aptamers can bind to and inhibit protein targets. They are commonly generated by an in vitro selection process called SELEX (Systematic Evolution of Ligands by EXponential enrichment). See, e.g., Ellington A D, Szostak J W. 1990. In vitro selection of RNA molecules that bind specific ligands, Nature 346:818-22; Tuerk C, Gold L. 1990. Systematic evolution of ligands by exponential enrichment: RNA ligands to bacteriophage T4 DNA polymerase, *Science* 249: 505-10. Aptamers can be systematically isolated to virtually any protein and may undergo extensive molecular modifications to optimize their pharmacokinetics for an intended use. Pegaptanib sodium, developed to treat macular degeneration, was the first aptamer approved for use and other compounds are in development. See, e.g., Wang P, Yang Y, Hong H, Zhang Y, Cai W, Fang D. 2011. Aptamers as therapeutics in cardiovascular diseases. *Curr Med Chem* 18:4169-74. Aptamers offer a promising safer class of anti-thrombotics given that aptamer activity may be rapidly reversed using universal or rationally designed antidotes. See, e.g., Rusconi C P, Scardino E, Layzer J, Pitoc G A, Ortel T L, et al. 2002,RNA aptamers as reversible antagonists of coagulation factor IXa, *Nature* 419:90-4; WO/2008/066621 A3; and WO/2008/121354.

Von Willebrand Factor (VWF) is a promising target for aptamer-based anti-thrombotics. VWF is a multimeric plasma glycoprotein that binds to glycoprotein IbIX, resulting in platelet adhesion—the first non-redundant step in platelet aggregation, resulting in a thrombus. The basic subunit is 260 kDa and is produced in endothelium and platelets. VWF is required for normal hemostatic plug formation and is a carrier protein for factor VIII. Aptamers targeting VWF have been shown to inhibit the formation of blood clots. See, e.g., WO/2008/066621 A3.

There is a need in the art, however, for new VWF-targeting aptamers having increased stability against nuclease degradation, smaller sizes to facilitate chemical synthesis, and increased circulation times in vivo.

SUMMARY

Provided herein are VWF-targeting aptamer compositions and antidote compositions targeting such aptamer compositions as well as methods for preventing and treating blood clots using VWF-targeting agents.

In one aspect, aptamers are provided. The aptamer may include a polynucleotide having at least 50%, 60%, 70%, 80%, 85%, 90%, 95%, 98%, 99%, or 100% sequence identity to SEQ ID NO: 1 and SEQ ID NO: 2, or any one of SEQ ID NOs: 3-102. See Tables 1 and 2 below.

Alternatively, the aptamer may include a polynucleotide having at least 50%, 60%, 70%, 80%, 85%, 90%, 95%, 98%, 99%, or 100% sequence identity to a polynucleotide comprising from 5' to 3' a first stem forming region comprising or consisting of 2, 3, 4, or 5 nucleotides, a first loop region comprising or consisting of the nucleotide sequence AAC, a second stem forming region comprising or consisting of 3, 4, or 5 nucleotides, a second loop region comprising or consisting of the nucleotide sequence CC, a third stem forming region consisting of 2-8 nucleotides, a third loop region consisting of 1-12 nucleotides and/or a spacer sequence, a fourth stem forming region consisting of 2-8 nucleotides and capable of forming a stem with the third stem forming region, a fourth loop region comprising or consisting of the nucleotide C, a fifth stem forming region comprising or consisting of 3, 4, or 5 nucleotides and capable of forming a stem with the second stem forming region, a fifth loop region comprising or consisting the nucleotide sequence CAGA, and a sixth stem forming region comprising or consisting of 2, 3, 4, or 5 nucleotides and capable of forming a stem with the first stem forming region.

In some embodiments, the aptamers described herein may be no more than58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, or 16 nucleotides in length. In some embodiments the polynucleotide comprises unmodified nucleotides. In other embodiments, the polynucleotide comprises a modified form having at least one nucleotide base modification. The nucleotide base modifications include a 2' O-methyl or 2' fluoro modification of the nucleotide.

In some embodiments, the dissociation binding constant of the aptamer for vWF (Kd) is less than 500 nM, less than 100 nM, less than 50 nM, less than 10 nM, less than 5 nM, less than 3 nM, or less than 2 nM.

In another aspect, dimers, trimers, and tetramers including the aptamers described herein are also disclosed.

In another aspect, antidotes to the aptamers described herein are provided. The antidotes may include a polynucleotide having at least 50%, 60%, 70%, 80%, 85%, 90%, 95%, 98%, 99%, or 100%sequence identity to any one of SEQ ID NOs: 103-180 (the nucleotide sequences in Table 3). Alternatively, the antidote may include a polynucleotide having sequence reverse complementary to and capable of hybridizing to at least 8, 9, 10, 11, 12, 13, 14, 15, 16, 17, 18, 19, 20, 21, 22, 23, 24 or more nucleotides of any one of the aptamers described herein.

In a further aspect, pharmaceutical compositions including any of the aptamers or antidotes described herein are provided. The pharmaceutical compositions may include a pharmaceutical carrier, excipient, or diluent (i.e., agents), which are nontoxic to the cell or mammal being exposed thereto at the dosages and concentrations employed.

In another aspect, methods for preventing blood clot formation in a subject are provided. The methods may include administering to the subject any one of the aptamer compositions described herein in a therapeutically effective amount to prevent blood clot formation in the subject.

In a further aspect, methods for treating a blood clot in a subject are also provided. The methods may include administering to the subject a VWF-targeting agent in a therapeutically effective amount to reduce the blood clot in the subject.

BRIEF DESCRIPTION OF THE DRAWINGS

FIG. 2 shows the predicted secondary structures of the VWF9.14T59 (SEQ ID NO: 4) and VWF9.14T79 (SEQ ID NO: 3) aptamers. The T79 aptamer includes the T59 aptamer in addition to a 3' uracil tail to facilitate antidote binding. The dots on the T59 and T79 structures show the location of binding by designed antidotes VWF9.14T59-A011 (AO11; SEQ ID NO: 113) and VWF9.14T79-AO2 (AO55; SEQ ID NO: 157), respectively.

FIG. 12 shows platelet function assay (PFA) results for VWF9.14T59 (SEQ ID NO: 4) with and without antidotes VWF9.14T59-AO3, -AO10, and -AO11 (AO3 (SEQ ID NO: 105), AO10 (SEQ ID NO: 112), and AO11 (SEQ ID NO: 113,respectively). Also shown are PFA results for aptamer VWF9.14T79 (SEQ ID NO: 3) with and without antidotes VWF9.14T79-AO1 (AO43; SEQ ID NO: 145) and VWF9.14T79-AO2 (AO55; SEQ ID NO: 157). Results are shown for aptamer VWF9.14T82 (SEQ ID NO: 78) with and without antidotes VWF9.14T82-AO1 (AO46; SEQ ID NO: 148) and VWF9.14T82-AO2 (AO58; SEQ ID NO: 160). Results are shown for aptamer VWF9.14T84 (SEQ ID NO: 80) with and without antidotes VWF9.14T84-AO1 (AO48; SEQ ID NO: 150) and VWF9.14T84-AO2 (AO60; SEQ ID NO: 162)).

FIG. 15 shows the predicted secondary structures of the T79 vrt7/DTRI-031 (SEQ ID NO: 7) and T59 vrt19 (SEQ ID NO: 4 and Table 2) aptamers and the sequences of the DTRI-006-DTRI-013 aptamers (see Table 2 and SEQ ID NOs: 4, 98, 99, 100, and 101, respectively). DTRI-008 (SEQ ID NO: 4) showed no impact and was comparable to DTRI-006 (SEQ ID NO: 4). DTRI-009 (SEQ ID NO: 98) showed a $K_D$ comparable to DTRI-006 but lower Bmax. DTRI-013 (SEQ ID NO: 101) showed a $K_D$ comparable to DTRI-006 but lower Bmax.

FIG. 16 shows predicted secondary structure and nitrocellulose filter binding assay data for the DTRI-019 (SEQ ID NO: 8) aptamer.

FIG. 20A. Buffer control demonstrated 100% platelet adhesion. Aptamer activity was measured as a percentage of the control. FIG. 20B. 56 nmol/L demonstrated approximately 50% platelet adhesion in this assay while FIG. 20C. 900 nmol/L demonstrated complete inhibition (n=3 per group). FIG. 20D. Aptamer inhibited platelet adhesion in a dose-dependent manner with significant inhibition at doses between 56-900 nmol/L ($p<0.05$) (n=3 per group). FIG. 20E. A linear regression analysis of the dose response curve determined the $\log IC_{50}$ of the aptamer was 1.86 (72.5 nmol/L).

FIGS. 23A-23D show aptamer 9.14T79vrt7/DTRI-031 (SEQ ID NO: 7) demonstrates superior thrombolysis in murine carotid artery occlusion compared to rTPA. FIG. 23A. Aptamer-treated animals at a dose of 0.5 mg/kg (n=8) demonstrated superior thrombolysis compared to both rTPA-treated animals at a dose of 10 mg/kg (n=8) ($p<0.05$) and saline control (n=8) ($p<0.01$). Histopathology of mouse carotid arteries demonstrated that FIG. 23B. aptamer-treated animals had patent vessels free of occlusive thrombus compared to FIG. 23C rTPA animals and FIG. 23D saline control (n=8 per group).

FIGS. 24A-24M show aptamer 9.14T79vrt7/DTRI-031 (SEQ ID NO: 7) prevents platelet adhesion and aggregation in Total Thrombus-formation Analysis System in canine whole blood, recanalizes carotid artery occlusion in canines and demonstrates no brain hemorrhage or embolization. FIG. 24A. Canine whole blood incubated with 9.14T79vrt7 at doses of 12.5 nmol/L, 18.75 nmol/L, 25 nmol/L and 100 nmol/L compared to negative saline control (n=5 per group) ($p<0.05$). FIG. 24B. Still images of whole blood flowing over collagen tubules from the first 10 seconds of each minute. The cloudy patches seen in the control group are aggregated platelets. 9.14T79vrt7 dose was 100 nmol/L. (FIG. 24C-G) After 45 minutes of occlusion, 9.14T79vrt7 administration resulted in recanalization in each of the 3 dogs tested (FIG. 24C -E) compared to FIG. 24F. rTPA or FIG. 24G. Saline control (n=3 per group). FIG. 24H. 9.14T79vrt7 did not cause intracranial hemorrhage nor cerebral thromboembolism compared to FIG. 24I. rTPA or FIG. 24J. control (n=3 per group). Carotid artery histology verified recanalization of the occluded segment in FIG. 24K. 9.14T79vrt7-treated dog compared to FIG. 24L. rTPA and FIG. 24M. control (n=3 per group).

DETAILED DESCRIPTION

Figure 1:
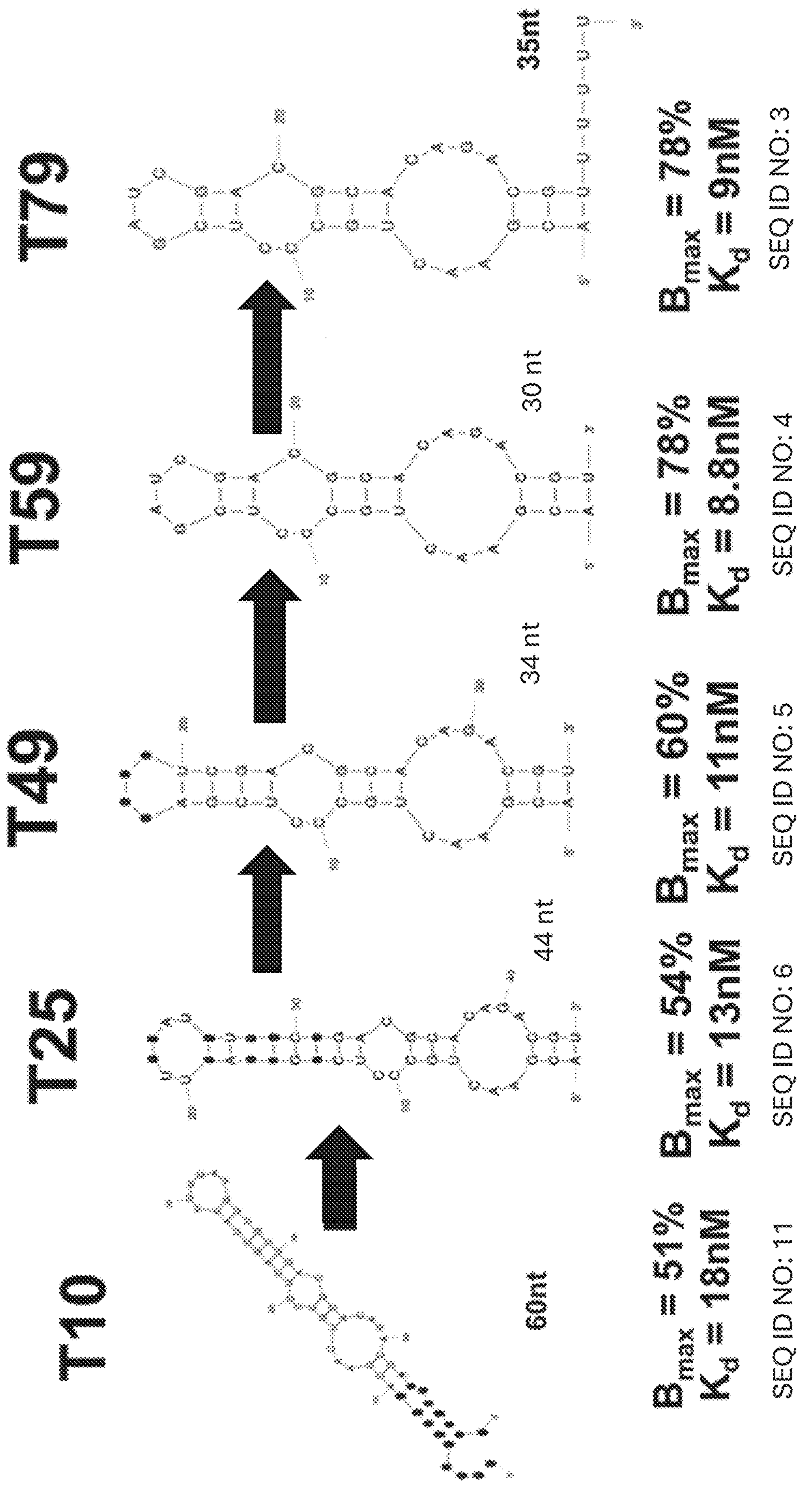
FIG. 1 shows a summary of VWF9.14 truncations T10 (SEQ ID NO: 10), T25 (SEQ ID NO: 6), T49 (SEQ ID NO: 5), T59 (SEQ ID NO: 4), and T79 (SEQ ID NO: 3). In addition to the predicted secondary structures of these aptamers, the length (nt), Kd (nM), and Bmax (%) (as determined by in vitro nitrocellulose filter binding assays) of these aptamers are shown at the bottom of these secondary structures. It was found that the aptamer could be truncated from 60 to 30 nucleotides without a reduction in its ability to bind to VWF. NOTE: Nucleotides highlighted in RED signify major deletions created at each subsequent progressive step. Nucleotides highlighted in Yellow signify a base substitution. VWF aptamer 9.14T79 is T59 with five uracil nucleotides at the 3' end.
Figure 3:
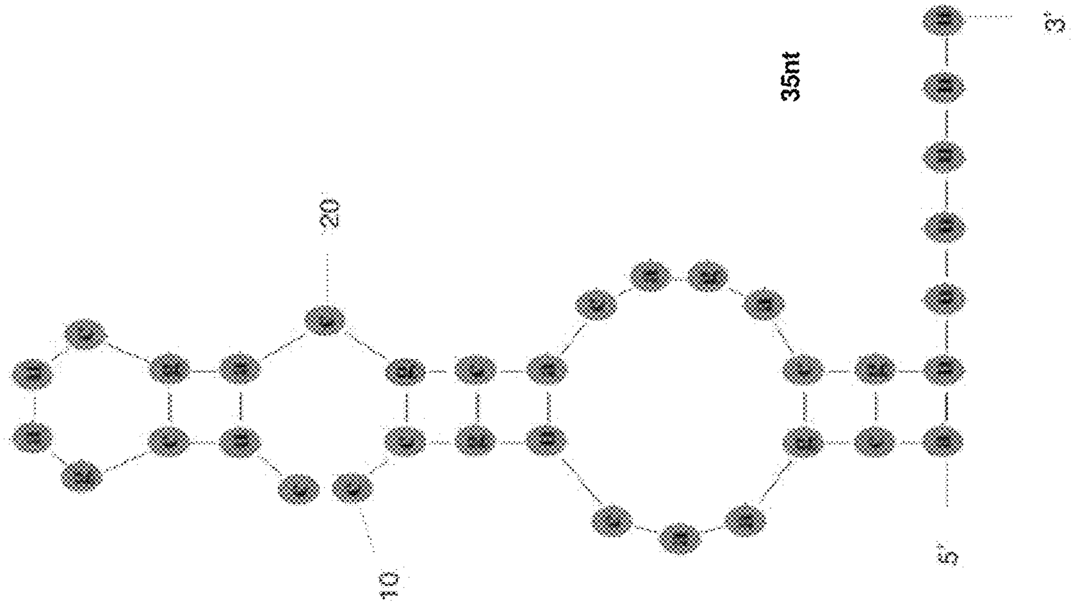
FIG. 3 shows the predicted secondary structure of the optimized VWF aptamer, T79 VRT7 (SEQ ID NO: 7). 2'-O-methyl modified bases are highlighted in red and 2'-fluoro modified bases are highlighted in green; the length (nt), Kd (nM), and Bmax (%) (as determined by in vitro nitrocellulose filter binding assays) of these aptamers are shown at the bottom of these secondary structures.
Figure 4:
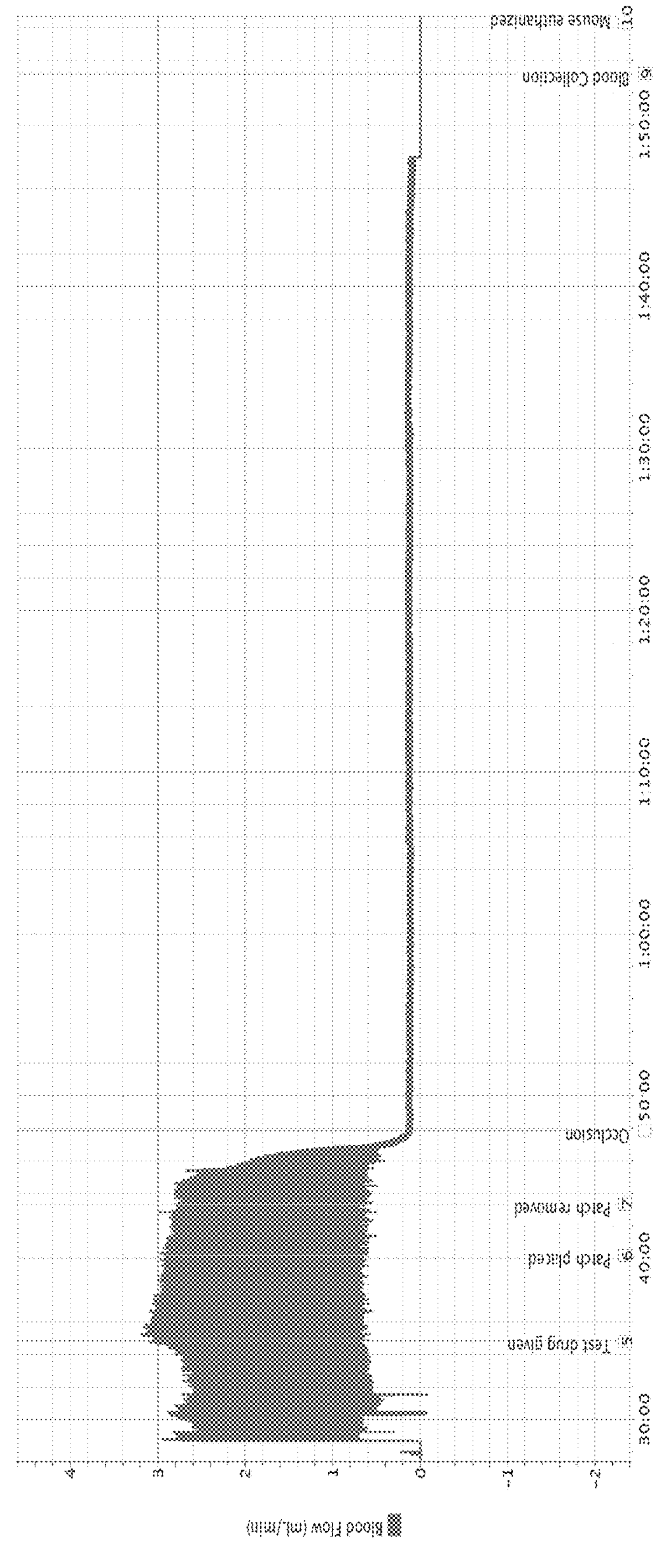
FIG. 4 shows a carotid artery blood flow tracing in a murine arterial thrombosis model experiment injecting a vehicle (no aptamer/negative control) prior to $FeCl_3$ injury. Based on measurements from the flow probe, the vessel was occluded in approximately 4 to 5 minutes following removal of the $FeCl_3$ patch.
Figure 5:
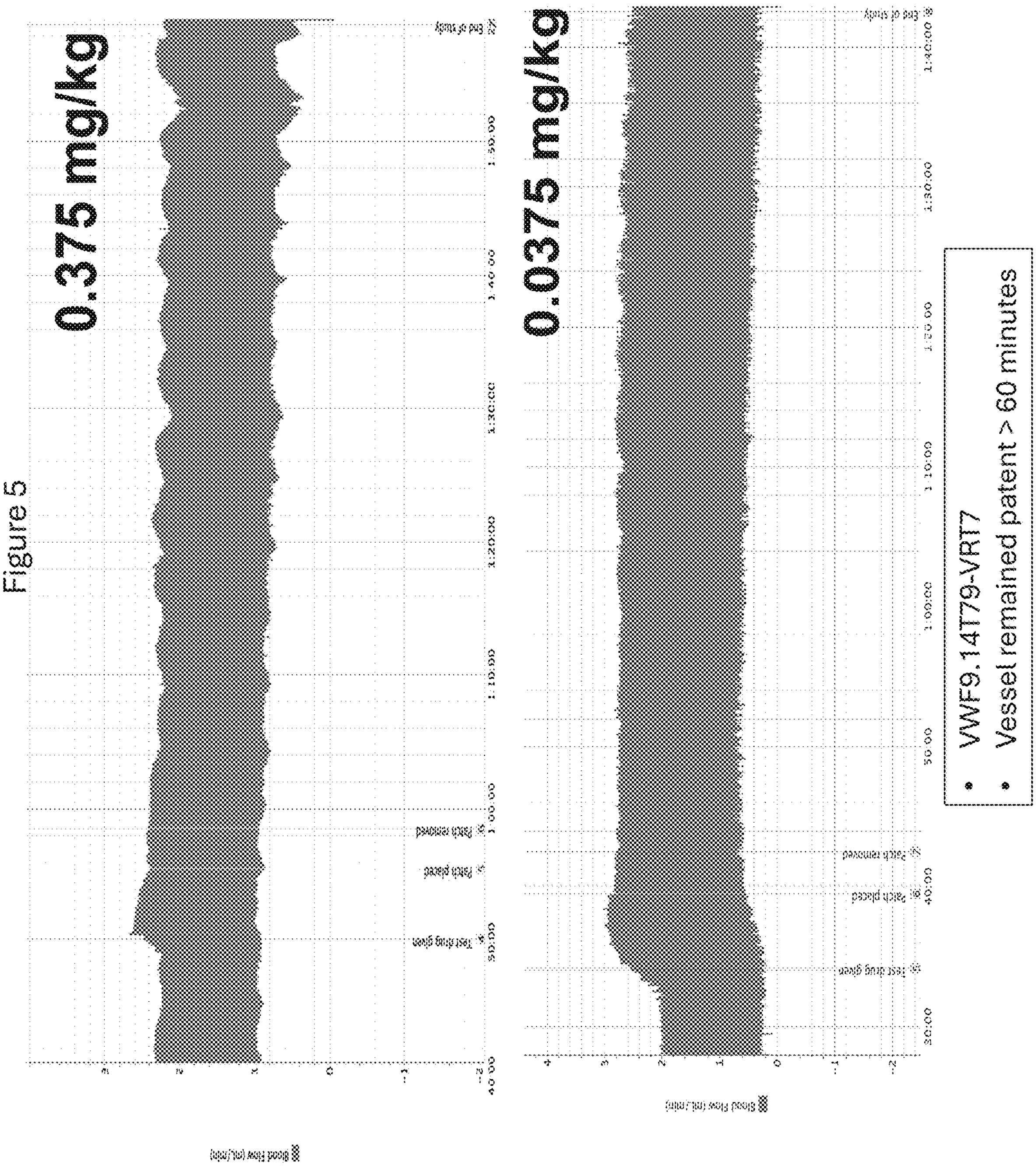
FIG. 5 shows a carotid artery blood flow tracing in two murine arterial thrombosis model experiments injecting the VWF9.14T79-VRT7 aptamer at a dosing of 0.375 mg/kg (top tracing) or 0.0375 mg/kg (bottom tracing) prior to $FeCl_3$ injury. Based on measurements from the flow probe, the vessel remained patent for >60 minutes following removal of the $FeCl_3$ patch.
Figure 6:
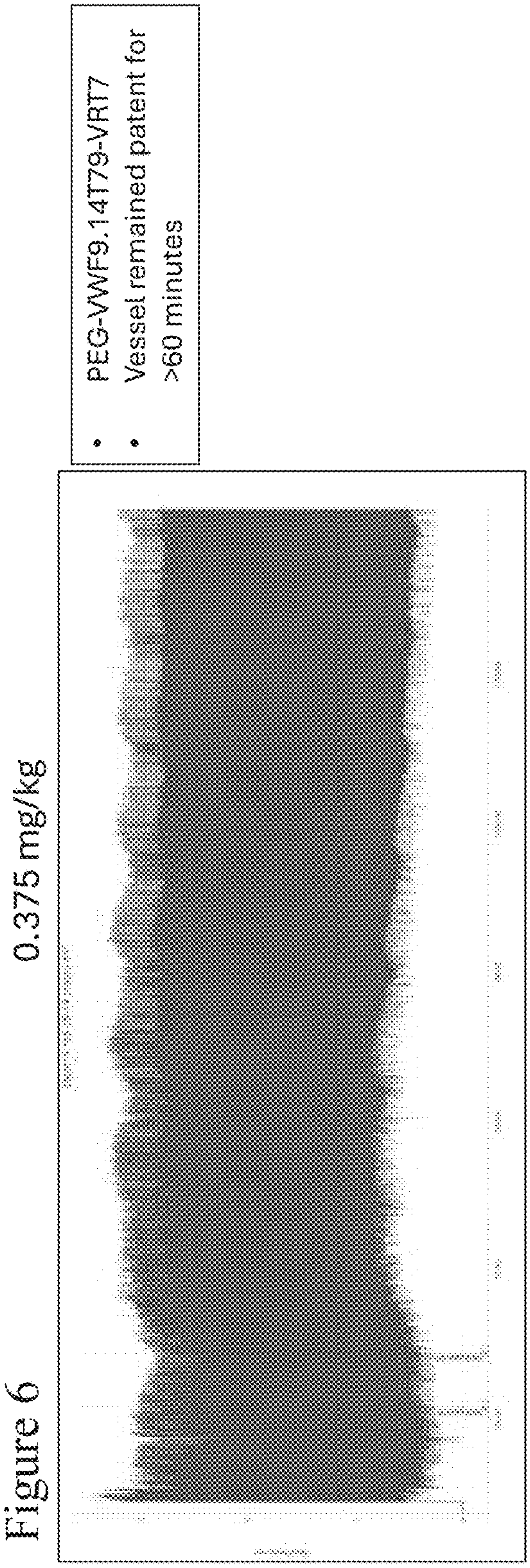
FIG. 6 shows a carotid artery blood flow tracing in a murine arterial thrombosis model experiment injecting the PEG-VWF9.14T79-VRT7 aptamer at a dosing of 0.375 mg/kg prior to $FeCl_3$ injury. Based on measurements from the flow probe, the vessel remained patent for >60 minutes following removal of two 7.5% $FeCl_3$ patches.
Figure 7:
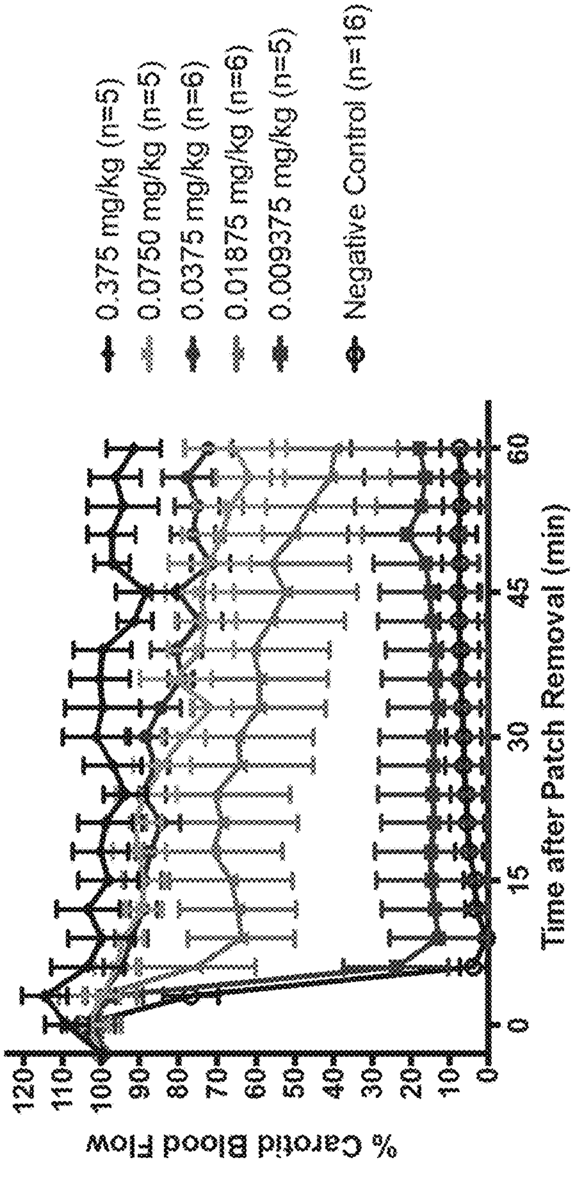
FIG. 7 shows a summary of the percent carotid blood flow in a murine arterial thrombosis model experiment injecting the VWF9.14T79-VRT7 aptamer at various doses (0.009375 mg/kg to 0.375 mg/kg) prior to $FeCl_3$ injury. Negative control is shown for reference. Based on measurements from the flow probe, dosing as low as 0.0375 mg/kg was sufficient to maintain >75% blood flow (compared to blood flow prior to patch placement) for 60 minutes following removal of the $FeCl_3$ patch.

The present disclosure is based, in part, on the inventors' discovery of new optimized reversible VWF-targeting aptamers useful for both preventing (anti-thrombotic activity) and treating (thrombolytic activity) blood clots. Compared to previous VWF-targeting aptamers, the presently disclosed VWF-targeting aptamers have increased stability against nuclease degradation, are smaller in size to facilitate chemical synthesis, and demonstrate increased circulation times in vivo.

Disclosed herein are compositions of aptamers and antidotes as well as methods for preventing and treating blood clots in a subject using VWF-targeting agents such as the newly discovered VWF-targeting aptamers. These compositions and methods may be useful in several applications including, without limitation, prevention or treatment of thrombi (in vitro, in vivo, or ex vivo), or the prevention or treatment of thrombi associated with stroke, cerebrovascular thrombi, deep vein thrombosis (DVT), pulmonary embolism (PE), atrial fibrillation, coronary artery thrombus, intracardiac thrombi, post-surgical thrombi, cancer-induced thrombosis, cancer-related thrombin expression, infection, and disseminated intravascular coagulation (DIC).

Aptamers are provided herein. As used herein, the term "aptamer" refers to single-stranded oligonucleotides that bind specifically to targets molecules with high affinity. Aptamers can be generated against target molecules, such as VWF, by screening combinatorial oligonucleotide libraries for high affinity binding to the target (See, e.g., Ellington and Szostak, Nature 1990; 346: 8 18-22 (1990), Tuerk and Gold, Science 249:505-10 (1990)). The aptamers disclosed herein may be synthesized using methods well-known in the art. For example, the disclosed aptamers may be synthesized using standard oligonucleotide synthesis technology employed by various commercial vendors including Integrated DNA Technologies, Inc. (IDT), Sigma-Aldrich, Life Technologies, or Bio-Synthesis, Inc.

The aptamer may include a polynucleotide having at least 50%, 60%, 70%, 80%, 85%, 90%, 95%, 98%, 99%, or 100%sequence identity to SEQ ID NO: 1 and SEQ ID NO: 2, or any one of SEQ ID NOS: 3-102. The aptamer may include a polynucleotide having at least 70%, 75%, 80%, 85%, 90%, 95%, 98%, 99%, or 100%sequence identity to any one of SEQ ID NOs: 3-6 (nucleotide sequences T25, T49, T59, or T79 in Table 1). In some embodiments, the aptamer includes SEQ ID NO: 7 (T79vrt7 in Table 2), SEQ ID NO: 8 (nucleotide sequence DTRI-019 in Table 2), or SEQ ID NO: 9 (nucleotide sequence DTRI-021 in Table 2).

The terms "polynucleotide," "nucleotide sequence," "polynucleotide sequence," "nucleic acid" and "nucleic acid sequence" refer to a nucleotide, oligonucleotide, polynucleotide (which terms may be used interchangeably), or any fragment thereof. These phrases may refer to DNA or RNA of genomic, natural, or synthetic origin.

Regarding nucleotide sequences, the terms "sequence identity," "percent identity," and " % identity" refer to the percentage of base matches between at least two nucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Sequence identity for a nucleotide sequence may be determined as understood in the art. (See, e.g., U.S. Pat. No. 7,396,664). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known nucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website.

Regarding nucleotide sequences, sequence identity is measured over the length of an entire defined nucleotide sequence, for example, as defined by a particular sequence identified herein. Furthermore, sequence identity, as measured herein, is based on the identity of the nucleotide base in the nucleotide sequence, irrespective of any further modifications to the nucleotide sequence. For example, the nucleotide sequences in the tables described herein may include modifications to the nucleotide sequences such 2'flouro, 2'O-methyl, and inverted deoxythymidine (idT) modifications. These modifications are not considered in determining sequence identity. Thus if a base, for example, is a 2'fluoro adenine (or 2'O-methyl, etc.), it is understood to be an adenine for purposes of determining sequence identity with another sequence. Likewise, the 3' idT modifications to the nucleotide sequences in the tables described herein also are not considered in determining sequence identity.

Alternatively, the aptamer may include a polynucleotide having at least 50%, 60%, 70%, 80%, 85%, 90%, 95%, 98%, 99%, or 100% sequence identity to a polynucleotide comprising from 5' to 3' a first stem forming region comprising or consisting of 2, 3, 4, or 5 nucleotides, a first loop region comprising or consisting of the nucleotide sequence AAC, a second stem forming region comprising or consisting of 3, 4, or 5 nucleotides, a second loop region comprising or consisting of the nucleotide sequence CC, a third stem forming region consisting of 2-8 nucleotides, a third loop region consisting of 1-12 nucleotides or a spacer sequence, a fourth stem forming region consisting of 2-8 nucleotides and capable of forming a stem with the third stem forming region, a fourth loop region comprising or consisting of the nucleotide C, a fifth stem forming region comprising or consisting of 3, 4, or 5 nucleotides and capable of forming a stem with the second stem forming region, a fifth loop region comprising or consisting the nucleotide sequence CAGA, and a sixth stem forming region comprising or consisting of 2, 3, 4, or 5 nucleotides and capable of forming a stem with the first stem forming region. Nonlimiting examples of such aptamers are shown as T25, T49, T59, T59 vrt19, T79, T79 vrt7, or DTRI-019 in FIGS. 1-3 and 15-16.

As used herein, a "spacer sequence" may be any chemical spacer that does not interfere with the binding activity of the aptamer. For example, the spacer sequence may include, without limitation, a hexaethylene glycol spacer (see, e.g., DTRI-009), a C3 spacer, spacer 9, or any other suitable stable linker known to those skilled in the art which would facilitate and maintain the proper folding and secondary structure of the aptamer.

Based on the general aptamer structure presented, for example, in FIGS. 1-3 and 15-16, a person of ordinary skill in the art would readily recognize that several modifications could be made to the sequence while preserving the overall structure and presumably the function of the aptamer. For example, a person of ordinary skill in the art could simply switch the first stem forming region ACG and the sixth stem forming region CGU to UGC and GCA or CCG and CGG (DTRI-013; SEQ ID NO: 101), respectively, and still retain the stem structure of the aptamer. Additionally, modifications to the stem regions could be made that change the bases within the stem region but conserve the overall pyrimidine and purine base composition so that the stem region hybridizes at a similar melting temperature. A person of ordinary skill would also recognize that changes made to the aptamer that disturbed the general aptamer stem loop structure would likely result in an aptamer incapable of efficiently binding its target.

In some embodiments, the aptamer may include a polynucleotide having at least 50%, 60%, 70%, 80%, 85%, 90%, 95%, 99%, or 100% sequence identity to a polynucleotide comprising from 5' to 3' SEQ ID NO: 1 (CGAAC(U/T) GCCC(U/T)C), a variable nucleotide sequence consisting of 1-18 (or any range therein) nucleotides or a spacer sequence, and SEQ ID NO: 2 (GACGCACAGACG).

As used herein, a "variable nucleotide sequence" may be any of the possible nucleotide sequences for a given length. For example, a "variable nucleotide sequence" consisting of 5 nucleotides may include any of the $4^5$ (or 1,025) possible nucleotide sequences having 5 nucleotides.

In some embodiments, the aptamer may be no more than 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, or 16 nucleotides in length.

In some embodiments, the aptamer may have a dissociation constant ($K_D$) for the human VWF protein that is less than 150, 125, 100, 90, 80, 70, 65, 60, 55, 50, 45, 40, 35, 30, 25, 20, 15, 10, 5, 2.5, 2, 1, 0.5, or 0.1 nanomolar (nM). The $K_D$ of an aptamer may be measured using the methodology used by the inventors in the Examples. For example, binding studies using the double-filter nitrocellulose-filter binding assay with the human VWF protein may be performed.

The aptamers may include a polynucleotide (RNA, DNA, or peptide nucleic acid (PNA)) that is in an unmodified form or may be in a modified form including at least one nucleotide base modification. Nucleotide base modifications of polynucleotides to, for example, protect the polynucleotide from nuclease degradation and/or increase the stability of the polynucleotide are well-known in the art. Common nucleotide base modifications that may be used in accordance with the present invention include, without limitation, deoxyribonucleotides, 2'-O-Methyl bases, 2'-Fluoro bases, 2' Amino bases, inverted deoxythymidine bases, 5' modifications, and 3' modifications.

In some embodiments, the aptamer may include a polynucleotide including a modified form including at least one nucleotide base modification selected from the group consisting of a 2'fluoro modification, a 2'O-methyl modification, a 5' modification, and a 3'modification.

Typical 5' modifications may include, without limitation, inverted deoxythymidine bases, addition of a linker sequence such as C6, addition of a cholesterol, addition of a reactive linker sequence which could be conjugated to another moiety such as a PEG. Typical 3' modifications may include, without limitation, inverted deoxythymidine bases, and inverted abasic residues.

In some embodiments, the aptamer may further include a tail nucleotide sequence at the 5' end or the 3' end of the polynucleotide which is not capable of base pairing with 2, 3, 4, 5, 6, 7, 8, 9, 10, 11, 12, 13, 14 or more consecutive nucleotides in the polynucleotide. The tail nucleotide sequence may consist of 2-20 nucleotides or any range therein. As an exemplary tail nucleotide sequence, the present inventors added a 5-nucleotide Uracil (oligo-U tail) to the 3'-end of an aptamer as a potential artificial nucleation site for antidote binding. Thus, in some embodiments, the tail nucleotide sequence may include the nucleotide sequence (U/T)(U/T)(U/T)(U/T)(U/T).

However, it is also contemplated that other nucleotide sequences could serve as tail nucleotide sequences so as that they were not capable of base pairing with 2, 3, 4, 5, 6, 7, 8, 9, 10, 11, 12, 13, 14 or more consecutive nucleotides in the polynucleotide of the aptamer. Additionally, tail nucleotide sequences were also added successfully to the 5' end of the aptamer without significantly affecting the activity of the aptamer.

As additional 5' and/or 3' modifications, the aptamer may include a polynucleotide including a 5' linker and/or a 3' linker. Common 5' and/or 3' linkers for polynucleotides are known in the art and may include peptides, amino acids, nucleic acids, as well as homofunctional linkers or heterofunctional linkers. Particularly useful conjugation reagents that can facilitate formation of a covalent bond with an aptamer may comprise a N-hydroxysuccinimide (NHS) ester and/or a maleimide or using click chemistry. Typical 5' and/or 3' linkers for polynucleotides may include without limitation, amino C3, C4, C5, C6, or C12-linkers.

The aptamer may further include a stability agent. As used herein, a "stability agent" refers to any substance(s) that may increase the stability and/or increase the circulation time of a polynucleotide in vivo. Typical stability agents are known in the art and may include, without limitation, polyethylene glycol (PEG), cholesterol, albumin, or Elastin-like polypeptide.

The aptamer and stability agent may be "linked" either covalently or non-covalently. Additionally, the aptamer and stability agent may be linked using the 5' and/or 3' linkers described herein. The aptamer and stability agent may be linked at the 5' end and/or the 3' end of the aptamer. To link the aptamer and stability agent non-covalently, the aptamer and the stability agent may be linked by a tag system. A "tag system" may include any group of agents capable of binding one another with a high affinity. Several tag systems are well-known in the art and include, without limitation, biotin/avidin, biotin/streptavidin, biotin/NeutrAvidin, or digoxigenin (DIG) systems. In some embodiments, the tag system comprises biotin/avidin or biotin/streptavidin. In such embodiments, the aptamer may be modified at either the 5' or 3' end to include biotin while the stability agent may be modified to include streptavidin or avidin. Alternatively, the aptamer may be modified at either the 5' or 3' end to include streptavidin or avidin while the stability agent may be modified to include biotin.

Dimers, trimers, and tetramers including any one of the aptamers described herein are also provided. A "dimer" refers to the linking together of two aptamer molecules in order to, for example, to increase the stability and/or increase the circulation time of a polynucleotide in vivo. A "trimer" refers to the linking together of three aptamer molecules in order to, for example, to increase the stability and/or increase the circulation time of a polynucleotide in vivo. A "tetramer" refers to the linking together of four aptamer molecules in order to, for example, to increase the stability and/or increase the circulation time of a polynucleotide in vivo. The aptamer molecules may be linked together covalently, noncovalently, or a combination of both. The aptamer molecules may be linked at their 5' or 3' ends. To link the aptamers noncovalently, the aptamers may be linked by a tag system or through a scaffold system.

Antidotes are also provided herein and include a polynucleotide having at least 50%, 60%, 70%, 80%, 85%, 90%, 95%, 98%, 99%, or 100% sequence identity to any one of SEQ ID NOS: 103-180 (the nucleotide sequences in Table 3). Alternatively, the antidote may include a polynucleotide having sequence reverse complementary to and capable of hybridizing to at least 8, 9, 10, 11, 12, 13, 14, 15, 16, 17, 18, 19, 20, 21, 22, 23, 24 or more nucleotides of any one of the aptamers described herein.

Pharmaceutical compositions including any of the aptamers or antidotes described herein are provided. The pharmaceutical compositions may include a pharmaceutical carrier, excipient, or diluent (i.e., agents), which are nontoxic to the cell or mammal being exposed thereto at the dosages and concentrations employed. Often a pharmaceutical agent is in an aqueous pH buffered solution. Examples of pharmaceutical carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant. In some embodiments, the pharmaceutical carrier may include a buffer including about 20 mM Hepes, pH 7.4; 150 mM NaCl; 1 mM $CaCl_2$; 1 mM $MgCl_2$; 5 mM KCl.

Methods for preventing blood clot formation in a subject are provided. The methods may include administering to the subject any one of the aptamer compositions described herein in a therapeutically effective amount to prevent blood clot formation in the subject. “Preventing blood clot formation” may include reducing the likelihood of blood clots, reducing the size of blood clots or slowing further progression of blood clotting.

As used herein, the term “subject” refers to both human and non-human animals. The term “non-human animals” of the disclosure includes all vertebrates, e.g., mammals and non-mammals, such as non-human primates, sheep, dog, cat, horse, cow, mice, chickens, amphibians, reptiles, and the like. In some embodiments, the subject is a human patient.

The subject in need of blood clot prevention may need prevention of blood clots associated with, for example without limitation, stroke, cerebrovascular thrombi, deep vein thrombosis (DVT), pulmonary embolism (PE), atrial fibrillation, coronary artery thrombus, intra-cardiac thrombi, post-surgical thrombi, cancer-induced thrombosis, cancer-related thrombin expression, infection, disseminated intravascular coagulation (DIC), and arterial thrombosis including cerebral arteries, coronary arteries and peripheral arteries in the head and neck, visceral arteries, arms and legs arteries. In some embodiments, the subject in need of blood clot prevention may suffer from atrial fibrillation, or be at risk of having a Deep Vein Thrombosis, a stroke, a heart attack, or a pulmonary embolism.

A therapeutically effective amount or an effective amount as used herein means the amount of a composition that, when administered to a subject for preventing or treating a blood clot is sufficient to effect a treatment (as defined above). The therapeutically effective amount will vary depending on the formulation or composition, the disease and its severity and the age, weight, physical condition and responsiveness of the subject to be treated.

In addition to disclosing methods of preventing blood clots in a subject, the inventors demonstrate that VWF-targeting agents may be used thrombolytically to reduce or “bust” blood clots that have already formed. In the Examples, the inventors demonstrate that one of the disclosed VWF-targeting aptamers, T79vrt7/DTRI-031, was superior to recombinant tissue plasminogen activator (rTPA) in a murine carotid artery occlusion model. These results surprisingly demonstrate that VWF-targeting agents may also be used to treat formed blood clots (thrombolytic activity) as well as being used to prevent blood clot formation (anti-thrombotic activity).

Based on this new use of VWF-targeting agents, methods for treating a blood clot in a subject are also provided. The methods may include administering to the subject a VWF-targeting agent in a therapeutically effective amount to reduce the blood clot in the subject. “Treating a blood clot” or “reducing a blood clot” refers to reducing the size and/or shape of the blood clot so as to allow blood flow to increase at the clot site.

The subject in need of blood clot treatment may need treatment of blood clots associated with, for example without limitation, stroke, cerebrovascular thrombi, deep vein thrombosis (DVT), pulmonary embolism (PE), atrial fibrillation, coronary artery thrombus, intra-cardiac thrombi, post-surgical thrombi, cancer-induced thrombosis, cancer-related thrombin expression, infection, disseminated intravascular coagulation (DIC), and arterial thrombosis including cerebral arteries, coronary arteries and peripheral arteries in the head and neck, visceral arteries, arms and legs arteries. In some embodiments, the subject in need of blood clot treatment suffers from a Deep Vein Thrombosis, a stroke, a heart attack, or a pulmonary embolism.

As used herein, a “VWF-targeting agent” is any agent capable of partially or fully blocking, inhibiting, or neutralizing one or more of the biological activities of a von Willebrand Factor (VWF) protein including, without limitation, a polypeptide, a polynucleotide, or a small molecule. In some embodiments, a VWF-targeting agent may include an agent capable of binding to the A1 domain of a VWF protein and blocking the VWF protein’s binding with a gp1b alpha protein. A VWF-targeting agent may function in a direct or indirect manner. For example, the VWF-targeting agent may directly bind to a VWF protein, thus partially or fully blocking, inhibiting or neutralizing one or more biological activities of the VWF protein, in vitro or in vivo. The VWF-targeting agent may also function indirectly by (1) interacting with (e.g., activating, inducing, blocking or inhibiting) another molecule that can bind to VWF or (2) modulating or affecting the expression (i.e, transcription or translation) of a VWF protein in a cell.

VWF proteins may be any of the VWF proteins found in any mammal including, without limitation, humans or domesticated animals such as dogs, cats, horses, cows, pigs, mice, or rats.

The VWF-targeting agent may be a polypeptide including, without limitation, a peptide or an antibody. As used herein, the term “antibody” is used in the broadest sense used in the art to refer to polypeptide affinity agents based on antibodies. For example, the antibody may include a polyclonal antibody, a monoclonal antibody, a single chain antibody, or antibody fragments such as Fab, Fab', $F(ab')_2$, Fv fragments, diabodies, linear antibodies, nanobodies, or multispecific antibodies formed from antibody fragments.

The antibody may be chimeric, humanized, or fully human. The antibody may be any one of the five known major classes of immunoglobulins including IgA, IgD, IgE, IgG, and IgM. In some embodiments, the VWF-targeting agent may be an anti-VWF antibody that is capable of binding a VWF protein and thereby partially or fully blocking, inhibiting, or neutralizing one or more of the biological activities of the VWF protein. Suitable anti-VWF antibodies include, without limitation, caplacizumab, ALX-0681, or ALX-0081.

Peptides useful as VWF-targeting agents may be identified using techniques well-known in the art such as phage display.

In some embodiments, the VWF-targeting agent may be an aptamer that is capable of binding a VWF protein and thereby partially or fully blocking, inhibiting, or neutralizing one or more of the biological activities of the VWF protein. Suitable VWF aptamers include, without limitation those described in WO/2008/066621 A3 to Sullenger et al. and the aptamers described herein.

The VWF-targeting agent may also be a small molecule. The small molecule may be chemical molecule having a molecular weight below about 2500 Daltons, 2000 Daltons, 1000 Daltons, or 500 Daltons.

The methods of preventing or treating blood clots described herein may further include administering to the subject an antidote in a therapeutically effective amount to neutralize the aptamer or the VWF-targeting agent. "Neutralizing" the aptamer or VWF-targeting agent refers to decreasing either the anti-thrombotic or thrombolytic activity of the aptamer or VWF-targeting agent.

Antidotes that may be used in accordance with the present methods may include sequence-specific antidotes such as the antidotes described herein and those described in WO/2008/066621 A3. The antidotes may also include sequence non-specific antidotes (i.e., cationic polymers) described in, for example, WO/2008/121354.

The compositions (i.e. aptamers, antidotes, and pharmaceutical compositions) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, intralesional, intra-tumoral, intradermal, or transmucosal absorption. Thus the compositions may be formulated as an ingestable, injectable, topical or suppository formulation. Administration of the compositions to a subject may exhibit beneficial effects in a dose-dependent manner. Thus, within broad limits, administration of larger quantities of the compositions is expected to achieve increased beneficial biological effects than administration of smaller amount. Moreover, efficacy is also contemplated at dosages below the level at which toxicity is seen.

It will be appreciated that the specific dosage administered in any given case will be adjusted in accordance with the composition(s) being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol.

The maximal dosage for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will prevent or treat blot clots by at least 10%, 20%, 30%, 40%, 50%, 60%, 70%, 80%, 90%, 100% or more as compared to no treatment.

The compositions described herein may be administered one time or more than one time to the subject to effectively prevent or treat blood clots. Suitable dosage ranges are of the order of several hundred micrograms effective ingredient with a range from about 0.01 to 10 mg/kg/day, preferably in the range from about 0.1 to 1 mg/kg/day. Precise amounts of effective ingredient required to be administered depend on the judgment of the practitioner and may be peculiar to each subject. It will be apparent to those of skill in the art that the therapeutically effective amount of the compositions described herein will depend, inter alia, upon the administration schedule, the unit dose of drug administered, whether the composition is administered in combination with other therapeutic agents, the status and health of the recipient, and the therapeutic activity of the particular composition.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—VWF Aptamer Optimization

Materials and Methods

RNA Aptamer Preparation and Folding

RNA aptamers were synthesized using conventional oligonucleotide synthetic methods in house. Prior to platelet function analysis (PFA) and in vivo models, RNA-based aptamers may be "folded" in an appropriate physiological buffer, e.g. Platelet Binding Buffer (20 mM Hepes, pH 7.4; 150 mM NaCl; 1 mM $CaCl_2$; 1 mM $MgCl_2$; 5 mM KCl). Aptamer solution is heated to 95° C. for 3 minutes, immediately placed on ice for 3 minutes, and then allowed to come to room temperature over approximately 5 to 10 minutes.

Aptamer Binding Assays

Affinity constants ($K_d$ values) were determined using double-filter nitrocellulose filter binding assays (Rusconi et al, Thromb. Haemost. 84:841-848 (2000). All binding studies were performed in binding buffer F (20 mM HEPES, pH 74, 150 mM NaCl, 2 mM $CaCl_2$, and 0.01% BSA) at 37° C. Human purified VWF (factor VIII free) was purchased from Haematologic Technologies Inc (Essex Junction, VT) and used in the double-filter nitrocellulose filter binding assay to determine the $K_d$ of the aptamers. Briefly, RNA were end-labeled at the 5' end with T4 polynucleotide kinase (New England Biolabs, Beverly, MA) and [$\gamma^{32}$P] ATP (Amersham Pharmacia Biotech, Piscataway, NJ) (Fitzwater and Polisky, Methods Enzymol. 267:275-301 (1996)). End-labeled RNA was diluted in binding buffer F. heat denatured at 65° C. for 5 minutes, and subsequently equilibrated at 37° C. Direct binding was performed by incubating trace $^{32}$P-RNA with varying concentrations of VWF protein in binding buffer F at 37° C. for 5 min. The fraction of the nucleic acid-protein complex which bound to the nitrocellulose membrane was quantified with a phosphorimager (Molecular Dynamics, Sunnyvale, CA). Non-specific binding of the radiolabeled nucleic acid was subtracted out of the binding such that only specific binding remained (Wong and Lohman, Proc. Natl. Acad. Sci. USA 90:5428-5432 (1993).

$FeCl_3$—Induced Arterial Thrombosis

A $FeCl_3$ chemical injury model for inducing arterial thrombosis in the mouse is described. The anesthesia was induced with 4 to 5% isoflurane inhaled in a sealed chamber for 5-7 minutes prior to intubation. After gas induction, a single injection of Avertin/tribromoethanol (1.25%, 12.5 mg/ml) was given IP with 27 g ½" needle at a dose between 100-250 mg/kg depending on effect. The total volume ranged from 0.15 to 0.50 cc depending on weight (typically 20-25 g mouse). The animal was returned to the induction chamber for 1-2 more minutes prior to attempting intubation. The mouse was moved to a purpose built intubation stand and intubated with a needleless 20 to 22-gauge catheter. Once intubation was confirmed, the ventral neck was shaved and the mouse transferred to a heated surgery table. While in dorsal recumbency the mouse was immediately connected to a Harvard Apparatus rodent ventilator and maintained with a 70% nitrogen:30% oxygen mix at approximately 90-110 breaths per minute and a tidal volume of ~0.2 ml. Isoflurane was maintained at ~1-3%. Body temperature was maintained at approximately 37° C. with a Physitemp TCAT-2DF.

After ensuring a surgical plane of anesthesia, a midline cervical incision of the skin was made and the fascia was bluntly dissected to expose the right common carotid artery. After exposure and isolation of the right common carotid artery, the left jugular vein was exposed by blunt dissection and three 7-0 silk ligatures placed. A small incision was made with microsurgical scissors, hemostasis maintained with a single 7-0 silk ligature, and a PE-10 polyethylene catheter, or equivalent, was placed in the vein and secured with the two remaining 7-0 silk ligatures. Once catheter patency was confirmed with 0.9% saline, a continuous rate infusion of 0.9% saline was started with a Harvard Apparatus PHD2000 (or equivalent) infusion pump at a rate between 0.5-3 μL/min and maintained until the end of study. A 0.5-PSB transit-time flow probe (Transonic Systems Inc.) was placed around the carotid artery to measure blood flow. Blood flow and temperature measurements were captured with LabChart Software (ADInstruments) throughout the study. Once a normal blood flow (1.0 to 3.0 mL/min) was maintained for at least 5 minutes, antithrombotic test drug, or control, was administered via the jugular catheter in a volume of 100 to 200 μl with a saline based vehicle and given over one minute of time. Aptamer drug doses ranged from 0.005 to 1.0 mg/kg.

Approximately 5 minutes after drug or antidote administration, one or two small pieces of filter paper (1 mm×2 mm) was saturated with 2.5% to 10% $FeCl_3$. These "patches" were then placed on the ventral +/−dorsal aspect of the exposed carotid artery proximal to the flow probe. They were left in place for 3 minutes. After removal of the patches, the respective region of the artery was lightly rinsed with 0.9% saline. Carotid artery blood transit time was then continually measured until the endpoint of the study. The endpoint of the procedure was defined as no more than 60 minutes beyond the formation of a stable thrombus (ie. ~0.0 ml/min carotid artery transit time) or no more than 60 minutes beyond the application of the $FeCl_3$ patches. Once the endpoint was reached, isoflurane was increased to 2-4%.

Two encircling ligatures of 7-0 silk were then placed on the artery proximal to the site of thrombus formation. The flow probe was removed and the artery was transected between the silk ligatures and at a point approximately 5 to 8 mm distal. The artery section was removed for histopathology. The animals were then euthanized by an overdose of anesthetic gas followed by a secondary physical method.

Saphenous Vein Bleeding Model

A saphenous vein bleeding model for evaluating hemostasis in the mouse is described. Anesthesia was induced with 4 to 5% isoflurane inhaled in a sealed chamber for 2-3 minutes. A single injection of Avertin/tribromoethanol (1.25%, 12.5 mg/mL) was given IP with 27 g ½" needle at a dose between 100-250 mg/kg depending on effect. The total volume ranged from 0.15 to 0.50 cc depending on weight (typically 20-25 g mouse). The animal was then returned to the induction chamber for 1-2 more minutes prior to intubation. The mouse was then moved to a purpose built intubation stand and intubated with a needleless 20 to 22-gauge catheter. Once intubation was confirmed, the ventral neck and the medial aspect of both pelvic limbs was shaved and the mouse transferred to a heated surgery table. While in dorsal recumbency the mouse was immediately connected to a Harvard Apparatus rodent ventilator and maintained with a 70%nitrogen:30% oxygen mix at approximately 90-110 breaths per minute and a tidal volume of ~0.2 mL. Isoflurane was maintained at ~1-3%. Body temperature was maintained at approximately 37° C. with a Physitemp TCAT-2DF and rectal probe.

After ensuring a surgical plane of anesthesia, a midline cervical incision of the skin was made. Surgical exposure of the left jugular vein was accomplished by blunt dissection. Once the jugular vein was isolated, a PE-10 polyethylene catheter, or equivalent, was placed in the vein and secured with two encircling 7-0 silk ligatures. Once catheter patency was confirmed with 0.9% saline, a continuous rate infusion of 0.9% saline was started with a Harvard Apparatus PHD2000 (or equivalent) infusion pump at a rate between 0.5-3 μL/min and maintained until the end of study. After catheter placement was complete, the skin on the medial aspect of the left or right pelvic limb was incised to expose a length of the saphenous vascular bundle (saphenous vein and artery, medial saphenous vein). The bundle was maintained under 1-2 drops of 0.9% saline to prevent drying.

Test drug or control was administered IV via the jugular catheter in a volume of 100 to 200 μL with a saline vehicle and given over one minute of time. Aptamer drug doses ranged from 0.005 to 1.0 mg/kg. Approximately 5 to 120 minutes after the test drug was given, the exposed saphenous vein was transected with a 23-26 g needle followed by a ~1 to 2 mm longitudinal incision made in the distal portion of the vessel with micro-dissecting scissors. Extravasated blood was gently wicked away with a tapered mini cotton-tipped applicator until hemostasis occurs. The clot on the distal portion of the vessel was then removed with a 23-26 g needle to restart bleeding. Blood was again wicked away until hemostasis re-occurs. Clot disruption was repeated after every incidence of hemostasis for a total time of 15 to 30 minutes after the initial injury. Injury, clot disruption, hemostasis, and temperature measurements were captured with LabChart Software (ADInstruments) throughout the study. Corresponding antidote molecules were then administered IV via the jugular catheter in a volume of 100 to 200 μL after the test drug. RNA-based oligonucleotide antidotes ranged from 0.005 to 100 mg/kg. Approximately 5 minutes after the administration of the antidote, the clot on the distal portion of the vessel was again removed with a 23-26 g needle to restart bleeding. Blood was wicked away until hemostasis re-occurs. Clot disruption was repeated after every incidence of hemostasis for a total time of 15 to 30 minutes. Once the endpoint was reached, ~0.5 mL of blood was collected via cardiac puncture or withdrawn from the caudal vena cava. The animal was then euthanized by an overdose of anesthetic gas followed by a secondary physical method.

PFA100 Protocol

Platelet Function Analyzer, PFA-100 (Dade Behring, Deerfield, IL) provides a quantitative measure of platelet function in anti-coagulated whole blood (Ortel et al, Thromb. Haemost. 84:93-97 (2000)). Briefly, aptamers were diluted in an appropriate buffer (i.e. 150 mM NaCl: 20 mM HEPES pH 7.4; 5 mM KCl, 1 mM $MgCl_2$ and 1 mM $CaCl_2$ or 150 mM NaCl; 20mM HEPES pH: 7.4: 2 mM $CaCl_2$; or PBS) and heat denatured. Aptamers were added to fresh whole blood at the final concentration indicated; incubated at RT for 3-5 minutes and then run utilizing a collagen/ADP test cartridge in a PFA-100. The maximum closing time of the PFA-100 is 300 seconds Antidote activity of aptamer was measured by mixing whole blood with aptamer in buffer followed by administration of antidote and measuring in PFA.

Results

VWF9.14 Variants

To optimize the VWF9.14 aptamer, we generated several VWF9.14 aptamer truncation variants and several VWF9.14 aptamer modification variants. See, e.g., FIGS. 1-3. The VWF9.14 aptamer truncation variants are listed in Table 1 below.

TABLE 1

Truncated Aptamers

| ID | Length | Sequence | Bmax (%) | Kd (nM) | SEQ ID NO: |
|---|---|---|---|---|---|
| Apt. 9-14 | 80 nt | GGGAGGACGAUGCGGUGGACGAACUGCCCUCAGCUACUUUCAUGUUGCUGACGCACAGACGACUCGCUGAGGAUCCGAGA | 70 | 12.0 | 10 |
| T10 | 60 nt | GGGAGGUGGACGAACUGCCCUCAGCUACUUUCAUGUUGCUGACGCACAGACGACUCGCUG-idT | 51 | 18.4 | 11 |
| T11 | 57 nt | GGGAGGACGAACUGCCCUCAGCUACUUUCAUGUUGCUGACGCACAGACGACUCGCUG | 54 | 16.5 | 12 |
| T12 | 54 nt | GGGAGGAACUGCCCUCAGCUACUUUCAUGUUGCUGACGCACAGACGACUCGCUG | NB | NB | 13 |
| T13 | 51 nt | GGGAGGUGCCCUCAGCUACUUUCAUGUUGCUGACGCACAGACGACUCGCUG | NB | NB | 14 |
| T14 | 28 nt | GGGAGGUCAGCUACUUUCAUGUUGCUGA | NB | NB | 15 |
| T15 | 57 nt | GGGAGGUGGACGAACUGCCCUCAGCUACCAUGUUGCUGACGCACAGACGACUCGCUG | 13 | 83.0 | 16 |
| T16 | 54 nt | GGGAGGUGGACGAACUGCCCUCAGCUACGUUGCUGACGCACAGACGACUCGCUG | 13 | 126.0 | 17 |
| T17 | 40 nt | GGGAGGUGGACGAACUGCCCUACGCACAGACGACUCGCUG | NB | NB | 18 |

TABLE 1-continued

| Truncated Aptamers | | | | | |
|---|---|---|---|---|---|
| ID | Length | Sequence | Bmax (%) | Kd (nM) | SEQ ID NO: |
| T18 | 57 nt | GGGAGGUGGACGAACUGCCCUCUACUUUCAUGUUGCUGACGCACAGACGACUCGCUG | NB | NB | 19 |
| T19 | 54 nt | GGGAGGUGGACGAACUGCCCUCUUUCAUGUUGCUGACGCACAGACGACUCGCUG | NB | NB | 20 |
| T20 | 54 nt | GGGAGGUGGACGAACUGCCCUCUACUUUCAUGUUGACGCACAGACGACUCGCUG | NB | NB | 21 |
| T21 | 46 nt | GGGAGGUCAGCUACUUUCAUGUUGCUGACGCACAGACGACUCGCUG | 10 | 26.0 | 22 |
| T22 | 53 nt | GGACGAACUGCCCUCAGCUACUUUCAUGUUGCUGACGCACAGACGACUCGCUG | 43 | 28.0 | 23 |
| T23 | 51 nt | ACGAACUGCCCUCAGCUACUUUCAUGUUGCUGACGCACAGACGACUCGCUG-idT | ND | ND | 24 |
| T24 | 48 nt | GGACGAACUGCCCUCAGCUACUUUCAUGUUGCUGACGCACAGACGUCC-idT | ND | ND | 25 |
| T25 | 44 nt | ACGAACUGCCCUCAGCUACUUUCAUGUUGCUGACGCACAGACGU-idT | 54 | 13.4 | 6 |
| T26 | 44 nt | CCGAACUGCCCUCAGCUACUUUCAUGUUGCUGACGCACAGACGG-idT | ND | ND | 26 |
| T27 | 55 nt | GGGAGGACGAACUGCCCUCAGCUACUUAUGUUGCUGACGCACAGACGACUCGCUG-idT | ND | ND | 27 |
| T28 | 56 nt | GGGAGGACGAACUGCCCUCAGCUACUUCAUGUUGCUGACGCACAGACGACUCGCUG-idT | ND | ND | 28 |
| T29 | 53 nt | GGGAGGACGAACUGCCCUCAGCUAUUAUUAGCUGACGCACAGACGACUCGCUG-idT | ND | ND | 29 |
| T30 | 40 nt | CCGAACUGCCCUCAGCUAUUAUUAGCUGACGCACAGACGG-idT | 21 | 39.3 | 30 |
| T31 | 44 nt | GGGAACUGCCCUCAGCUACUUUCAUGUUGCUGACGCACAGACCC-idT | ND | ND | 31 |
| T32 | 48 nt | GGACGAACUGCCCUCAGCUACUUUCAUGUUGCUGACGCACAGACGACU-idT | ND | ND | 32 |
| T33 | 42 nt | ACGAACUGCCCUCAGCACUUUCAUGUGCUGACGCACAGACGU-idT | 66 | 15.0 | 33 |
| T34 | 42 nt | ACGAACUGCCCUCGCUACUUUCAUGUUGCGACGCACAGACGU-idT | 61 | 10.0 | 34 |
| T35 | 42 nt | ACGAACUGCCCUCAGUACUUUCAUGUUCUGACGCACAGACGU-idT | 66 | 12.0 | 35 |
| T36 | 42 nt | ACGAACUGCCCUCAGCUAUUUCAUUUGCUGACGCACAGACGU-idT | 58 | 11.0 | 36 |
| T37 | 42 nt | ACGAACUGCCCUCAGCUACUUAUGUUGCUGACGCACAGACGU-idT | 68 | 10.0 | 37 |
| T38 | 40 nt | ACGAACUGCCCUCGCACUUUCAUGUGCGACGCACAGACGU-idT | 55 | 9.6 | 38 |
| T39 | 40 nt | ACGAACUGCCCUCAGACUUUCAUGUCUGACGCACAGACGU-idT | 50 | 11.0 | 39 |
| T40 | 40 nt | ACGAACUGCCCUCAGCAUUUCAUUGCUGACGCACAGACGU-idT | 54 | 11.0 | 40 |
| T41 | 40 nt | ACGAACUGCCCUCAGCACUUAUGUGCUGACGCACAGACGU-idT | 49 | 8.6 | 41 |
| T42 | 40 nt | ACGAACUGCCCUCGUACUUUCAUGUUCGACGCACAGACGU-idT | ND | ND | 42 |
| T43 | 40 nt | ACGAACUGCCCUCGCUAUUUCAUUUGCGACGCACAGACGU-idT | ND | ND | 43 |
| T44 | 40 nt | ACGAACUGCCCUCGCUACUUAUGUUGCGACGCACAGACGU-idT | ND | ND | 44 |
| T45 | 40 nt | ACGAACUGCCCUCAGUAUUUCAUUUCUGACGCACAGACGU-idT | ND | ND | 45 |
| T46 | 40 nt | ACGAACUGCCCUCAGUACUUAUGUUCUGACGCACAGACGU-idT | ND | ND | 46 |
| T47 | 40 nt | ACGAACUGCCCUCAGCUAUUAUUUGCUGACGCACAGACGU-idT | ND | ND | 47 |
| T48 | 36 nt | ACGAACUGCCCUCGACUUAUGUCGACGCACAGACGU-idT | 52 | 12.0 | 48 |
| T49 | 34 nt | ACGAACUGCCCUCGAUUAUUCGACGCACAGACGU-idT | 60 | 10.5 | 5 |
| T50 | 38 nt | ACGAACUGCCCUCGCACUUAUGUGCGACGCACAGACGU-idT | 61 | 9.6 | 49 |
| T51 | 38 nt | ACGAACUGCCCUCAGACUUAUGUCUGACGCACAGACGU-idT | 56 | 17.0 | 50 |
| T52 | 38 nt | ACGAACUGCCCUCAGCAUUAUUGCUGACGCACAGACGU-idT | 58 | 16.0 | 51 |
| T53 | 43 nt | ACGAACUGCCCUCAGCUACUUUCAUGUUGCUGACGCACAACGU-idT | NB | NB | 52 |
| T54 | 43 nt | ACGAACUGCCCUCAGCUACUUUCAUGUUGCUGACGCACGACGU-idT | NB | NB | 53 |
| T55 | 41 nt | ACGACUGCCCUCAGCUACUUUCAUGUUGCUGACGCACACGU-idT | NB | NB | 54 |
| T56 | 24 nt | ACGAACUGCCCUACGCACAGACGU-idT | NB | NB | 55 |
| T57 | 26 nt | ACGAACUGCCCUCGACGCACAGACGU-idT | NB | NB | 56 |
| T58 | 28 nt | ACGAACUGCCCUCGCGACGCACAGACGU-idT | NB | NB | 57 |

TABLE 1-continued

Truncated Aptamers

| ID | Length | Sequence | Bmax (%) | Kd (nM) | SEQ ID NO: |
|---|---|---|---|---|---|
| T59 | 30 nt | ACGAACUGCCCUCGAUCGACGC ACAGACGU-idT | 78 | 8.8 | 4 |
| T60 | 32 nt | ACGAACUGCCCUCGAUUUCGAC GCACAGACGU-idT | 71 | 12.5 | 58 |
| T61 | 22 nt | ACGAACUGCCCCGCACAGACG U-idT | NB | NB | 59 |
| T62 | 32 nt | ACGAACUCCCUCGAUUAUUCGA CGACAGACGU-idT | NB | NB | 60 |
| T63 | 32 nt | ACGAACGCCCUCGAUUAUUCGA CGCACGACGU-idT | 10 | 83.0 | 61 |
| T64 | 30 nt | ACGAACUGCCCUAUUAUUACGC ACAGACGU-idT | 13 | 54.0 | 62 |
| T65 | 28 nt | ACGAACUGCCCUUUAUACGCAC AGACGU-idT | NB | NB | 63 |
| T66 | 31 nt | ACGAACUGCUCGAUUAUUCGAG CACAGACGU-idT | NB | NB | 64 |
| T67 | 33 nt | ACGAACUGCCCUCGAUUAUUCG ACCACAGACGU-idT | NB | NB | 65 |
| T68 | 30 nt | ACGAACUGCCCUCUUAUGACGC ACAGACGU-idT | 82 | 16.0 | 66 |
| T69 | 32 nt | ACGAACUGCCCUGAUUAUUCAC GCACAGACGU-idT | 52 | 26.0 | 67 |
| T70 | 32 nt | ACGAACUGCCCUCAUUAUUGAC GCACAGACGU-idT | 81 | 13.0 | 68 |
| T71 | 32 nt | ACGAACUGCCCUCGUUAUCGAC GCACAGACGU-idT | 77 | 10.0 | 69 |
| T73 | 35 nt | GCAUAACGAACUGCCCUCGAUC GACGCACAGACGU-idT | ND | ND | 70 |
| T74 | 33 nt | CCCACGAACUGCCCUCGAUCGA CGCACAGACGU-idT | 37 | 23.0 | 71 |
| T75 | 35 nt | CCCCCACGAACUGCCCUCGAUC GACGCACAGACGU-idT | ND | ND | 72 |
| T76 | 35 nt | CACACACGAACUGCCCUCGAUC GACGCACAGACGU-idT | ND | ND | 73 |
| T77 | 34 nt | AAAAACGAACUGCCCUCGAUCG ACGCACAGACGU-idT | 59 | 8.8 | 74 |
| T78 | 36 nt | CCCAAAACGAACUGCCCUCGAU CGACGCACAGACGU-idT | 55 | 6.6 | 75 |
| T79 | 35 nt | ACGAACUGCCCUCGAUCGACGC ACAGACGUUUUUU-idT | 64 | 1.6 | 3 |
| T80 | 33 nt | ACGAACUGCCCUCGAUCGACGC ACAGACGUAAA-idT | 77 | 6.3 | 76 |
| T81 | 35 nt | ACGAACUGCCCUCGAUCGACGC ACAGACGUACACA-idT | 63 | 4.2 | 77 |
| T82 | 35 nt | ACGAACUGCCCUCGAUCGACGC ACAGACGUACCCG-idT | 76 | 5.3 | 78 |
| T83 | 35 nt | ACGAACUGCCCUCGAUCGACGC ACAGACGUAAAAA-idT | 61 | 3.5 | 79 |

TABLE 1-continued

Truncated Aptamers

| ID | Length | Sequence | Bmax (%) | Kd (nM) | SEQ ID NO: |
|---|---|---|---|---|---|
| T84 | 35 nt | ACGAACUGCCCUCGAUCGACGC ACAGACGUACACG-idT | 76 | 3.7 | 80 |
| T85 | 36 nt | ACGAACUGCCCUCGAUUUCAUU CGACGCACAGACGU-idT | ND | ND | 81 |
| T86 | 34 nt | ACGAACUGCCCUCGUUUCAUCG ACGCACAGACGU-idT | 88 | 16.0 | 82 |
| T87 | 32 nt | ACGAACUGCCCUCUUUCAUGAC GCACAGACGU-idT | 86 | 11.0 | 83 |
| T88 | 38 nt | ACGAACUGCCCUCGAUAUUAUU UUCGACGCACAGACGU-idT | ND | ND | 84 |
| T89 | 36 nt | ACGAACUGCCCUCGUAUUAUUU CGACGCACAGACGU-idT | 79 | 12.0 | 85 |
| T90 | 34 nt | ACGAACUGCCCUCUAUUAUUUG ACGCACAGACGU-idT | 77 | 3.8 | 86 |
| T91 | 40 nt | ACGAACUGCCCUCGAUAUUUCA UUUUCGACGCACAGACGU-idT | ND | ND | 87 |
| T92 | 38 nt | ACGAACUGCCCUCGUAUUUCAU UUCGACGCACAGACGU-idT | ND | ND | 88 |
| T93 | 36 nt | ACGAACUGCCCUCUAUUUCAUU UGACGCACAGACGU-idT | 76 | 6.4 | 89 |
| T94 | 32 nt | ACGAACUGCCCUCUUUUUUGAC GGCACAGACU-idT | 87 | 5.0 | 90 |
| T95 | 34 nt | ACGAACUGCCCUCUUUUUUUUG ACGCACAGACGU-idT | 81 | 12.0 | 91 |
| T96 | 34 nt | ACGAACUGCCCUCUUUUUUUUG ACGCACCCCCGU-idT | NB | NB | 92 |
| T97 | 34 nt | ACGAACUGCCCUCGUUUCAUCG ACGCACCCCCGU-idT | NB | NB | 93 |
| T98 | 32 nt | ACGAACUGCCCUCUUUCAUGAC GCACCCCCGU-idT | NB | NB | 94 |
| T99 | 34 nt | ACGAACUGCCCUCUAUUAUUUG CACGCACCCCGU-idT | NB | NB | 95 |
| T100 | 36 nt | ACGAACUGCCCUCUAUUUCAUU UGACGCACCCCCGU-idT | ND | ND | 96 |
| T101 | 32 nt | ACGAACUGCCCUCUUUUUUGAC GCACCCCCGU-idT | NB | NB | 97 |

A = 2'OH adenine;
C = 2'fluorocytosine;
G = 2'OH guanine;
U = 2'flourouracil
idT = inverted deoxythymidine on 3' end (Sequence lengths and SEQ ID NOs: below do not include the idT)
NB = No Binding;
ND = Not Determined The VWF9.14 aptamer modification variants created are listed in Table 2 below.

TABLE 2

Modified Versions of VWF9.14 Aptamer Truncates

| ID | Length | Modified Sequence | Bmax (%) | Kd (nM) | SEQ ID NO: |
|---|---|---|---|---|---|
| T25 vrt1 | 44 nt | mAfCmGmAmAfCfUmGfCfCfCfUfCmAmGfC fUmAfCfUfUfUfCmAfUmGfUfUmGfCfUmGm AfCmGfCmAfCmAmGmAfCmGfU-idT | NB | NB | 6 |
| T25 vrt2 | 44 nt | mAmCmGmAmAmCmUmGmCmCmCmUmC mAmGmCmUmAmCmUmUmUmCmAmUmG mUmUmGmCmUmGmAmCmGmCmAmCmA mGmAmCmGmU-idT | NB | NB | 6 |
| T25 vrt3 | 44 nt | mAfCmGrArAfCfUrGfCfCfCfUfCrArGfCfUrA fCfUfUfUfCrAfUrGfUfUrGfCfUrGrAfCrGfCr AfCrArGrAfCmGfU-idT | 38 | 9.2 | 6 |
| T25 vrt4 | 44 nt | mAmCmGrArAfCfUrGfCfCfCfUfCrArGfCfUr AfCfUfUfUfCrAfUrGfUfUrGfCfUrGrAfCrGfC rAfCrArGrAmCmGmU-idT | 33 | 5.9 | 6 |
| T25 vrt5 | 44 nt | rAfCrGmAmAfCfUrGfCfCfCfUfCrArGfCfUrA fCfUfUfUfCrAfUrGfUfUrGfCfUrGrAfCrGfCr AfCmAmGmAfCrGfU-idT | 58 | 7.1 | 6 |
| T25 vrt6 | 44 nt | rAfCrGmAmAmCfUrGfCfCfCfUfCrArGfCfUr AfCfUfUfUfCrAfUrGfUfUrGfCfUrGrAfCrGfC rAmCmAmGmAfCrGfU-idT | 67 | 3.1 | 6 |
| T25 vrt7 | 44 nt | rAfCrGrArAfCfUmGfCfCfCfUfCrArGfCfUrAf CfUfUfUfCrAfUrGfUfUrGfCfUrGmAfCmGfC mAfCrArGrAfCrGfU-idT | NB | NB | 6 |
| T25 vrt8 | 44 nt | rAfCrGrArAfCmUmGmCmCmCmUfCrArGfCf UrAfCfUfUfUfCrAfUrGfUfUrGfCfUrGmAmC mGmCmAfCrArGrAfCrGfU-idT | NB | NB | 6 |
| T25 vrt9 | 44 nt | rAfCrGrArAfCfUrGfCfCfCfUfCmAmGfCfUm AfCfUfUfUfCrAfUrGfUfUmGfCfUmGrAfCrGf CrAfCrArGrAfCrGfU-idT | 57 | 9.8 | 6 |
| T25 vrt10 | 44 nt | rAfCrGrArAfCfUrGfCfCfCfUmCmAmGmCm UmAfCfUfUfUfCrAfUrGmUmUmGmCmUmG rAfCrGfCrAfCrArGrAfCrGfU-idT | 62 | 5.7 | 6 |
| T25 vrt11 | 44 nt | rAfCrGrArAfCfUrGfCfCfCfUfCrArGfCfUrAfC fUfUfUfCmAfUmGfUfUrGfCfUrGrAfCrGfCrA fCrArGrAfCrGfU-idT | 57 | 7.2 | 6 |
| T25 vrt12 | 44 nt | rAfCrGrArAfCfUrGfCfCfCfUfCrArGfCfUrAm CmUmUmUmCmAmUmGfUfUrGfCfUrGrAfC rGfCrAfCrArGrAfCrGfU-idT | 59 | 7.1 | 6 |
| T25 vrt13 | 44 nt | rAfCrGmAmAmCfUrGfCfCfCfUmCmAmGmC mUmAmCmUmUmUmCmAmUmGmUmUmG mCmUmGrAfCrGfCrAmCmAmGmAfCrGfU- idT | 79 | 1.9 | 6 |
| T25 vrt14 | 44 nt | mAfCrGrArAfCfUrGfCfCfCfUfCrArGfCfUrAf CfUfUfUfCrAfUrGfUfUrGfCfUrGrAfCrGfCrA fCrArGrAfCrGmU-idT | 54 | 9.2 | 6 |
| T25 vrt15 | 44 nt | rAmCrGrArAfCfUrGfCfCfCfUfCrArGfCfUrAf CfUfUfUfCrAfUrGfUfUrGfCfUrGrAfCrGfCrA fCrArGrAfCmGfU-idT | 73 | 7.3 | 6 |
| T25 vrt16 | 44 nt | rAfCmGrArAfCfUrGfCfCfCfUfCrArGfCfUrAf CfUfUfUfCrAfUrGfUfUrGfCfUrGrAfCrGfCrA fCrArGrAmCrGfU-idT | 78 | 4.3 | 6 |
| T25 vrt17 | 44 nt | rAfCrGrArAfCmUrGfCfCfCfUfCrArGfCfUrAf CfUfUfUfCrAfUrGfUfUrGfCfUrGrAfCrGfCm AfCrArGrAfCrGfU-idT | 56 | 23.0 | 6 |
| T25 vrt18 | 44 nt | rAfCrGrArAfCfUmGfCfCfCfUfCrArGfCfUrAf CfUfUfUfCrAfUrGfUfUrGfCfUrGrAfCrGmCr AfCrArGrAfCrGfU-idT | NB | NB | 6 |

TABLE 2-continued

| Modified Versions of VWF9.14 Aptamer Truncates | | | | | |
|---|---|---|---|---|---|
| ID | Length | Modified Sequence | Bmax (%) | Kd (nM) | SEQ ID NO: |
| T25 vrt19 | 44 nt | rAfCrGrArAfCfUrGmCfCfCfUfCrArGfCfUrAf CfUfUfUfCrAfUrGfUfUrGfCfUrGrAfCmGfCr AfCrArGrAfCrGfU-idT | NB | NB | 6 |
| T25 vrt20 | 44 nt | rAfCrGrArAfCfUrGfCmCmCfUfCrArGfCfUrA fCfUfUfUfCrAfUrGfUfUrGfCfUrGrAmCrGfCr AfCrArGrAfCrGfU-idT | NB | NB | 6 |
| T25 vrt21 | 44 nt | rAfCrGrArAfCfUrGfCfCfCmUfCrArGfCfUrAf CfUfUfUfCrAfUrGfUfUrGfCfUrGmAfCrGfCr AfCrArGrAfCrGfU-idT | 62 | 17.0 | 6 |
| T25 vrt22 | 44 nt | rAfCrGrArAfCfUrGfCmCfCfUfCrArGfCfUrAf CfUfUfUfCrAfUrGfUfUrGfCfUrGrAfCrGfCrA fCrArGrAfCrGfU-idT | NB | NB | 6 |
| T25 vrt23 | 44 nt | rAfCrGrArAfCfUrGfCfCmCfUfCrArGfCfUrAf CfUfUfUfCrAfUrGfUfUrGfCfUrGrAfCrGfCrA fCrArGrAfCrGfU-idT | NB | NB | 6 |
| T25 vrt24 | 44 nt | rAfCrGrArAfCfUrGfCfCfCfUfCrArGfCfUrAfC fUfUfUfCrAfUrGfUfUrGfCfUrGrAmCrGfCrAf CrArGrAfCrGfU-idT | 25 | 55.0 | 6 |
| T59 vrt1 | 30 nt | rAfCrGmAmAmCfUrGfCfCfCfUmCmGmAmU mCmGrAfCrGfCrAmCmAmGmAfCrGfU-idT | 76 | 1.5 | 4 |
| T59 vrt2 | 30 nt | rAfCrGmAmAmCfUrGfCfCfCmUmCmGmAm UmCmGmAfCrGfCrAmCmAmGmAfCrGfU- idT | 87 | 5.5 | 4 |
| T59 vrt3 | 30 nt | rAfCrGmAmAmCfUmGfCfCfCfUmCmGmAm UmCmGrAfCmGfCmAmCmAmGmAfCrGfU- idT | 49 | 288.0 | 4 |
| T59 vrt4 | 30 nt | mAfCmGmAmAmCfUmGfCfCfCfUmCmGmA mUmCmGmAfCmGfCmAmCmAmGmAfCmGf U-idT | 53 | 364.0 | 4 |
| T59 vrt5 | 30 nt | mAmCmGmAmAmCfUmGfCfCfCmUmCmGm AmUmCmGmAfCmGfCmAmCmAmGmAmC mGfU-idT | 61 | 260.0 | 4 |
| T59 vrt6 | 30 nt | mAmCmGmAmAmCfUrGfCfCfCfUmCmGmA mUmCmGrAfCrGfCrAmCmAmGmAmCmGfU -idT | 82 | 0.5 | 4 |
| T59 vrt7 | 30 nt | mAfCmGmAmAmCfUrGfCfCfCfUmCmGmA mUmCmGrAfCrGfCrAmCmAmGmAfCmGfU- idT | 84 | 0.8 | 4 |
| T59 vrt8 | 30 nt | mAfCrGmAmAmCfUrGfCfCfCfUmCmGmAm UmCmGrAfCrGfCrAmCmAmGmAfCrGfU-idT | 86 | 1.8 | 4 |
| T59 vrt9 | 30 nt | rAmCrGmAmAmCfUrGfCfCfCfUmCmGmAm UmCmGrAfCrGfCrAmCmAmGmAfCmGfU- idT | 86 | 1.0 | 4 |
| T59 vrt10 | 30 nt | rAfCmGmAmAmCfUrGfCfCfCfUmCmGmAm UmCmGrAfCrGfCrAmCmAmGmAmCrGfU- idT | 81 | 0.4 | 4 |
| T59 vrt11 | 30 nt | rAfCrGmAmAmCfUmGfCfCfCfUmCmGmAm UmCmGrAfCrGfCrAmCmAmGmAfCrGfU-idT | 88 | 1.3 | 4 |
| T59 vrt12 | 30 nt | rAfCrGmAmAmCfUrGfCfCfCfUmCmGmAmU mCmGrAfCrGfCmAmCmAmGmAfCrGfU-idT | 85 | 6.9 | 4 |
| T59 vrt13 | 30 nt | rAfCrGmAmAmCfUrGfCfCfCfUmCmGmAmU mCmGrAfCmGfCrAmCmAmGmAfCrGfU-idT | 76 | 29.0 | 4 |
| T59 vrt14 | 30 nt | mAmCmGmAmAmCfUrGfCfCfCmUmCmGm AmUmCmGmAfCrGfCrAmCmAmGmAmCmG fU-idT | 81 | 1.7 | 4 |

TABLE 2-continued

| Modified Versions of VWF9.14 Aptamer Truncates | | | | | |
|---|---|---|---|---|---|
| ID | Length | Modified Sequence | Bmax (%) | Kd (nM) | SEQ ID NO: |
| T59 vrt15 | 30 nt | mAmCmGmAmAmCfUmGfCfCfCmUmCmGm AmUmCmGmAfCmGfCrAmCmAmGmAmCm GfU-idT | 65 | 32.5 | 4 |
| T59 vrt16 | 30 nt | mAmCmGmAmAmCfUrGfCfCfCmUmCmGm AmUmCmGmAfCmGfCmAmCmAmGmAmC mGfU-idT | 57 | 132.5 | 4 |
| T59 vrt17 | 30 nt | mAmCmGmAmAmCfUmGfCfCfCmUmCmGm AmUmCmGmAfCrGfCmAmCmAmGmAmCm GfU-idT | 70 | 13.0 | 4 |
| T59 vrt18 | 30 nt | mAmCmGmAmAmCmUrGfCfCfCmUmCmGm AmUmCmGmAfCrGfCmAmCmAmGmAmCm GfU-idT | 83 | 5.7 | 4 |
| T59 vrt19 | 30 nt | mAmCmGmAmAmCmUmGfCfCfCmUmCmG mAmUmCmGmAfCrGfCmAmCmAmGmAmC mGfU-idT | 82 | 5.5 | 4 |
| T59 vrt20 | 30 nt | mAmCmGmAmAmCmUrGfCfCfCmUmCmGm AmUmCmGmAfCmGfCmAmCmAmGmAmC mGfU-idT | NB | NB | 4 |
| T59 vrt21 | 30 nt | mAmCmGmAmAmCfUmGfCfCfCfUmCmGm AmUmCmGmAfCmGfCrAmCmAmGmAmCm GfU-idT | 85 | 27.0 | 4 |
| T59 vrt22 | 30 nt | mAmCmGmAmAmCfUrGfCfCfCfUmCmGmA mUmCmGmAfCmGfCmAmCmAmGmAmCm GfU-idT | NB | NB | 4 |
| T59 vrt23 | 30 nt | mAmCmGmAmAmCfUmGfCfCfCfUmCmGm AmUmCmGmAfCrGfCmAmCmAmGmAmCm GfU-idT | 77 | 1.7 | 4 |
| T59 vrt24 | 30 nt | mAmCmGmAmAmCfUmGfCfCfCfUmCmGm AmUmCmGrAfCrGfCmAmCmAmGmAmCmG fU-idT | 83 | 2.4 | 4 |
| T59 vrt25 | 30 nt | mAmCmGmAmAmCfUrGfCfCfCfUmCmGmA mUmCmGrAfCmGfCmAmCmAmGmAmCmGf U-idT | 86 | 76.0 | 4 |
| T59 vrt26 | 30 nt | mAmCmGmAmAmCmUmGfCfCfCmUmCmG mAmUmCmGmAfCrGfCmAmCmAmGmAmC mGmU-idT | 89 | 18.0 | 4 |
| T59 vrt27 | 30 nt | mAmCmGmAmAmCmUmGfCfCfCmUmCmG mAmUmCmGmAfCrGmCmAmCmAmGmAm CmGfU-idT | NB | NB | 4 |
| T59 vrt28 | 30 nt | mAmCmGmAmAmCmUmGfCfCfCmUmCmG mAmUmCmGmAfCmGfCmAmCmAmGmAm CmGfU-idT | NB | NB | 4 |
| T59 vrt29 | 30 nt | mAmCmGmAmAmCmUmGmCfCfCmUmCm GmAmUmCmGmAfCrGfCmAmCmAmGmAm CmGfU-idT | 76 | 19.0 | 4 |
| T59 vrt30 | 30 nt | mAmCmGmAmAmCmUmGfCfCfCmUmCmG mAmUmCmGmAfCmGfCmAmCmAmGmAm CmGmU-idT | ND | ND | 4 |
| T59 vrt31 | 30 nt | mAmCmGmAmAmCmUmGfCfCfCmUmCmG mAmUmCmGmAfCmGmCmAmCmAmGmAm CmGfU-idT | ND | ND | 4 |
| T59 vrt32 | 30 nt | mAmCmGmAmAmCmUmGfCfCfCmUmCmG mAmUmCmGmAfCfGfCmAmCmAmGmAmC mGmU-idT | ND | ND | 4 |

TABLE 2-continued

Modified Versions of VWF9.14 Aptamer Truncates

| ID | Length | Modified Sequence | Bmax (%) | Kd (nM) | SEQ ID NO: |
|---|---|---|---|---|---|
| T79 vrt1 | 35 nt | rAfCrGmAmAmCfUrGfCfCfCfUmCmGmAmU mCmGrAfCrGfCrAmCmAmGmAfCrGfUmUm UmUmUmU-idT | 78 | 1.9 | 3 |
| T79 vrt2 | 35 nt | mAmCmGmAmAmCmUmGfCfCfCmUmCmG mAmUmCmGmAfCrGfCmAmCmAmGmAmC mGfUmUmUmUmUmU-idT | 81 | 24.0 | 3 |
| T79 vrt3 | 35 nt | mAmCmGmAmAmCmUmGfCfCfCmUmCmG mAmUmCmGmAfCmGfCmAmCmAmGmAm CmGfUmUmUmUmUmU-idT | 20 | 66.0 | 3 |
| T79 vrt4 | 35 nt | mAmCmGmAmAmCmUmGfCfCfCmUmCmG mAmUmCmGmAfCrGfCmAmCmAmGmAmC mGmUmUmUmUmUmU-idT | 75 | 13.0 | 3 |
| T79 vrt6 | 35 nt | mAmCmGmAmAmCmUmGfCfCfCmUmCmG mAmUmCmGmAfCfGfCmAmCmAmGmAmC mGfUmUmUmUmUmU-idT | 61 | 60.5 | 3 |
| T79 vrt7; DTR I-031 | 35 nt | mAmCmGmAmAmCmUmGfCfCfCmUmCmG mAmUmCmGmAfCfGfCmAmCmAmGmAmC mGmUmUmUmUmUmU-idT | 56 | 11.2 | 3; modified: 7 |
| T79 vrt8 | 35 nt | mAmCmGmAmAmCfUfGfCfCfCfUmCmGmA mUmCmGfAfCfGfCfAmCmAmGmAmCmGfU mUmUmUmUmU-idT | NB | NB | 3 |
| T79 vrt9 | 35 nt | mAmCmGmAmAmCfUfGfCfCfCfUmCmGmA mUmCmGfAfCfGfCfAmCmAmGmAmCmGm UmUmUmUmUmU-idT | ND | ND | 3 |
| T82 vrt. | 35 nt | rAfCrGmAmAmCfUrGfCfCfCfUmCmGmAmU mCmGrAfCrGfCrAmCmAmGmAfCrGfUmAm CmCmCmG-idT | 76 | 3.8 | 78 |
| T82 vrt4 | 35 nt | mAmCmGmAmAmCmUmGfCfCfCmUmCmG mAmUmCmGmAfCrGfCmAmCmAmGmAmC mGmUmAmCmCmCmG-idT | 87 | 38.5 | 78 |
| T82 vrt6 | 35 nt | mAmCmGmAmAmCmUmGfCfCfCmUmCmG mAmUmCmGmAfCfGfCmAmCmAmGmAmC mGfUmAmCmCmCmG-idT | 67 | 223.0 | 78 |
| T82 vrt7 | 35 nt | mAmCmGmAmAmCmUmGfCfCfCmUmCmG mAmUmCmGmAfCfGfCmAmCmAmGmAmC mGmUmAmCmCmCmG-idT | 78 | 268.5 | 78 |
| T82 vrt8 | 35 nt | mAmCmGmAmAmCfUfGfCfCfCfUmCmGmA mUmCmGfAfCfGfCfAmCmAmGmAmCmGfU mAmCmCmCmG-idT | NB | NB | 78 |
| T83 vrt1 | 35 nt | rAfCrGmAmAmCfUrGfCfCfCfUmCmGmAmU mCmGrAfCrGfCrAmCmAmGmAfCrGfUmAm AmAmAmA-idT | 73 | 2.1 | 79 |
| T83 vrt4 | 35 nt | mAmCmGmAmAmCmUmGfCfCfCmUmCmG mAmUmCmGmAfCrGfCmAmCmAmGmAmC mGmUmAmAmAmAmA-idT | 77 | 20.0 | 79 |
| T83 vrt6 | 35 nt | mAmCmGmAmAmCmUmGfCfCfCmUmCmG mAmUmCmGmAfCfGfCmAmCmAmGmAmC mGfUmAmAmAmAmA-idT | 67 | 209.0 | 79 |
| T83 vrt7 | 35 nt | mAmCmGmAmAmCmUmGfCfCfCmUmCmG mAmUmCmGmAfCfGfCmAmCmAmGmAmC mGmUmAmAmAmAmA-idT | 83 | 265.0 | 79 |
| T83 vrt8 | 35 nt | mAmCmGmAmAmCfUfGfCfCfCfUmCmGmA mUmCmGfAfCfGfCfAmCmAmGmAmCmGfU mAmAmAmAmA-idT | NB | NB | 79 |

TABLE 2-continued

Modified Versions of VWF9.14 Aptamer Truncates

| ID | Length | Modified Sequence | Bmax (%) | Kd (nM) | SEQ ID NO: |
|---|---|---|---|---|---|
| T84 vrt1 | 35 nt | rAfCrGmAmAmCfUrGfCfCfCfUmCmGmAmU mCmGrAfCrGfCrAmCmAmGmAfCrGfUmAm CmAmCmG-idT | 72 | 1.7 | 80 |
| T84 vrt4 | 35 nt | mAmCmGmAmAmCmUmGfCfCfCmUmCmG mAmUmCmGmAfCrGfCmAmCmAmGmAmC mGmUmAmCmAmCmG-idT | 77 | 22.0 | 80 |
| T84 vrt6 | 35 nt | mAmCmGmAmAmCmUmGfCfCfCmUmCmG mAmUmCmGmAfCfGfCmAmCmAmGmAmC mGfUmAmCmAmCmG-idT | 71 | 149.0 | 80 |
| T84 vrt7 | 35 nt | mAmCmGmAmAmCmUmGfCfCfCmUmCmG mAmUmCmGmAfCfGfCmAmCmAmGmAmC mGmUmAmCmAmCmG-idT | 74 | 182.0 | 80 |
| T84 vrt8 | 35 nt | mAmCmGmAmAmCfUfGfCfCfCfUmCmGmA mUmCmGfAfCfGfCfAmCmAmGmAmCmGfU mAmCmAmCmG-idT | NB | NB | 80 |
| T86 vrt1 | 34 nt | rAfCrGmAmAmCfUrGfCfCfCfUmCmGmUmU mUmCmAmUmCmGrAfCrGfCrAmCmAmGm AfCrGfU-idT | 80 | 0.9 | 82 |
| T86 vrt4 | 34 nt | mAmCmGmAmAmCmUmGfCfCfCmUmCmG mUmUmUmCmAmUmCmGmAfCrGfCmAmC mAmGmAmCmGmU-idT | 88 | 12.0 | 82 |
| T86 vrt6 | 34 nt | mAmCmGmAmAmCmUmGfCfCfCmUmCmG mUmUmUmCmAmUmCmGmAfCfGfCmAmC mAmGmAmCmGfU-idT | 85 | 52.0 | 82 |
| T86 vrt7 | 34 nt | mAmCmGmAmAmCmUmGfCfCfCmUmCmG mUmUmUmCmAmUmCmGmAfCfGfCmAmC mAmGmAmCmGmU-idT | 88 | 50.0 | 82 |
| T86 vrt8 | 34 nt | mAmCmGmAmAmCfUfGfCfCfCfUmCmGmU mUmUmCmAmUmCmGfAfCfGfCfAmCmAm GmAmCmGfU-idT | NB | NB | 82 |
| T87 vrt1 | 32 nt | rAfCrGmAmAmCfUrGfCfCfCfUmCmUmUmU mCmAmUmGrAfCrGfCrAmCmAmGmAfCrGf U-idT | 85 | 1.5 | 83 |
| T89 vrt1 | 36 nt | rAfCrGmAmAmCfUrGfCfCfCfUmCmGmUmA mUmUmAmUmUmUmCmGrAfCrGfCrAmCm AmGmAfCrGfU-idT | 84 | 1.2 | 85 |
| T89 vrt2 | 36 nt | mAmCmGmAmAmCmUmGfCfCfCmUmCmG mUmAmUmUmAmUmUmUmCmGmAfCrGfC mAmCmAmGmAmCmGfU-idT | 80 | 12.0 | 85 |
| T89 vrt3 | 36 nt | mAmCmGmAmAmCmUmGfCfCfCmUmCmG mUmAmUmUmAmUmUmUmCmGmAfCmGf CmAmCmAmGmAmCmGfU-idT | 49 | 63.0 | 85 |
| T89 vrt4 | 36 nt | mAmCmGmAmAmCmUmGfCfCfCmUmCmG mUmAmUmUmAmUmUmUmCmGmAfCrGfC mAmCmAmGmAmCmGmU-idT | 85 | 8.4 | 85 |
| T89 vrt6 | 36 nt | mAmCmGmAmAmCmUmGfCfCfCmUmCmG mUmAmUmUmAmUmUmUmCmGmAfCfGfC mAmCmAmGmAmCmGfU-idT | 73 | 34.5 | 85 |
| T89 vrt7 | 36 nt | mAmCmGmAmAmCmUmGfCfCfCmUmCmG mUmAmUmUmAmUmUmUmCmGmAfCfGfC mAmCmAmGmAmCmGmU-idT | 75 | 38.5 | 85 |
| T89 vrt8 | 36 nt | mAmCmGmAmAmCfUfGfCfCfCfUmCmGmU mAmUmUmAmUmUmUmCmGfAfCfGfCfAm CmAmGmAmCmGfU-idT | NB | NB | 85 |
| T89 vrt9 | 36 nt | mAmCmGmAmAmCfUfGfCfCfCfUmCmGmU mAmUmUmAmUmUmUmCmGfAfCfGfCfAm CmAmGmAmCmGmU-idT | ND | ND | 85 |

TABLE 2-continued

Modified Versions of VWF9.14 Aptamer Truncates

| ID | Length | Modified Sequence | Bmax (%) | Kd (nM) | SEQ ID NO: |
|---|---|---|---|---|---|
| T89 vrt10 | 36 nt | mAmCmGmAmAmCmUfGfCfCfCmUmCmGm UmAmUmUmAmUmUmUmCmGfAfCfGfCfA mCmAmGmAmCmGmU-idT | 86 | 548.0 | 85 |
| T90 vrt1 | 34 nt | rAfCrGmAmAmCfUrGfCfCfCfUmCmUmAmU mUmAmUmUmUmGrAfCrGfCrAmCmAmGm AfCrGfU-idT | 87 | 0.9 | 86 |
| T90 vrt4 | 34 nt | mAmCmGmAmAmCmUmGfCfCfCmUmCmU mAmUmUmAmUmUmUmGmAfCrGfCmAmC mAmGmAmCmGmU-idT | 85 | 10.2 | 86 |
| T90 vrt6 | 34 nt | mAmCmGmAmAmCmUmGfCfCfCmUmCmU mAmUmUmAmUmUmUmGmAfCfGfCmAmC mAmGmAmCmGfU-idT | 80 | 46.0 | 86 |
| T90 vrt7 | 34 nt | mAmCmGmAmAmCmUmGfCfCfCmUmCmU mAmUmUmAmUmUmUmGmAfCfGfCmAmC mAmGmAmCmGmU-idT | 80 | 42.0 | 86 |
| T90 vrt8 | 34 nt | mAmCmGmAmAmCfUfGfCfCfCfUmCmUmA mUmUmAmUmUmUmGfAfCfGfCfAmCmAm GmAmCmGfU-idT | ND | ND | 86 |
| T93 vrt1 | 36 nt | rAfCrGmAmAmCfUrGfCfCfCfUmCmUmAmU mUmUmCmAmUmUmUmGrAfCrGfCrAmCm AmGmAfCrGfU-idT | 89 | 0.8 | 89 |
| T93 vrt4 | 36 nt | mAmCmGmAmAmCmUmGfCfCfCmUmCmU mAmUmUmUmCmAmUmUmUmGmAfCrGfC mAmCmAmGmAmCmGmU-idT | 82 | 5.7 | 89 |
| T93 vrt6 | 36 nt | mAmCmGmAmAmCmUmGfCfCfCmUmCmU mAmUmUmUmCmAmUmUmUmGmAfCfGfC mAmCmAmGmAmCmGfU-idT | 82 | 33.0 | 89 |
| T93 vrt7 | 36 nt | mAmCmGmAmAmCmUmGfCfCfCmUmCmU mAmUmUmUmCmAmUmUmUmGmAfCfGfC mAmCmAmGmAmCmGmU-idT | 76 | 20.0 | 89 |
| T93 vrt8 | 36 nt | mAmCmGmAmAmCfUfGfCfCfCfUmCmUmA mUmUmUmCmAmUmUmUmGfAfCfGfCfAm CmAmGmAmCmGfU-idT | ND | ND | 89 |
| T94 vrt1 | 32 nt | rAfCrGmAmAmCfUrGfCfCfCfUmCmUmUmU mUmUmUmGrAfCrGfCrAmCmAmGmAfCrGf U-idT | 90 | 0.9 | 90 |
| T94 vrt6 | 32 nt | mAmCmGmAmAmCmUmGfCfCfCmUmCmU mUmUmUmUmUmGmAfCfGfCmAmCmAmG mAmCmGfU-idT | 78 | 42.0 | 90 |
| T94 vrt7 | 32 nt | mAmCmGmAmAmCmUmGfCfCfCmUmCmU mUmUmUmUmUmGmAfCfGfCmAmCmAmG mAmCmGmU-idT | 71 | 29.0 | 90 |
| T94 vrt8 | 32 nt | mAmCmGmAmAmCfUfGfCfCfCfUmCmUmU mUmUmUmUmGfAfCfGfCfAmCmAmGmAm CmGfU-idT | ND | ND | 90 |
| T95 vrt1 | 34 nt | rAfCrGmAmAmCfUrGfCfCfCfUmCmUmUmU mUmUmUmUmUmGrAfCrGfCrAmCmAmGm AfCrGfU-idT | 90 | 0.9 | 91 |
| DTR I-006 | 30 nt | mAmCmGmAmAmCmUmGfCfCfCmUmCmG mAmUmCmGmAfCrGfCmAmCmAmGmAmC mGfUidT | 80 | 7.0 | 4 |
| DTR I-007 | 30 nt | mAmCmGmAmAmCmUmGfCfCfCmUmCmG mAmUmCmGmAfCfGfCmAmCmAmGmAmC mGfUidT | 44 | 16.0 | 4 |

TABLE 2-continued

Modified Versions of VWF9.14 Aptamer Truncates

| ID | Length | Modified Sequence | Bmax (%) | Kd (nM) | SEQ ID NO: |
|---|---|---|---|---|---|
| DTRI-008 | 30 nt | mAmCmGmAmAmCmUmGfCfCfCmUmCmGmAmUmCmGmAfCrGfCmAmCmAmGmAmCmGmUidT | 67 | 7.0 | 4 |
| DTRI-009 | 26 nt | mAmCmGmAmAmCmUmGfCfCfCmUmC(6GLY)mGmAfCrGfCmAmCmAmGmAmCmGfUidT | 60 | 11.0 | 98 |
| DTRI-010 | 30 nt | mAmCmGmAmAmCmUmGfCfCfCmUmCmGmAmUmCmGmAfCdGfCmAmCmAmGmAmCmGfUidT | | | 4 |
| DTRI-011 | 30 nt | mAmCmGmAmAmCmUmGfCfCfCmUmCmGmUmAmAmGmAfCrGfCmAmCmAmGmAmCmGfUidT | 72 | 3.8 | 99 |
| DTRI-012 | 35 nt | mAmCmGmAmAmCmUmGfCfCfCmUmCmGmUmAmAmGmAfCrGfCmAmCmAmGmAmCmGfUmUmUmUmUmUidT | 73 | 5.5 | 100 |
| DTRI-013 | 30 nt | mCmCmGmAmAmCmUmGfCfCfCmUmCmGmAmUmCmGmAfCrGfCmAmCmAmGmAmCmGmGidT | 58 | 5.4 | 101 |
| DTRI-019 | 35 nt | mAmCmGmAmAmCmUmGfCfCfCmUmCmGmUmAmAmGmAfCrGfCmAmCmAmGmAmCmGmUmUmUmUmUmUidT | 64.8 | 4.3 | 100 unmod; mod: 8; |
| DTRI-020 | 35 nt | (C6L)mAmCmGmAmAmCmUmGfCfCfCmUmCmGmUmAmAmGmAfCrGfCmAmCmAmGmAmCmGmUmUmUmUmUmUidT | ND | ND | 100 unmod |
| DTRI-021 | 35 nt | Cholesterol-mAmCmGmAmAmCmUmGfCfCfCmUmCmGmUmAmAmGmAfCrGfCmAmCmAmGmAmCmGmUmUmUmUmUmUidT | ND | ND | unmod: 100; mod: 9; |
| DTRI-022 | 35 nt | mAmCmGmAmAmAmUmGmGmAmAmUmCmGmUmAmAmGmAmAmCmCmAmCmAmGmAmCmGmUmUmUmUmUmUidT | NB | NB | 102 |
| DTRI-023 | 35 nt | Cholesterol-mAmCmGmAmAmAmUmGmGmAmAmUmCmGmUmAmAmGmAmAmCmCmAmCmAmGmAmCmGmUmUmUmUmUmUidT | ND | ND | 102 |
| DTRI-034 | 35 nt | mAmCmGmAmAmCmUmGfCfCfCmUmCmGmUmAmAmGmAfCfGfCmAmCmAmGmAmCmGmUmUmUmUmUmUidT | 60 | 2.8 | 100 |

Table Legend:
All sequences are in 5' to 3' orientation
Lengths are not inclusive of inverted deoxythymidine
fU = 2'fluorouracil
fA = 2'fluoroadenine
fC = 2'fluorocytosine
mA = 2'O-methyladenine
mC = 2'O-methylcytosine
mG = 2'O-methylguanine
mU = 2'O-methyluracil
fG = 2'fluoroguanine
rG = 2' riboguanine
rA = 2' riboadenine
idT = inverted deoxythymidine on 3' end
(C6L) = hexylamino linker;
(6GLY) = hexaethylene glycol linker (incorporated using 9-O-Dimethoxytrityl-triethylene glycol, 1-[(2-cyanoethyl)-(N,N-diisopropyl)]-phosphoramidite);
cholesterol = cholesterol triethyleneglycol amidite incorporated on 5' end
NB = No Binding;
ND = Not Determined In addition to creating the VWF9.14 aptamer truncation variants and the VWF9.14 aptamer modification variants, we created several antidote sequences targeting these variants, which are listed in Table 3 below.

TABLE 3

Antidote Sequences

| ID | Alt ID | Length | Modified Sequence | SEQ ID NO: |
|---|---|---|---|---|
| AO1 | T59-AO1 | 15 nt | mUmCmGmAmGmGmGmCmAmGmUmUmCmG mU-idT | 103 |
| AO2 | T59-AO2 | 17 nt | mGmAmUmCmGmAmGmGmGmCmAmGmUmU mCmGmU-idT | 104 |
| AO3 | T59-AO3 | 14 nt | mGmAmUmCmGmAmGmGmGmCmAmGmUm U-idT | 105 |
| AO4 | T59-AO4 | 16 nt | mUmCmGmAmUmCmGmAmGmGmGmCmAmG mUmU-idT | 106 |
| AO5 | T59-AO5 | 17 nt | mGmUmCmGmAmUmCmGmAmGmGmGmCmA mGmUmU-idT | 107 |
| AO6 | T59-AO6 | 14 nt | mGmUmCmGmAmUmCmGmAmGmGmGmCm A-idT | 108 |
| AO7 | T59-AO7 | 17 nt | mUmGmCmGmUmCmGmAmUmCmGmAmGmG mGmCmA-idT | 109 |
| AO8 | T59-AO8 | 17 nt | mUmGmUmGmCmGmUmCmGmAmUmCmGmA mGmGmG-idT | 110 |
| AO9 | T59-AO9 | 19 nt | mUmCmUmGmUmGmCmGmUmCmGmAmUmC mGmAmGmGmG-idT | 111 |
| AO10 | T59-AO10 | 16 nt | mUmCmUmGmUmGmCmGmUmCmGmAmUmC mGmA-idT | 112 |
| AO11 | T59-AO11 | 14 nt | mUmCmUmGmUmGmCmGmUmCmGmAmUm C-idT | 113 |
| AO12 | T59-AO12 | 17 nt | mAmCmGmUmCmUmGmUmGmCmGmUmCmG mAmUmC-idT | 114 |
| AO13 | T70-AO1 | 16 nt | mAmAmUmGmAmGmGmGmCmAmGmUmUmC mGmU-idT | 115 |
| AO14 | T70-AO2 | 18 nt | mAmUmAmAmUmGmAmGmGmGmCmAmGmU mUmCmGmU-idT | 116 |
| AO15 | T70-AO3 | 13 nt | mAmAmUmGmAmGmGmGmCmAmGmUmU-idT | 117 |
| AO16 | T70-AO4 | 15 nt | mAmUmAmAmUmGmAmGmGmGmCmAmGmU mU-idT | 118 |
| AO17 | T70-AO5 | 18 nt | mUmCmAmAmUmAmAmUmGmAmGmGmGmC mAmGmUmU-idT | 119 |
| AO18 | T70-AO6 | 19 nt | mGmUmCmAmAmUmAmAmUmGmAmGmGmG mCmAmGmUmU-idT | 120 |
| AO19 | T70-AO7 | 16 nt | mGmUmCmAmAmUmAmAmUmGmAmGmGmG mCmA-idT | 121 |
| AO20 | T70-AO8 | 19 nt | mUmGmCmGmUmCmAmAmUmAmAmUmGmA mGmGmGmCmA-idT | 122 |
| AO21 | T70-AO9 | 13 nt | mGmUmCmAmAmUmAmAmUmGmAmGmG-idT | 123 |
| AO22 | T70-AO10 | 16 nt | mUmGmCmGmUmCmAmAmUmAmAmUmGmA mGmG-idT | 124 |
| AO23 | T70-AO11 | 15 nt | mUmCmUmGmUmGmCmGmUmCmAmAmUmA mA-idT | 125 |

TABLE 3-continued

Antidote Sequences

| ID | Alt ID | Length | Modified Sequence | SEQ ID NO: |
|---|---|---|---|---|
| AO24 | T70-AO12 | 18 nt | mAmCmGmUmCmUmGmUmGmCmGmUmCmA mAmUmAmA-idT | 126 |
| AO25 | T49-AO1 | 17 nt | mAmAmUmCmGmAmGmGmGmCmAmGmUmU mCmGmU-idT | 127 |
| AO26 | T49-AO2 | 19 nt | mAmUmAmAmUmCmGmAmGmGmGmCmAmG mUmUmCmGmU-idT | 128 |
| AO27 | T49-AO3 | 14 nt | mAmAmUmCmGmAmGmGmGmCmAmGmUm U-idT | 129 |
| AO28 | T49-AO4 | 16 nt | mAmUmAmAmUmCmGmAmGmGmGmCmAmG mUmU-idT | 130 |
| AO29 | T49-AO5 | 20 nt | mUmCmGmAmAmUmAmAmUmCmGmAmGmG mGmCmAmGmUmU-idT | 131 |
| AO30 | T49-AO6 | 21 nt | mGmUmCmGmAmAmUmAmAmUmCmGmAmG mGmGmCmAmGmUmU-idT | 132 |
| AO31 | T49-AO7 | 18 nt | mGmUmCmGmAmAmUmAmAmUmCmGmAmG mGmGmCmA-idT | 133 |
| AO32 | T49-AO8 | 21 nt | mUmGmCmGmUmCmGmAmAmUmAmAmUmC mGmAmGmGmGmCmA-idT | 134 |
| AO33 | T49-AO9 | 15 nt | mGmUmCmGmAmAmUmAmAmUmCmGmAmG mG-idT | 135 |
| AO34 | T49-AO10 | 18 nt | mUmGmCmGmUmCmGmAmAmUmAmAmUmC mGmAmGmG-idT | 136 |
| AO35 | T49-AO11 | 16 nt | mUmCmUmGmUmGmCmGmUmCmGmAmAmU mAmA-idT | 137 |
| AO36 | T49-AO12 | 19 nt | mAmCmGmUmCmUmGmUmGmCmGmUmCmG mAmAmUmAmA-idT | 138 |
| AO37 | T73-AO1 | 22 nt | mGmAmUmCmGmAmGmGmGmCmAmGmUmU mCmGmUmUmAmUmGmC-idT | 139 |
| AO38 | T74-AO1 | 20 nt | mGmAmUmCmGmAmGmGmGmCmAmGmUmU mCmGmUmGmGmG-idT | 140 |
| AO39 | T75-AO1 | 22 nt | mGmAmUmCmGmAmGmGmGmCmAmGmUmU mCmGmUmGmGmGmGmG-idT | 141 |
| AO40 | T76-AO1 | 22 nt | mGmAmUmCmGmAmGmGmGmCmAmGmUmU mCmGmUmGmUmGmUmG-idT | 142 |
| AO41 | T77-AO1 | 21 nt | mGmAmUmCmGmAmGmGmGmCmAmGmUmU mCmGmUmUmUmUmU-idT | 143 |
| AO42 | T78-AO1 | 23 nt | mGmAmUmCmGmAmGmGmGmCmAmGmUmU mCmGmUmUmUmUmGmGmG-idT | 144 |
| AO43 | T79-AO1 | 22 nt | mAmAmAmAmAmAmCmGmUmCmUmGmUmG mCmGmUmCmGmAmUmC-idT | 145 |
| AO44 | T80-AO1 | 20 nt | mUmUmUmAmCmGmUmCmUmGmUmGmCmG mUmCmGmAmUmC-idT | 146 |
| AO45 | T81-AO1 | 22 nt | mUmGmUmGmUmAmCmGmUmCmUmGmUmG mCmGmUmCmGmAmUmC-idT | 147 |
| AO46 | T82-AO1 | 22 nt | mCmGmGmGmUmAmCmGmUmCmUmGmUmG mCmGmUmCmGmAmUmC-idT | 148 |
| AO47 | T83-AO1 | 22 nt | mUmUmUmUmUmAmCmGmUmCmUmGmUmG mCmGmUmCmGmAmUmC-idT | 149 |

TABLE 3-continued

Antidote Sequences

| ID | Alt ID | Length | Modified Sequence | SEQ ID NO: |
|---|---|---|---|---|
| AO48 | T84-AO1 | 22 nt | mCmGmUmGmUmAmCmGmUmCmUmGmUmG mCmGmUmCmGmAmUmC-idT | 150 |
| AO49 | T73-AO2 | 16 nt | mGmGmGmCmAmGmUmUmCmGmUmUmAmU mGmC-idT | 151 |
| AO50 | T74-AO2 | 14 nt | mGmGmGmCmAmGmUmUmCmGmUmGmGm G-idT | 152 |
| AO51 | T75-AO2 | 16 nt | mGmGmGmCmAmGmUmUmCmGmUmGmGmG mGmG-idT | 153 |
| AO52 | T76-AO2 | 16 nt | mGmGmGmCmAmGmUmUmCmGmUmGmUmG mUmG-idT | 154 |
| AO53 | T77-AO2 | 15 nt | mGmGmGmCmAmGmUmUmCmGmUmUmUmU mU-idT | 155 |
| AO54 | T78-AO2 | 17 nt | mGmGmGmCmAmGmUmUmCmGmUmUmUmU mGmGmG-idT | 156 |
| AO55 | T79-AO2/DTRI-025 | 16 nt | mAmAmAmAmAmAmCmGmUmCmUmGmUmG mCmG-idT | 157 |
| AO56 | T80-AO2 | 14 nt | mUmUmUmAmCmGmUmCmUmGmUmGmCm G-idT | 158 |
| AO57 | T81-AO2 | 16 nt | mUmGmUmGmUmAmCmGmUmCmUmGmUmG mCmG-idT | 159 |
| AO58 | T82-AO2 | 16 nt | mCmGmGmGmUmAmCmGmUmCmUmGmUmG mCmG-idT | 160 |
| AO59 | T83-AO2 | 16 nt | mUmUmUmUmUmAmCmGmUmCmUmGmUmG mCmG-idT | 161 |
| AO60 | T84-AO2 | 16 nt | mCmGmUmGmUmAmCmGmUmCmUmGmUmG mCmG-idT | 162 |
| AO61 | T86-AO1 | 17 nt | mUmCmUmGmUmGmCmGmUmCmGmAmUmG mAmAmA-idT | 163 |
| AO62 | T87-AO1 | 16 nt | mUmCmUmGmUmGmCmGmUmCmAmUmGmA mAmA-idT | 164 |
| AO63 | T89-AO1 | 19 nt | mUmCmUmGmUmGmCmGmUmCmGmAmAmA mUmAmAmUmA-idT | 165 |
| AO64 | T90-AO1 | 18 nt | mUmCmUmGmUmGmCmGmUmCmAmAmAmU mAmAmUmA-idT | 166 |
| AO65 | T93-AO1 | 20 nt | mUmCmUmGmUmGmCmGmUmCmAmAmAmU mGmAmAmAmUmA-idT | 167 |
| AO66 | T94-AO1 | 16 nt | mUmCmUmGmUmGmCmGmUmCmAmAmAmA mAmA-idT | 168 |
| AO67 | T95-AO1 | 18 nt | mUmCmUmGmUmGmCmGmUmCmAmAmAmA mAmAmAmA-idT | 169 |
| AO68 | T96-AO1 | 18 nt | mGmGmGmGmUmGmCmGmUmCmAmAmAmA mAmAmAmA-idT | 170 |
| AO69 | T97-AO1 | 17 nt | mGmGmGmGmUmGmCmGmUmCmGmAmUmG mAmAmA-idT | 171 |
| AO70 | T98-AO1 | 16 nt | mGmGmGmGmUmGmCmGmUmCmAmUmGmA mAmA-idT | 172 |
| AO71 | T99-AO1 | 18 nt | mGmGmGmGmUmGmCmGmUmCmAmAmAmU mAmAmUmA-idT | 173 |
| AO72 | T101-AO1 | 16 nt | mGmGmGmGmUmGmCmGmUmCmAmAmAmA mAmA-idT | 174 |
| AO73 | T79-AO3 | 17 nt | mAmAmAmAmAmAmCmGmUmCmUmGmUmA mGmUmU-idT | 175 |
| AO74 | T79-AO4 | 15 nt | mAmAmAmAmAmAmCmGmUmCmUmGmGmU mU-idT | 176 |
| AO75 | T79-AO5 | 20 nt | mAmAmAmAmAmAmCmGmUmCmUmGmUmA mGmUmUmCmGmU-idT | 177 |
| AO76 | T79-AO6 | 18 nt | mAmAmAmAmAmAmCmGmUmCmUmGmGmU mUmCmGmU-idT | 178 |
| AO85 | T59-AO13 | 12 nt | mUmCmUmGmUmGmCmGmUmCmGmA-idT | 179 |
| AO86 | T79-AO7/DTRI-038 | 16 nt | mAmAmAmAmAmAmCmGmUmCmUmGmUmG mCmG | 180 |

Figure 17:
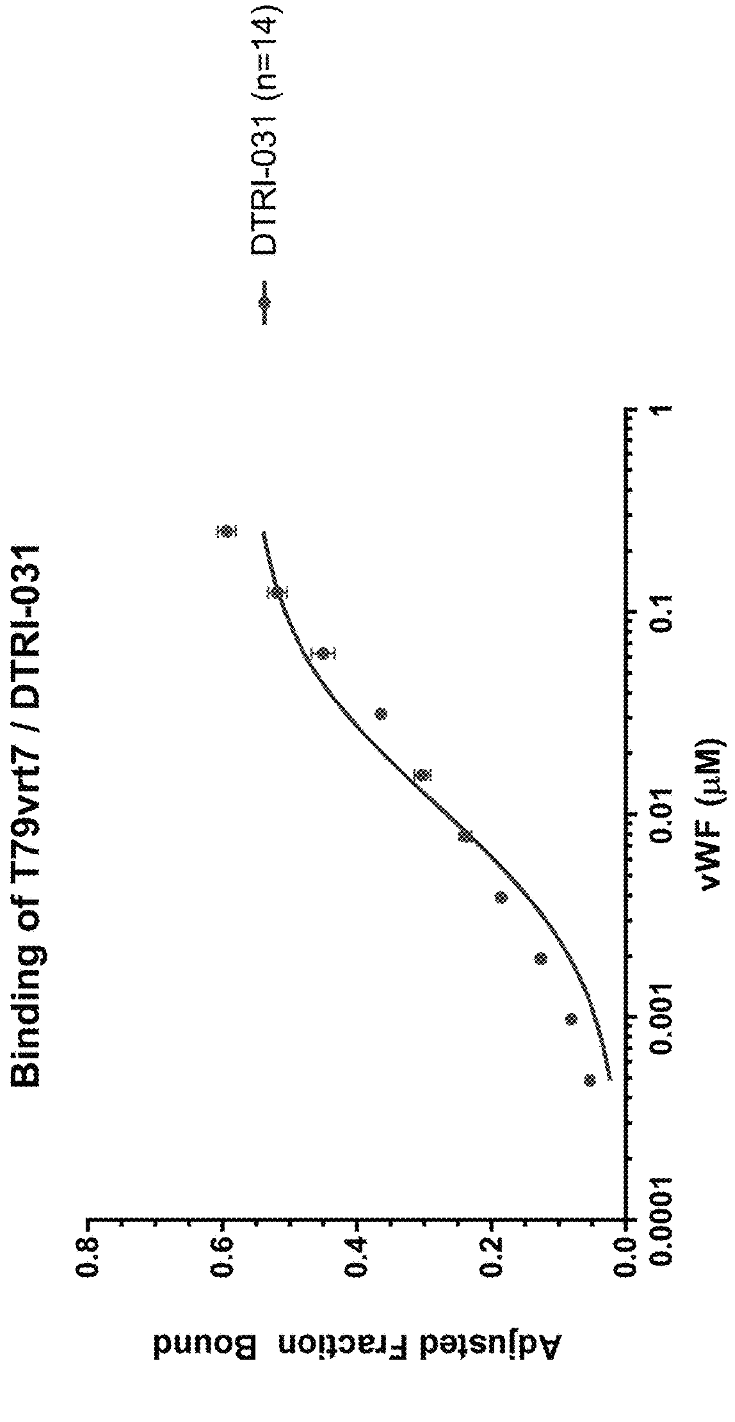
FIG. 17 shows nitrocellulose filter binding assay data for T79VRT7/DTRI-031 (SEQ ID NO: 7) aptamer.

All sequences are represented in a 5' to 3' orientation
Lengths are not inclusive of inverted deoxythymidine
mG = 2'O-Methyl G;
mA = 2'O-Methyl A;
mC = 2'O-Methyl C;
mU = 2'O-Methyl U;
idT—inverted deoxythymidine Binding Studies To determine the binding affinity of the VWF9.14 aptamer variants for the VWF protein, we performed binding assays with several of the variants. The binding data is summarized above in Tables 1-2. See also FIGS. 1, and 16-17.

PFA Analysis of VWF9.14 Aptamer Variants

Figure 13:
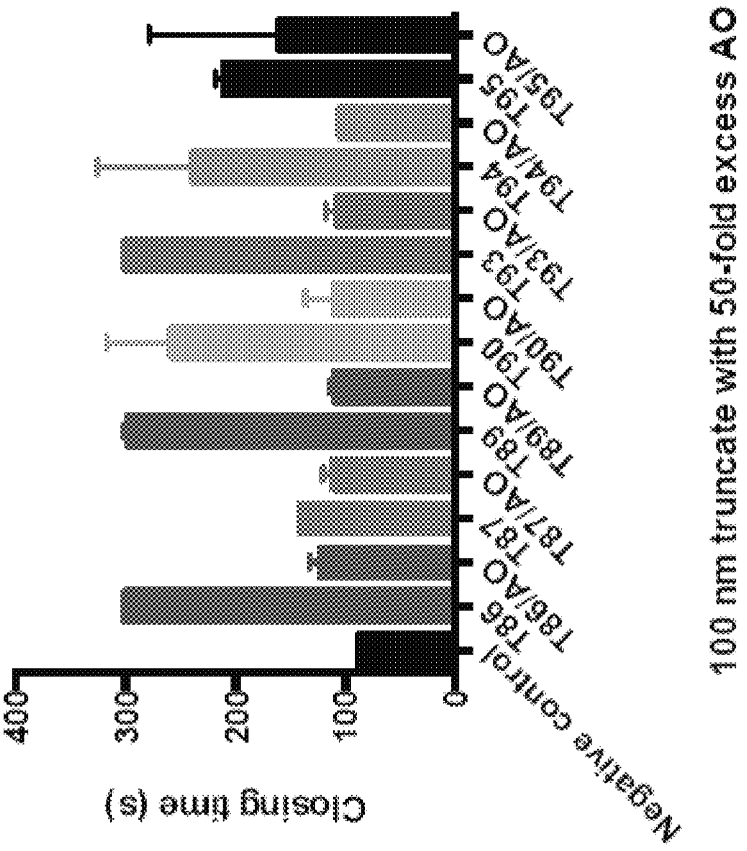
FIG. 13 shows PFA results for VWF9.14T86 (SEQ ID NO: 82), VWF9.14T87 (SEQ ID NO: 83), VWF9.14T89 (SEQ ID NO: 85), VWF9.14T90 (SEQ ID NO: 86), VWF9.14T93 (SEQ ID NO: 89), VWF9.14T94 (SEQ ID NO: 90), and VWF9.14T95 (SEQ ID NO: 91) with and without antidotes (AO61 (SEQ ID NO: 163), AO62 (SEQ ID NO: 164), AO63 (SEQ ID NO: 165), AO64 (SEQ ID NO: 166), AO65 (SEQ ID NO: 167), AO66 (SEQ ID NO: 168), and AO67 (SEQ ID NO: 169), respectively.

As shown in FIGS. 12 and 13, we performed platelet function assay (PFA) for VWF9.14T59 with and without antidotes VWF9.14T59-AO3,-AO10, and-AO11 (AO3, AO10, and AO11 respectively). Also shown are PFA results for aptamer VWF9.14T79 with and without antidotes VWF9.14T79-AO1 (AO43) and VWF9.14T79-AO2 (AO55). Results are shown for aptamer VWF9.14T82 with and without antidotes VWF9.14T82-AO1 (AO46) and VWF9.14T82-AO2 (AO58). Results are shown for aptamer VWF9.14T84 with and without antidotes VWF9.14T84-AO1 (AO48) and VWF9.14T84-AO2 (AO60). These results demonstrate that the anti-thrombotic activity of several of the VWF9.14 aptamers could be reversed using designed antidotes.

In Vivo Testing of VWF9.14 Aptamer Variants

Several of the VWF9.14 aptamer variants were tested in a murine arterial thrombosis model and a murine saphenous vein bleeding model. See FIGS. 4-11. In the murine arterial thrombosis model, the left jugular vein was cannulated and the right carotid artery was exposed and a flow probe was placed. After 5 minutes the vehicle indicated was injected i.v. into the mouse and a 10% $FeCl_3$ patch was placed on the carotid artery for 3 minutes. The blood flow in the carotid artery was then monitored for 1 hour and recorded using the probe In the murine arterial thrombosis model, injecting a vehicle (no aptamer/negative control) prior to $FeCl_3$ injury resulted in the vessel becoming occluded in approximately 2 minutes following removal of the $FeCl_3$patches. See FIG.

4. On the other hand, injecting either T79vrt7/DTRI-031 or PEG-VWF9.14T79-VRT7/DTRI-031 aptamer at a dosing of 0.375 mg/kg into this model prior to $FeCl_3$injury resulted in the vessel remaining patent for 60 minutes following removal of the $FeCl_3$patches. See FIGS. 5 and 7. These results demonstrate that the aptamers had potent anti-thrombotic activity.

The VWF9.14T79-VRT7 aptamer was also injected at a dosing of 0.0375 mg/kg into the model prior to $FeCl_3$ injury, which resulted in the vessel remained patent for >60 minutes following removal of the $FeCl_3$ patches. See FIG. 5. This result demonstrated that the dosing of the VWF9.14T79-VRT7 aptamer may be decreased and still exhibit potent anti-thrombotic activity. The dose range study is presented in FIG. 7.

Figure 8:
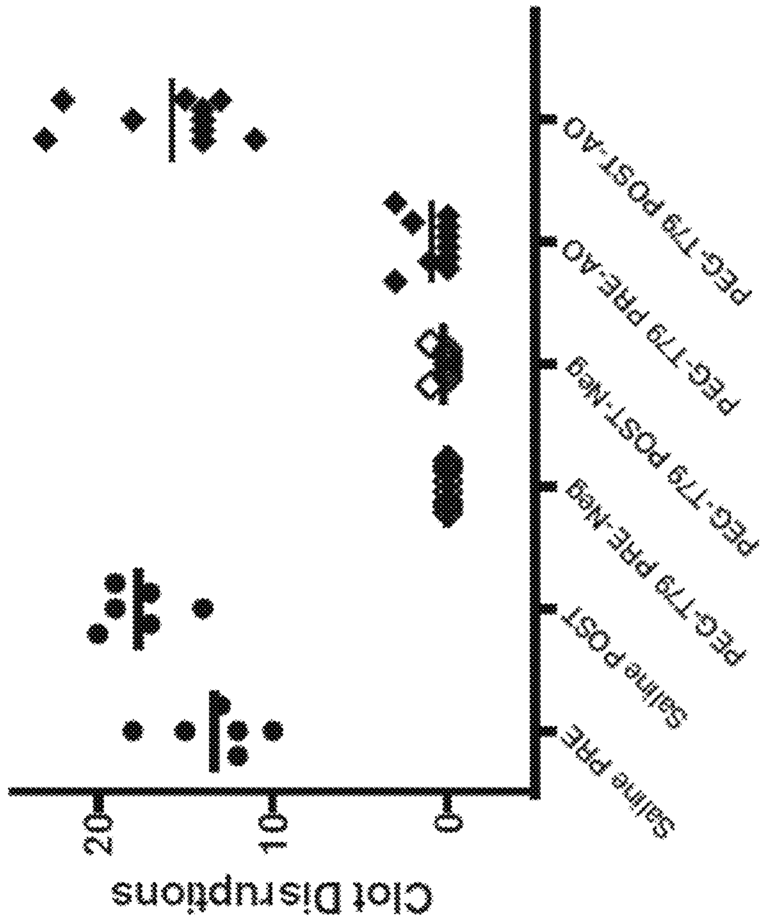
FIG. 8 shows a scatter plot of the number of clot disruptions before (PRE) and after (POST) injection of a 10 fold molar ratio of VWF9.14T79-AO2 (AO55; SEQ ID NO: 157) antidote or no antidote (Neg) following injection of either saline or the PEG-VWF9.14T79-VRT7 (SEQ ID NO: 7) aptamer (dose 0.375 mg/kg) in the murine saphenous vein bleeding model.
Figure 9A:
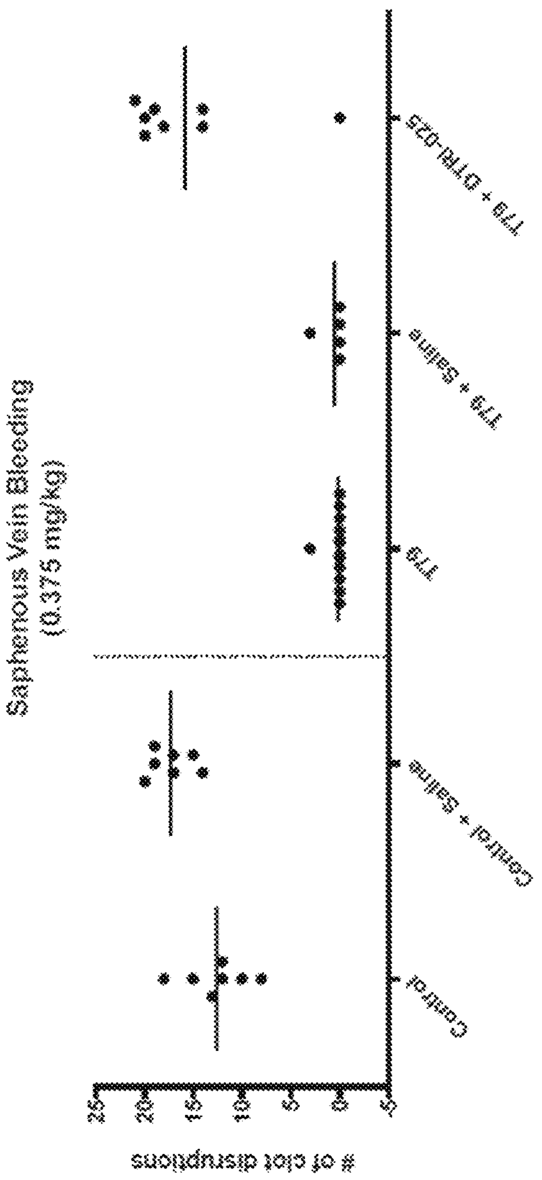
FIG. 9A shows a scatter plot of the clot disruptions before and after injection of a 10 fold molar ratio of VWF9.14T79-AO2 (DTRI-025; SEQ ID NO: 157) antidote or no antidote (Saline) following injection of either saline (Control) or the VWF9.14T79-VRT7 aptamer (dose 0.375 mg/kg; SEQ ID NO: 7) in the murine saphenous vein bleeding model.
Figure 9B:
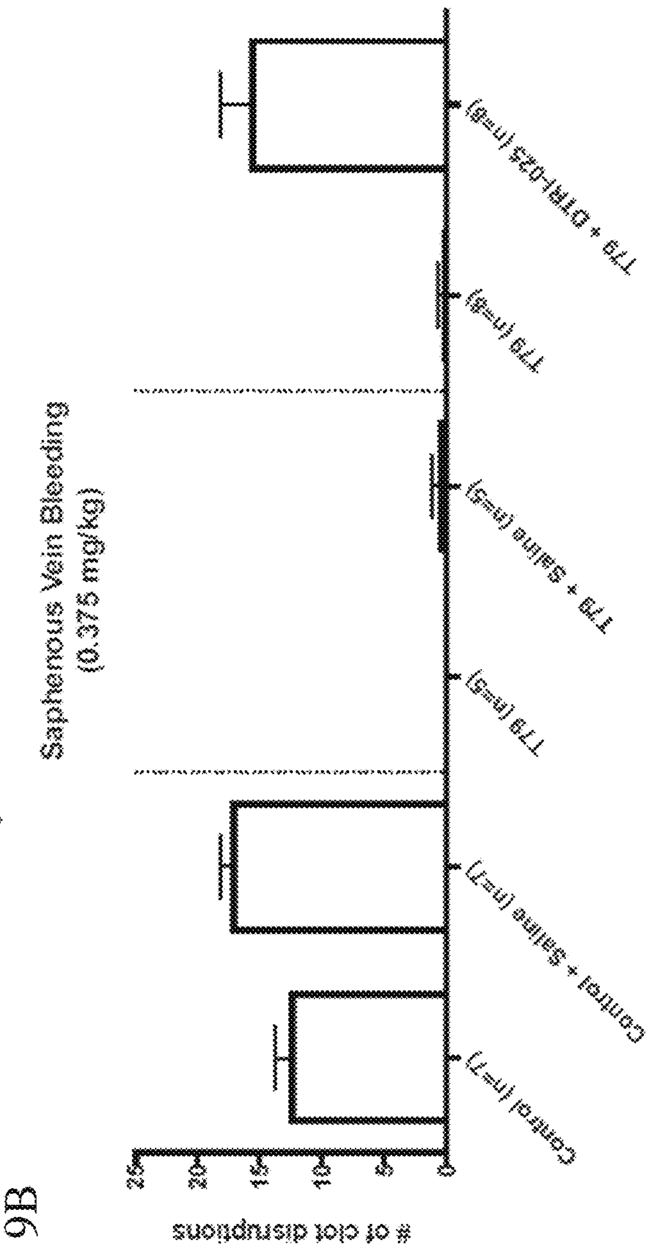
FIG. 9B shows a bar graph of the clot disruptions before and after injection of a 10 fold molar ratio of VWF9.14T79-AO2 (DTRI-025; SEQ ID NO: 157) antidote or no antidote (Saline) following injection of either saline (Control) or the VWF9.14T79-VRT7 aptamer (dose 0.375 mg/kg; SEQ ID NO: 7) in the murine saphenous vein bleeding model.
Figure 10:
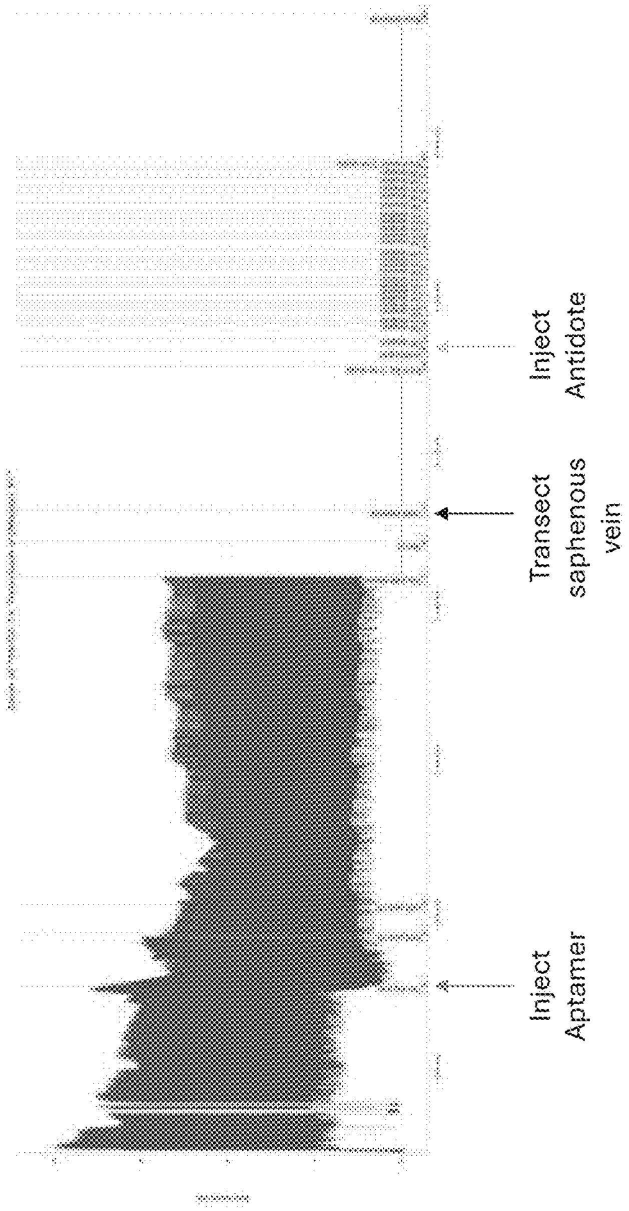
FIG. 10 shows an example of a carotid artery blood flow tracing and timeline from a single study of the combined arterial thrombosis and saphenous vein bleeding model. The left side of the figure captures the first half of the study evaluating carotid artery vessel patency after thrombosis challenge. The right side captures vessel transection, bleeding, and clot formation before and after antidote administration.
Figure 11:
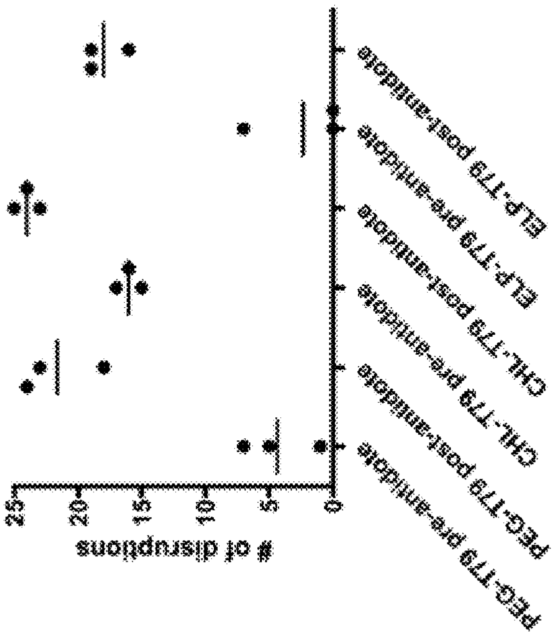
FIG. 11 shows the number of disruptions before (PRE) and after (POST) injection of the VWF9.14T9-AO2 (AO55; SEQ ID NO: 157) antidote post-thrombosis saphenous vein bleeding following injection of the PEG-VWF9.14T79-VRT7 aptamer (SEQ ID NO: 7), the Cholesterol-VWF9.14T79-VRT7 aptamer, or the Elastin-like polypeptide (ELP)-VWF9.14T79-VRT7 aptamer in the combined murine arterial thrombosis and saphenous vein bleeding model.

In the murine saphenous vein bleeding model, the left jugular vein of a mouse is cannulated and the right medial saphenous vein is exposed prior to injecting the aptamer at the indicated dose. Five minutes after injecting the aptamer the saphenous vein is transected and bleeding is followed for 15 minutes, the antidote is then injected to reverse the effects of the aptamer and bleeding is followed for an additional 20 minutes. The activity of the PEG-VWF9.14T79-VRT7 aptamer could be successfully reversed by injecting the VWF9.14T79-AO2 (AO55) antidote. See FIG. 8. For example, as shown in FIG. 8, the clot disruptions increased after injection of the VWF9.14T9-AO2 (AO55) antidote demonstrating that the activity of the aptamers could be reversed.

Furthermore, we tested the PEG-VWF9.14T79-VRT7 aptamer, the Cholesterol-VWF9.14T79-VRT7 aptamer, the Elastin-like polypeptide (ELP)-VWF9.14T79-VRT7 aptamer, and the VWF9.14T79-AO2 (AO55) antidote in a combined murine arterial thrombosis and saphenous vein bleeding model. In this model the left jugular vein was cannulated and the right carotid artery was exposed and a transonic flow probe was placed in the animal. Five minutes after placement of the probe the aptamer was injected at the indicated dose. After an additional 5 minutes two 7.5% $FeCl_3$ patches were placed on the right carotid artery for 3 minutes prior to removal. Thirty minutes after removal the saphenous vein was exposed and transected and bleeding monitored for 15 minutes. The antidote was injected and clot formation was observed for an additional 15 minutes. See FIGS. 10-11. In this model, after first demonstrating the potent anti-thrombotic activity of each aptamer, the VWF9.14T79- AO2 (AO55) antidote could still successfully reverse the activities of the aptamers.

Example 2—VWF Aptamer Thrombolytic Activity

The T79VRT7 aptamer and was also tested for thrombolytic activity in a murine carotid artery occlusion model and a murine intracranial hemorrhage model. See FIGS. 18-19.

Murine Carotid Artery Occlusion and Thrombolysis Model

We employed a murine carotid artery occlusion model where we intubated adult C57BL/6J mice (Jackson Laboratory, Bar Harbor, ME) (18-24 g) and exposed the left jugular vein. Next, we exposed the right common carotid artery and placed a transonic flow probe (Transonic Systems Incorporated, Ithaca, NY) around the artery. The blood flow was measured for 5 minutes to achieve a stable baseline. We then induced thrombosis by applying 10% ferric chloride-soaked Whatmann paper on the vessel. The time to occlusion was then recorded. Twenty minutes after occlusion, we intravenously inject either saline (negative control), anti-VWF aptamer (VWF9.14T79VRT7) at a dose of 0.5 mg/kg, or recombinant tissue plasminogen activator (rTPA) at a dose of 10 mg/kg. We monitored for reperfusion using the Doppler flow probe and determine the time to re-establish perfusion. We terminated the experiment if no recanalization occurred after 60 minutes. The animals were then sacrificed and the brain and common carotid arteries harvested for analysis.

Figure 18:
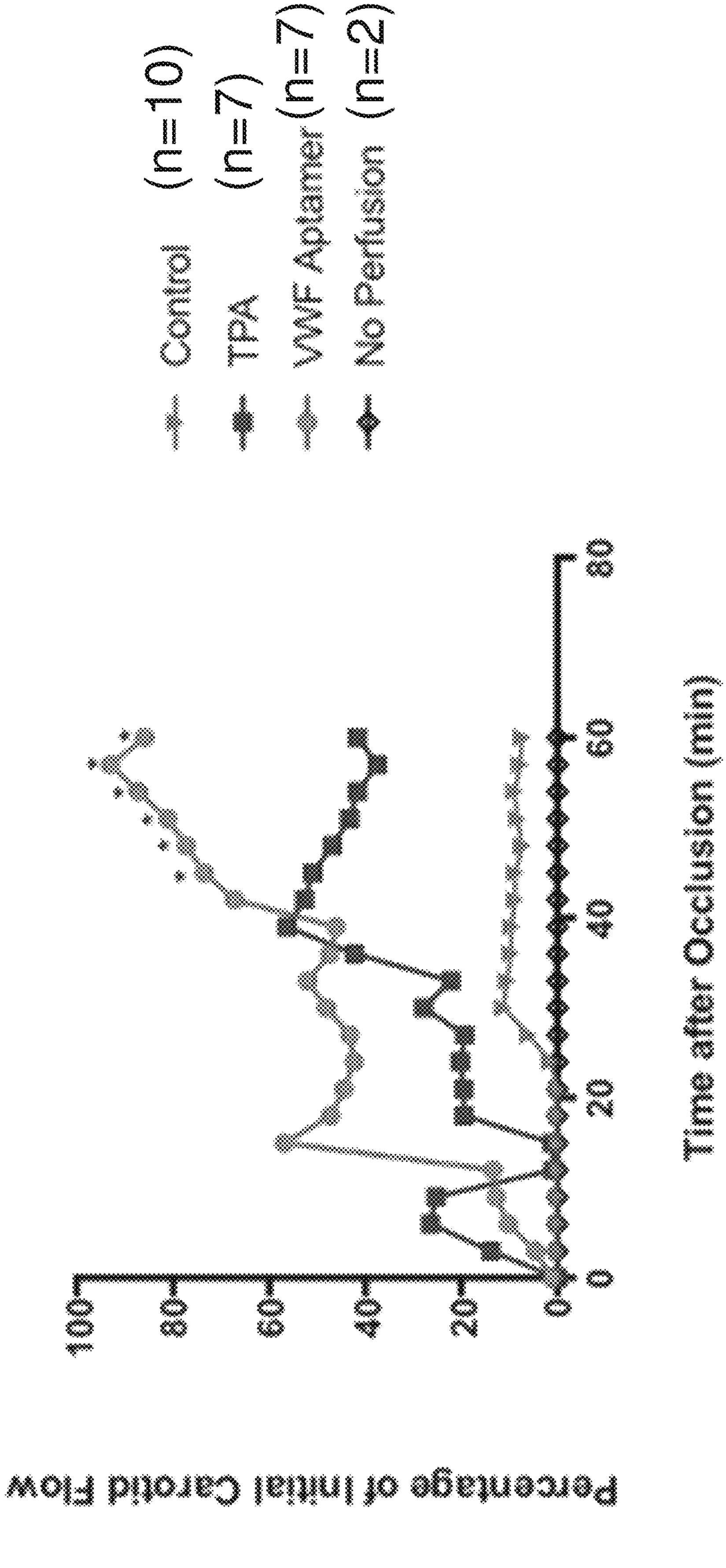
FIG. 18 shows a graph indicating the percentage of initial carotid flow at various time points after occlusion in mice treated with control, rTPA (recombinant tissue plasminogen activator), anti-VWF aptamer (both VWF9.14T79VRT7 and Cholesterol-VWF9.14T79-VRT7), or no perfusion. As indicated in the graph, the anti-VWF aptamer (VWF9.14T79VRT7; SEQ ID NO: 7) had superior thrombolytic activity compared to rTPA.

As shown in FIG. 18, in the murine carotid artery occlusion model, the percentage of initial carotid flow increased to a greater degree over time with the T79VRT7 aptamer verses rTPA, control, or no perfusion. Thus, the VWF T79VRT7 aptamer had superior thrombolytic activity compared to rTPA.

Murine Intracranial Hemorrhage Model

We anesthetized adult C57BL/6J mice (18-24 g) and exposed the left jugular vein and right common carotid artery. We then injected either saline (negative control), anti-VWF aptamer (VWF9.14T79-VRT7) at a dose of 0.5 mg/kg, rTPA at dose of 10 mg/kg or anti-VWF aptamer (0.5 mg/kg) and matched antidote oligonucleotide (VWF9.14T79-AO2 , also called AO55) at a dose of 2.5 mg/kg 5 minutes after the aptamer. To induce intracranial hemorrhage, we inserted a silicone-coated 6-0 nylon filament into the carotid artery and advanced it until we punctured the internal carotid artery (ICA) terminus, resulting in subarachnoid hemorrhage (SAH). To evaluate the volume of infarct and hemorrhage, we performed magnetic resonance imaging (MRI) on a 9.4 Tesla MRI (Bruker Biospin, Billerica, MA) 90 minutes after induced intracranial hemorrhage.

Figure 19:
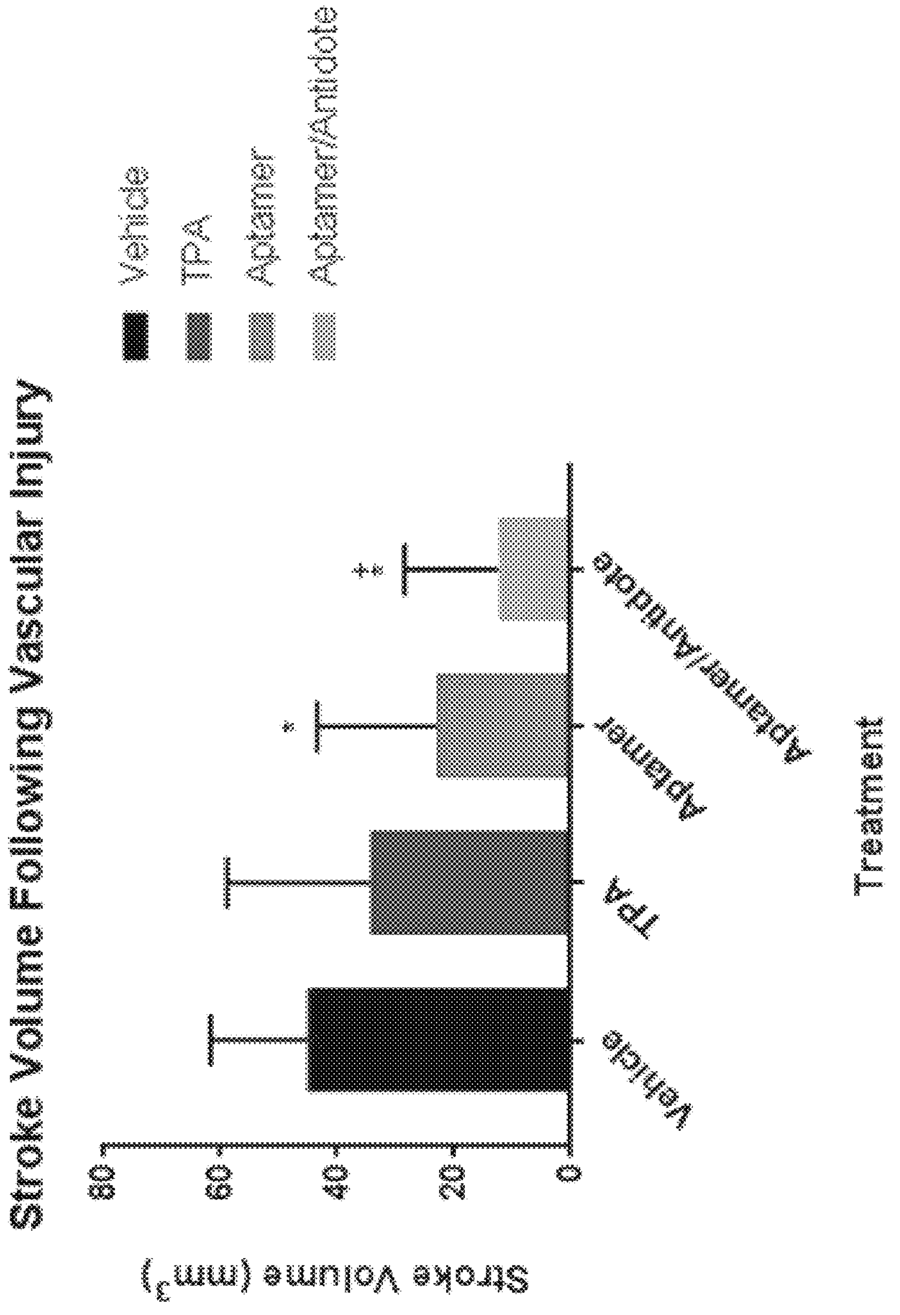
FIG. 19 shows a graph indicating stroke volume following vascular injury in the murine intracranial hemorrhage model in mice treated with vehicle, rTPA, anti-VWF aptamer (VWF9.14T79-VRT7; SEQ ID NO: 7), or anti-VWF aptamer (VWF9.14T79-VRT7) and VWF antidote (VWF9.14T79-T79-AO2, also called AO55; SEQ ID NO: 157).

FIG. 19 shows a graph indicating stroke volume following vascular injury in the murine intracranial hemorrhage model in mice treated with vehicle, rTPA, anti-VWF aptamer (VWF9.14T79-VRT7), or anti-VWF aptamer (VWF9.14T79-VRT7) and VWF antidote (VWF9.14T79-AO2 , also called AO55).

Example 3-Additional In Vivo Studies with a VWF Aptamer

Ischemic stroke is a leading cause of death and disability in the western world.[1] Approved thrombolytic stroke therapy using recombinant tissue plasminogen activator (rTPA) is limited by several critical factors. First, the significant risk of hemorrhagic conversion resulting from in part, the inability to reverse rTPA activity. Second, the short therapeutic window for rTPA renders more than 90% of stroke patients ineligible for therapy.[2, 3] Finally, rTPA only achieves approximately 30% recanalization and re-occlusion commonly occurs after primary thrombolysis, resulting in loss of initial neurological improvement.

von Willebrand factor (VWF) is a glycoprotein involved in the seminal event of platelet plug formation. VWF interacts with glycoprotein Ib alpha-IX-V complex on the platelet surface to induce platelet adhesion to the vessel wall.[4] Following this glycoprotein IIb/IIIa (gpIIb/IIIa) becomes activated and binds to fibrinogen resulting in thrombus formation. von Willebrand disease (VWD) can be both a qualitative and quantitative reduction and von Willebrand factor. Type I VWD, the predominant form of VWF disease presents with mild bleeding after dental procedures or during menses and not spontaneous hemorrhage.[5] Moreover, VWD Type I patients are protected from cerebrovascular and cardiovascular events.[6] VWF therefore represents an attractive target in arterial thrombosis and may be superior to current therapies.

Aptamers are single-stranded oligonucleotides that have potential advantages over other classes of therapeutic agents. They bind to their target with high affinity and specificity.[7] They can be chemically modified to customize their bioavailability, chemically synthesized in large scale and most pertinent to our application, can be rapidly reversed.[8-11]

In this Example, the inventors demonstrate that aptamer 9.14T79vrt7 inhibits platelet adhesion under high shear stress in a dose-dependent manner and prevents platelet aggregation. It prevents thrombus formation in a murine carotid injury model. It also demonstrates superior thrombolytic activity in both a murine and canine models of arterial occlusion compared to rTPA and did so without inducing intracranial hemorrhage or shedding of embolic clot to the brain. Finally, an antidote oligonucleotide designed against 9.14T79vrt7 reverses the antiplatelet activity of the aptamer within 2 minutes both in human blood and a murine model of bleeding.

The studies in this Example suggest that the 9.14T79vrt7 aptamer represents a novel and potentially safer approach to treat ischemic stroke and other acute thrombotic events.

Materials and Methods

Synthesis of Atamer Truncates, Modifications and Antidote Oligonucleotides (AOs)

Aptamer truncates were either transcribed or synthesized in-house. Briefly, T7 RNA polymerase was used to transcribe RNA aptamer truncates T10, T21, and T22. Aptamer truncates, modifications, and antidotes were synthesized using a MerMade 6/12 Oligonucleotide synthesizer (BioAutomation, Irving, TX). Software predicting RNA secondary structure (Mfold by M. Zuker) was used to predict secondary structure.

RNA Aptamer Preparation and Folding

Prior to platelet function analysis (PFA) and in vivo models, RNA-based aptamers may be "folded" in an appropriate physiological buffer.[13] Aptamer solution is heated to 95° C. for 3 minutes, immediately placed on ice for 3 minutes, and then allowed to come to room temperature over approximately 5 to 10 minutes.

Human Whole Blood Studies

Human blood was collected from healthy volunteers by vena puncture after written informed consent. Blood draws were performed in accordance with protocols that have been approved by the Institutional Review Board from both the Durham Veterans Administration Medical Center and Duke University Medical Center.

Platelet Adhesion Analysis

The Venaflux™ microfluidics system (Cellix, Dublin, Ireland) measures platelet adhesion on a collagen surface. Human blood was collected into hirudin tubes from healthy volunteers by vena puncture. An aliquot containing 300 μl of whole blood treated with aptamer or platelet-binding buffer alone was flowed through collagen-coated micro-channels at 60 dynes for 3 minutes. Channels were then rinsed with saline for 3 minutes to wash away RBC and unbound platelets. Venaflux imaging software and Image Pro Plus were used to image bound platelets and calculate covered surface area. Aptamer was incubated at 95° C. for 3 minutes, placed on ice for 3 minutes, then incubated for 10 minutes at room temperature. After cooling, aptamer was kept on ice until use. Total surface area covered by bound platelets in treated blood was expressed as a percentage of total coverage in negative control blood. Statistical significance was determined by analysis of variance; $IC_{50}$ of the aptamer was calculated using a fitted linear regression curve.

Total Thrombus-formation Analysis System (T-TAS)

The T-TAS (Zacrox, Fujimori Kogyo Co. Ltd., Tokyo, Japan) was used to assess thrombus formation in both human and canine whole blood.[15] Blood was collected in a tube with hirudin in a PL chip that contains 25 capillary channels coated with type 1 collagen. The blood flow across the chip was maintained at a rate of 14 μl/min. Platelet aggregation was measured as a function of the amount of pressure (kPa) needed to maintain the flow rate. A camera was also used to observe platelet activity across the collagen-coated capillary channels.

Murine In Vivo Studies

Investigators that performed surgery or analyzed carotid flow and imaging data were blinded to the treatment groups. All in vivo experiments were approved by the Duke University Institutional Animal Care and Use Committee and The Ohio State University Institutional Animal Care and Use Committee. Moreover, these committees adhere to the NIH Guide for the Care and Use of Laboratory Animals.

Carotid Artery Occlusion and Thrombolysis

Murine carotid artery occlusion studies were performed on male and female 8-week old C57BL/6 mice were obtained from the Jackson Laboratory. Thrombosis/occlusion was achieved using Whatman filter paper soaked in $FeCl_3$. Following 20 minutes of carotid occlusion, treatment was initiated. Male and female 8-week old C57BL/6 mice were obtained from the Jackson Laboratory. Animals were anesthetized with ketamine (55 mg/kg) and xylazine (15 mg/kg). Through a midline ventral incision, the animal was intubated (Harvard Apparatus mouse ventilator, Holliston, MA) and the common carotid artery was isolated. Baseline carotid flow was obtained with a Doppler flow probe (Transonic Systems Inc., Ithaca, NY). Whatman filter paper soaked in 10% ferric chloride was placed on the artery for 3 minutes. Following 20 minutes of carotid occlusion, treatment was initiated. Through an intravenous saphenous infusion (Harvard Apparatus PHD 2000 Infusion Pump, Holliston, MA), animals were treated with control (platelet-binding buffer), VWF aptamer, TPA, aptamer/antidote, TPA/VWF aptamer or no perfusion. Carotid flow was monitored for an additional 90 minutes to assess reperfusion. Heart rate, EKG (ADInstruments PowerLab 4/35 EKG monitoring system, Sydney, Australia) and blood pressure (Kent Scientific CODA Non-Invasive BP Measurement system, Torrington, CT) were monitored throughout the procedure. Histological analysis was performed on the carotid arteries.

Femoral Vein Bleeding

Murine femoral vein bleeding model was performed on male and female 8-week old C57BL/6 mice were obtained from the Jackson Laboratory to assess reversibility of antidote oligonucleotide.[16] Animals were anesthetized with isoflurane. The hair on the ventral side of both hind limbs was removed. They were then placed supine on a temperature and ECG monitoring board. Extremities were gently restrained. The skin on the left and right ventral hind limb was incised exposing a length of the saphenous neurovascular bundle; the bundle was covered with normal saline to prevent drying. The left saphenous vein was cannulated for drug administration. To assess hemostasis, the right saphenous vein was transected by piercing it with a 23-G needle followed by a longitudinal incision made in the distal portion of the vessel. Blood was gently wicked away until hemostasis occurred. The clot was then removed to restart bleeding and the blood was again wicked away until hemostasis occurs again. Clot disruption was repeated after every incidence of hemostasis for 30 minutes. Two parameters were measured: 1) the number of times that hemostasis occurs in a 30-minute period, and 2) the time required for each hemostasis.

Canine Carotid Artery Occlusion and Thrombolysis

Canine carotid artery occlusion studies were performed on male and female adult beagles (7-11 kg). Carotid occlusion was induced with $FeCl_3$ and stabilized for 45 minutes before treatment was initiated. Dogs were anesthetized and intubated. Right femoral arterial and venous catheter was obtained. The right carotid artery was exposed, and baseline carotid flow was obtained using a Doppler flow probe. Thrombosis was induced with a 50%ferric chloride patch for 15 minutes, and the clot was stabilized for 45 minutes. Dogs were then intravenously infused with vehicle, 0.9 mg/kg TPA or 0.5 mg/kg VWF aptamer. The aptamer and vehicle were administered as a bolus while the rTPA was administered by standard clinical protocol of 10% bolus followed by the remaining drug infused over 45 minutes. Carotid flow was monitored for 120 minutes. A flow probe distal to the site of thrombosis monitored blood flow transit time throughout the experiment. Carotid angiography demonstrated baseline patency, thrombotic occlusion, and recanalization. Periodic blood draws assessed platelet inhibition (Platelet Function Analyzer-100). At the conclusion of the experiment, the brain and carotid arteries of each animal were collected and embedded for histological analysis.

Statistical Analysis

Values are expressed as mean±SD Statistical analysis was performed using multiple t-tests, chi-square analysis and two-way ANOVA where appropriate.

Results

Optimized VWF Aptamer 9.14T79 Binds and Inhibits VWF Activity In Vitro and Ex Vivo To create a VWF aptamer that would be amenable for future clinical, we designed and tested a series of VWF aptamer derivatives derived from the 2'Fluoro-pyrimidine modified RNA aptamer VWF9.14.[12, 13] See Example 1. This effort resulted in a lead VWF aptamer, T59, which is 30 nucleotides long that retained high affinity binding and inhibitory activity. Next, to improve nuclease resistance and optimize the composition, we systematically substituted 2' O-methyl and/or 2' Fluoro moieties into the T25 and T59 aptamer truncates. Almost 90 truncates were synthesized and tested in vitro. The fully optimized aptamer 9.14T79vrt7 is 35-nucleotides and binds to VWF with a dissociation constant ($K_d$)=11.2 nmol/L, $B_{max}$=56% compared to the 60-mer $K_d$=18.4 nmol/L, $B_{max}$=51%(See Tables 1 and 2 above and FIGS. 1-3).

Figure 20:
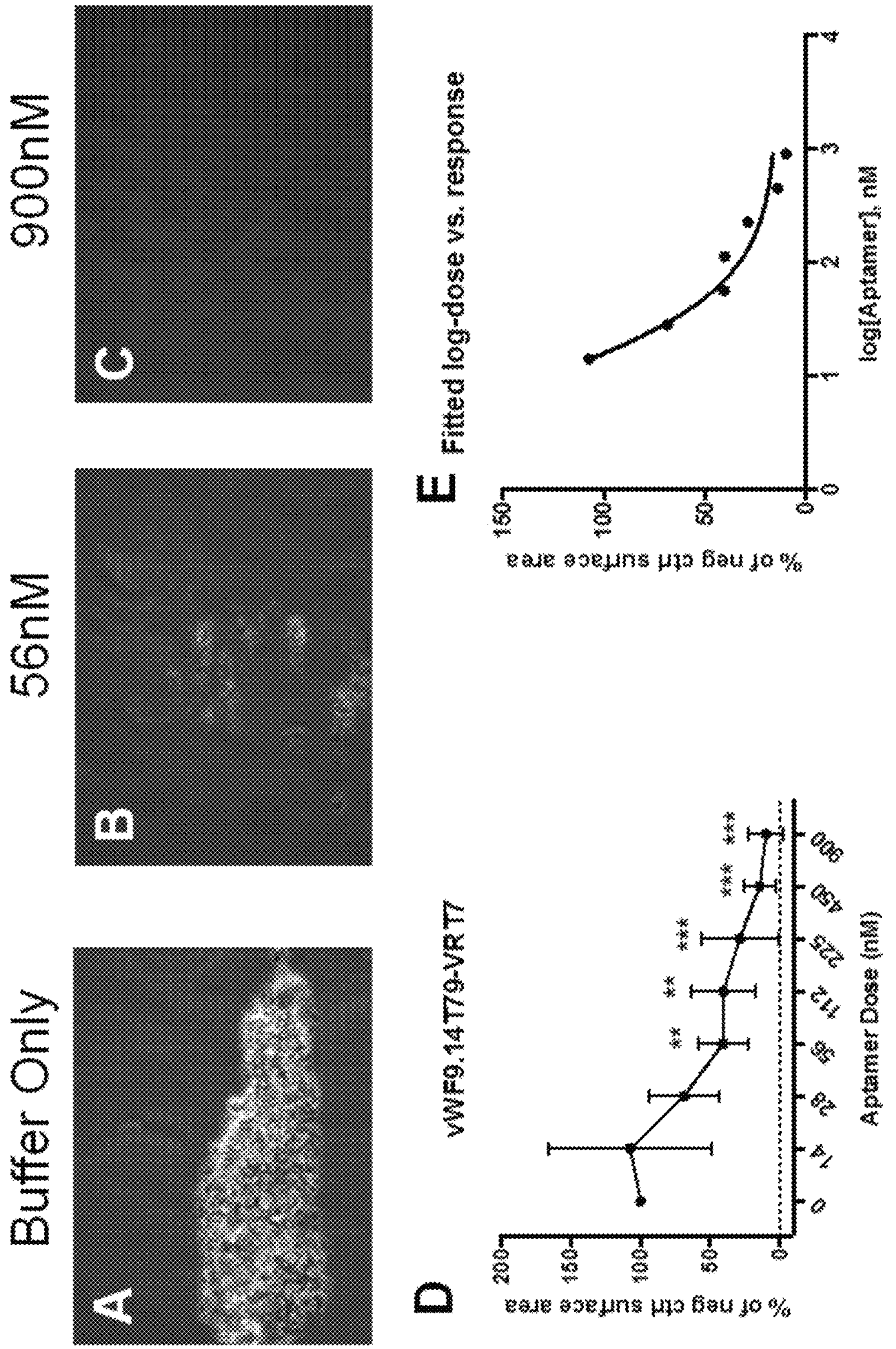
FIGS. 20A-20E show aptamer 9.14T79vrt7 (SEQ ID NO: 7) inhibits platelet adhesion under high shear, inhibits platelet aggregation in whole blood and prevents thrombosis in vivo. The aptamer prevented human platelet adhesion in a dose-dependent manner.
Figure 21:
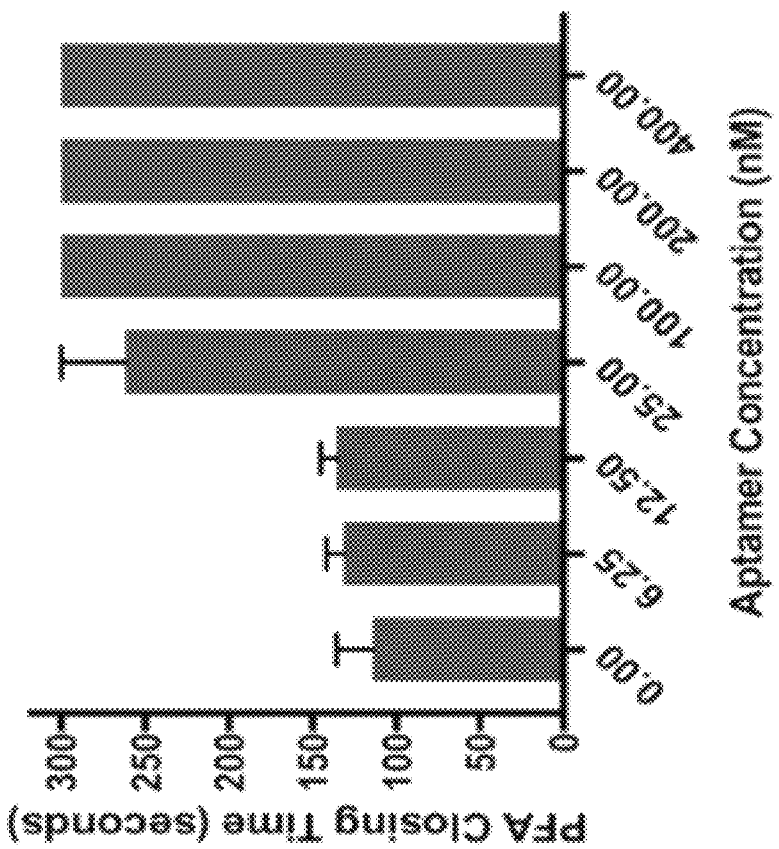
FIG. 21 is a graph showing PFA-100 results demonstrating that T79vrt7 (SEQ ID NO: 7) completely inhibits platelet aggregation. Doses between 100-400 nmol/L exceeded the upper limit of the assay and 25 nM demonstrated significant platelet aggregation compared to control (n=4 per group) ($p<0.01$).
Figure 22:
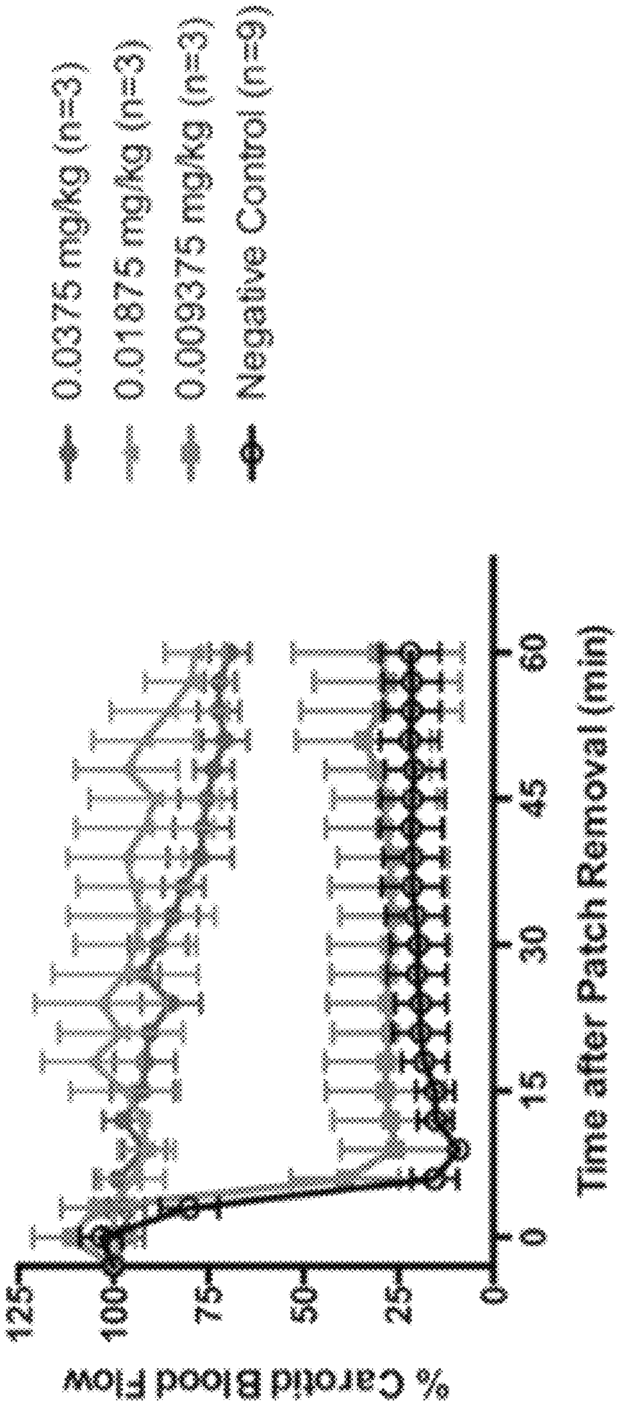
FIG. 22 is a graph showing murine carotid artery thrombosis, dose range 0.009375 mg/kg –3 mg/kg., 9.14T79vrt7 (SEQ ID NO: 7)-treated mice demonstrated that at dose as low as 0.0185 mg/kg, there was patency of the carotid artery compared to negative control (n=3 per group). Doses over 0.0375 mg/kg not shown for clarity, but all demonstrate vessel patency.

To evaluate the inhibitory effect of the aptamer on platelet adhesion, human whole blood samples were treated with aptamer starting at 900 nmol/L with 2-fold dilutions to 14 nmol/L and tested by measuring platelet adhesion under high-shear stress. The aptamer prevented platelet adhesion to the collagen surface in a dose-dependent manner (FIG. 20-22). Near complete inhibition of platelet adhesion was achieved at doses from 225 to 900 nmol/L (FIGS. 20C and 20D) and intermediate inhibition at doses from 56 to 112 nmol/L (FIGS. 20B and 20D). Log-dose versus response data fitting resulted in a $logIC_{50}$ calculation of 1.9 (72.6 nmol/L) (FIG. 20E).

The aptamer's effect on platelet aggregation was measured ex vivo in a PFA-100 human whole blood assay. The VWF aptamer completely inhibited platelet aggregation in this system at doses over 100 nmol/L, where platelet plug formation and closing time exceeded 300 seconds, representing the upper limit of the assay (FIG. 21). Thus VWF aptamer 9.14T79vrt7 prevents both platelet adhesion and aggregation ex vivo.

9.14T79 Demonstrates Increased Thrombolysis in a Murine Model of Carotid Occlusion than Recombinant Tissue Plasminogen Activator (rTPA)

A murine model of carotid artery occlusion was next used to evaluate aptamer thrombolytic activity. After 20 minutes of stable carotid artery occlusion, animals received aptamer 9.14T79, saline control or rTPA. The dose of rTPA used in this experiment was 10 mg/kg, 11-fold higher than 0.9 mg/kg (the dose used to treat humans who present with ischemic strokes within 3-4.5 hours of last known well) because this was the dose reported to be effective for recanalization in murine models of arterial thrombosis.[17] The aptamer was dosed at 0.5 mg/kg and as shown in FIG. 23A demonstrated significantly higher recanalization compared to rTPA ($p<0.05$) and buffer control (n=8 per group) ($p<0.01$). Histological analysis of the carotid arteries from each group grossly correlated with the degree of recanalization measured by the flow probe (FIGS. 23B, 23C, and 23D). Examination of the cross-sections of the affected carotid artery of the buffer-control group demonstrated complete occlusion of all animals tested (n=8) (FIG. 23D). Vessel sections from the rTPA-treated mice, showed nearly complete thrombosis and occlusion of the carotid (n=8) (FIG. 23C). Finally, the histology of the carotid artery section of the VWF aptamer-treated mice demonstrated complete patency in 6 of the samples and only evidence of small clot in a section of two of the previously occluded vessels (n=8) (p=0.01) (FIG. 23B).

9.14T79vrt7 Demonstrates Dose-Dependent Platelet Inhibition of Canine Whole Blood In order to evaluate platelet thrombus formation under high shear, and begin to assess the aptamer in a large animal model, we tested the VWF aptamer in a Total Thrombus-formation Analysis System (T-TAS) (Fujimori Kogyo Co., Yokohama, Japan)[18]. 9.14T79vrt7 inhibited canine platelet aggregation and maintained blood flow pressure at doses between 18.75-100 nmol/L (FIG. 24A) (n=5 per group) ($p<0.05$ compared to buffer control). At a dose of 100 nmol/L, there was complete inhibition of platelet adhesion and aggregation (FIG. 24B). Each picture represents the first 10 seconds of minutes 1 through 5. The areas of white haze seen from minutes 3-5 in the buffer control panel are platelets adhering to the horizontal capillary channel.

The aptamer panel shows no such platelet accumulation indicating that 9.14T79vrt7 is potent inhibitor of canine platelet function under sheer stress in vitro.

9.14T79vrt7 Demonstrates Recanalization in a Canine Model of Carotid Occlusion

A canine model of cerebrovascular thrombotic disease was used to corroborate the murine results in a large, clinically relevant animal. Arterial occlusion established and persistent for 45 minutes before treatment. Animals received an intravenous injection of 0.5 mg/kg of 9.14T79vrt7 as a bolus or 0.9 mg/kg of rTPA by the standard clinical protocol of 10% injection followed by the remaining 90% infused over 45 minutes. The carotid arteries of all 3 dogs that received 9.14T79vrt7 recanalized between 5 and 15 minutes after administration (FIGS. 24F, 24G, respectively). By contrast animals treated with rTPA or saline control demonstrated no recanalization after treatment (n=3 per group).

Figures 24C, 24D, 24E, 24H, 24K:
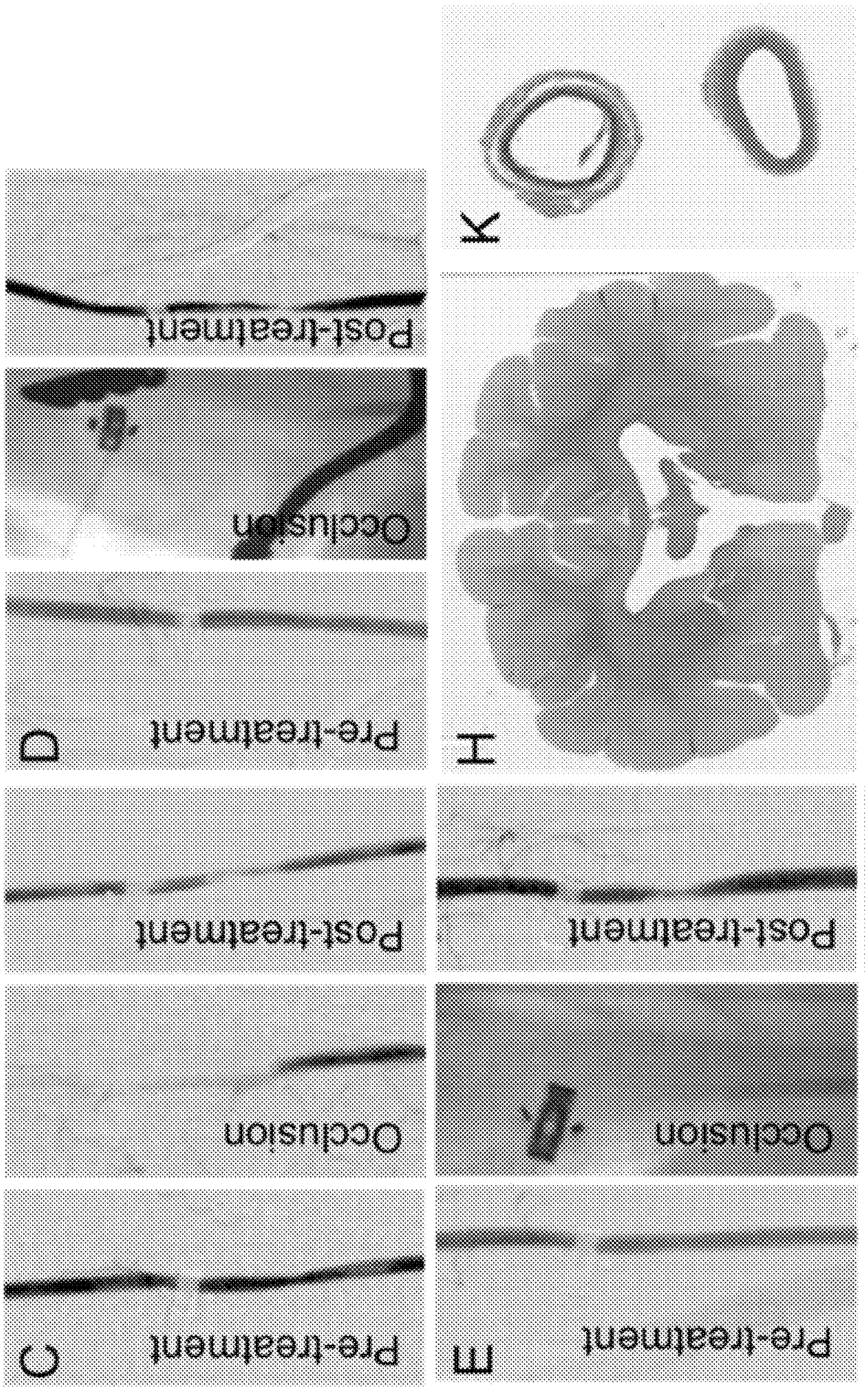
Figures 24F, 24G, 24I, 24J, 24L, 24M:
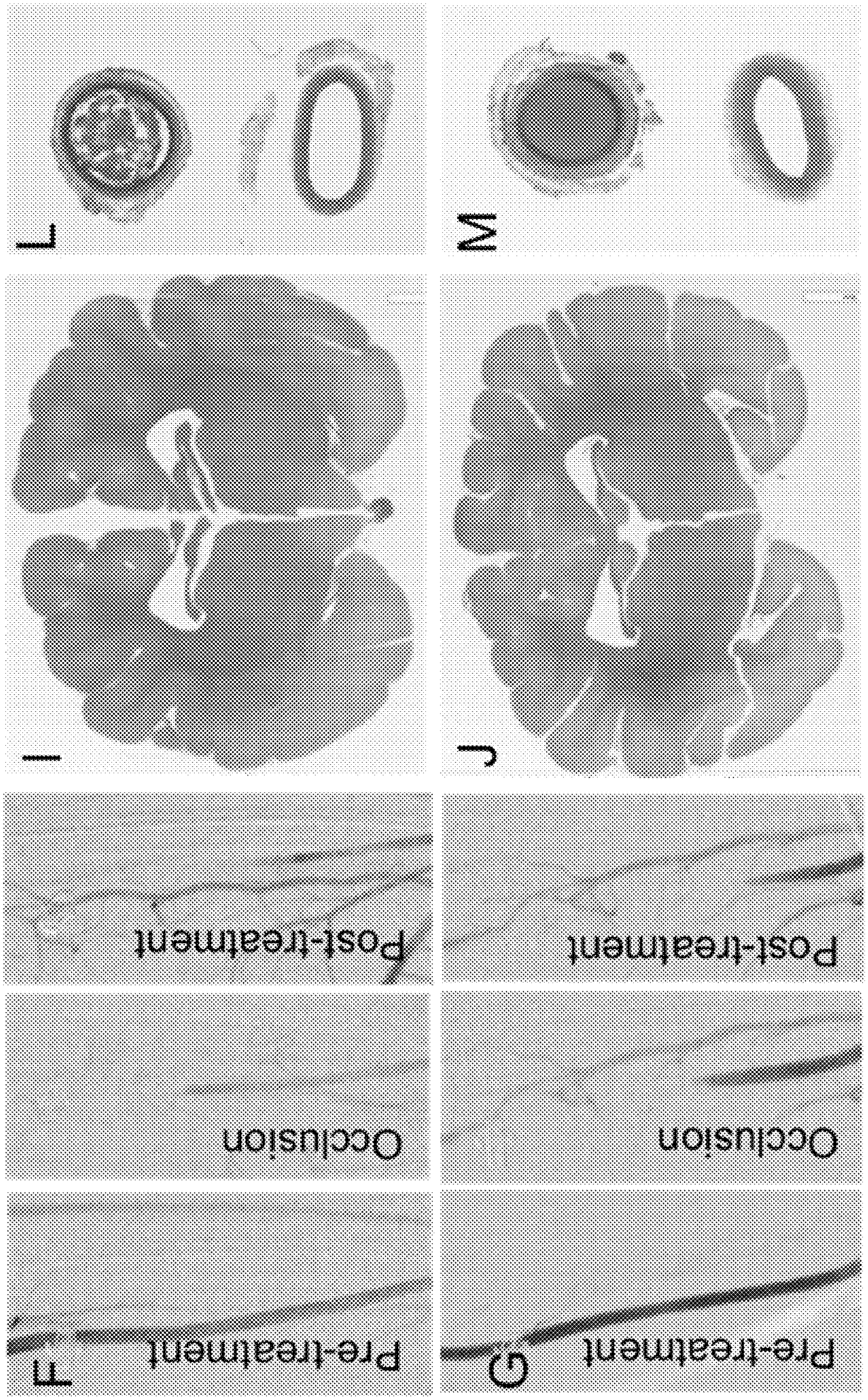

To investigate the safety of 9.14T79vrt7, we evaluated bleeding and clotting in the brain of these dogs. 9.14T79vrt7 did not induce intracranial hemorrhage nor did carotid artery recanalization result in cerebral thromboemboli in any of the 3 animals (FIG. 24H-J). Brain histology from both the 9.14T79vrt7 and rTPA group is identical to the control saline-treated group. The lack of cerebral thromboembolism in the aptamer group was reassuring as the carotid artery histology demonstrated essentially complete recanalization of the vessel (FIG. 24K). The top carotid section is through the area of vessel damage where occlusion occurred while the bottom section is from the patent portion adjacent to the diagnostic catheter. By sharp contrast, both the rTPA and saline-treated control group of animals contained thrombi that continued to occlude the damaged carotids consistent with the inability of these approaches to restore blood flow (FIG.

An antidote oligonucleotide Can Rapidly Reverse the Antiplatelet Activity of 9.14T79vrt7 In Vitro and In Vivo We created an antidote oligonucleotide (AO, also called VWF9.14T79- AO2 or AO55) to reverse 9.14T79vrt7 activity if needed. None of the antidotes initially tested could reverse the 30-nucleotide aptamer T59 likely because they could not access a good nucleation site on the aptamer once it was tightly bound to VWF. Therefore, we added a 5-nucleotide Uracil (oligo-U tail) to the 3'-end of the molecule as an artificial nucleation site and tested a 16-nucleotide antidote complementary to this tail and the 3' end of the aptamer. The antidote oligonucleotide (AO) reversed the aptamer's antiplatelet activity in vitro within 2 minutes at a ratio as low as of 2:1 over 9.14T79vrt7 (FIG. 14) (n=2 per group).

Figure 25:
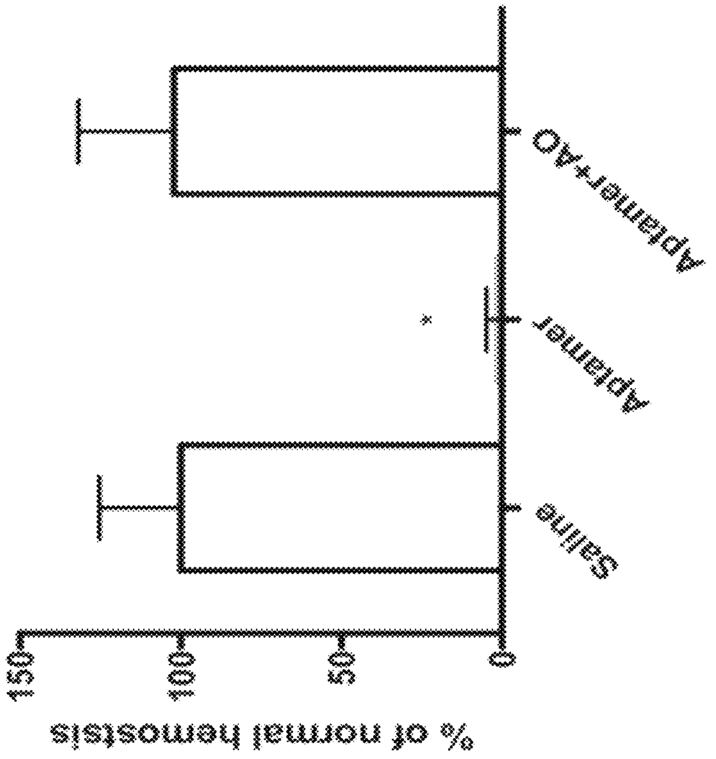
FIG. 25 shows an antidote oligonucleotide reverses 9.14T79vrt7/DTRI-031 (SEQ ID NO: 7) ex vivo and in a murine femoral vein bleeding model. The graph is represented as a % of normal hemostasis in a mouse without any treatment. The untreated control group (not shown) was similar to the saline-treated group of (n=7 per group). 9.14T79 administered at 0.375 mg/kg demonstrated no clot disruptions (n=11) compared to the control and control and saline-treated groups ($p<0.0001$). Adding antidote 5 minutes after aptamer administration and measuring clot disruption 2 minutes later revealed complete reversal of bleeding similar to animals that never received the aptamer (n=7). AO administered alone did not result in increased thrombosis compared to negative control (data not shown) (*=statistical significance).

The ability of the antidote to reverse the antiplatelet aptamer was evaluated in a murine femoral vein bleeding model.[16] The control untreated mice group demonstrated 12±3 disruptions, (n=7) which were similar to the saline group of 17±3 disruptions (n=7) (p>0.05). 9.14T79vrt7 administered at a dose of 0.375 mg/kg resulted in no clot disruptions, which was highly significant compared to untreated control and saline treated animals (n=11) (p<0.0001). 9.14T79vrt7 administration followed by antidote oligonucleotide addition demonstrated 16±9 disruptions, which was similar to animals that never received the aptamer (n=7). This data was expressed as a % of normal thrombosis (FIG. 25). Administration of antidote alone did not result in an increased or decreased clot disruption (data not shown). Thus, the antidote can rapidly reverse any bleeding associated with aptamer-mediated inhibition of VWF.

Discussion

Currently, there are no acute treatment options for the vast majority of ischemic stroke patients. rTPA treatment, results in hemorrhage, it time-limited and cannot be reversed. Our research demonstrates that an antidote-controlled VWF inhibitor may provide a robust yet safe treatment option for these patients. 9.14T79vrt7 demonstrated improved binding affinity compared to the full-length aptamer,[12] commensurate with the potency of a monoclonal antibody.[7, 19] Aptamer 9.14T79vrt7 prevented adhesion of human platelets to a collagen surface (FIG. 20-22) as well as under high sheer stress (FIG. 24).

In vivo, 9.14T79vrt7 maintained arterial patency and maintain a transit time greater than 75% at a dose as low as 0.0188 mg/kg (FIG. 22). In comparison to both negative control and intravenous rTPA, 9.14T79vrt7 demonstrated superior thrombolytic activity in a murine model of carotid occlusion (FIG. 23). The dose of IV rTPA used is 10-fold higher than is used clinically largely because that is the dose required to achieve thrombolysis in mice.[17] Sixty minutes after drug administration, the rTPA group achieved 25% transit time of pre-injury flow compared to 75% for the aptamer-treated group. This effect persisted greater than 100 minutes after drug administration. The aptamer was infused over 5 minutes while the rTPA was infused over 45 minutes due to the risk of hemorrhage associated with rTPA.

At first glance, the idea of a drug that targets an endothelial and platelet factor breaking up a formed arterial thrombus is not intuitive, however, a growing body of literature supports the "disaggregation" activity of VWF inhibitors. An in vitro study, high fluid shear stress and irregular vessel surface showed that VWF collates into thick bundles and meshes that span the vessel lumen, binding platelets together, resulting in arterial occlusion.[20] Anti-VWF therapy could therefore have an impact on arterial occlusion. This hypothesis is supported by our observation that even in major arteries in dogs, VWF aptamer 9.14T79vrt7 can engender recanalization of an occluded vessel (FIG. 24).

Figure 14:
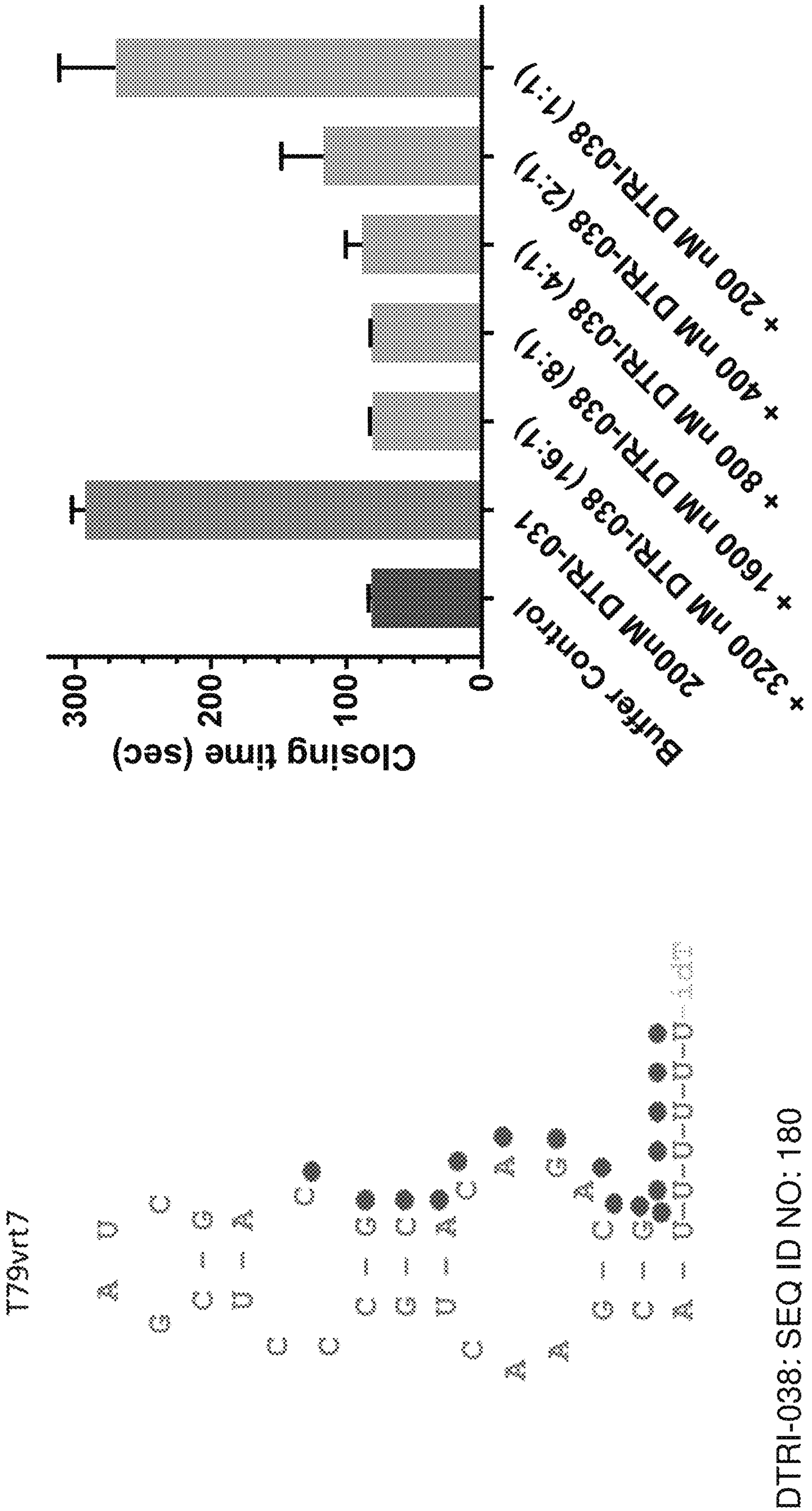
FIG. 14 shows the predicted secondary structure and PFA data for VWF9.14T79vrt7 (DTRI-031; SEQID NO: 7) without or with varying molar ratios of the antidote DTRI-038 (SEQ ID NO: 180).

The main class of parenteral anti-platelet agents used clinically is glycoprotein IIb/IIIa (gpIIb/IIIa) inhibitors (Abciximab, Eptifibatide and Tirofiban). These agents significantly improved outcomes in acute coronary syndromes (ACS) and percutaneous coronary interventions (PCI).[21] When tested in acute ischemic stroke however, they resulted in significant increase in intracranial hemorrhage without improvement in morbidity or mortality.[22] Therefore, we developed an antidote oligonucleotide that can readily reverse VWF aptamer activity in case of hemorrhage. The antidote completely reversed 9.14T79vrt7 activity at a molar ratio of aptamer to antidote as low as 1:2 (FIG. 14). Durable reversal of aptamer was demonstrated in vivo in a venous model of bleeding (FIGS. 9A and 9B).[13, 16] At a dose of 0.375 mg/kg of aptamer, no clotting occurred; however administration of ten-fold molar excess of antidote oligonucleotide reversed the aptamer and restored normal hemostasis. The ability to completely and rapidly reverse such a potent antiplatelet agent by a matched antidote agent represents a significant step forward in developing safer potent parenteral anti-platelet drugs to treat thrombosis and particularly acute ischemic stroke.

REFERENCES

1. Adams H P, Jr. Stroke: a vascular pathology with inadequate management. *J Hypertens Suppl.* 2003;21: S3-7.
2. Tissue Plasminogen Activator for Acute Ischemic Stroke. *New England Journal of Medicine.* 1995;333: 1581-1588.
3. Lansberg M G, Bluhmki E and Thijs V N. Efficacy and safety of tissue plasminogen activator 3 to 4.5 hours after acute ischemic stroke: a metaanalysis. *Stroke.* 2009;40:2438-41.
4. Hoffman M and Monroe D M, 3rd. A cell-based model of hemostasis. *Thrombosis and haemostasis.* 2001;85: 958-65.
5. Leebeek F W and Eikenboom J C. Von Willebrand's Disease. *The New England journal of medicine.* 2016; 375:2067-2080.
6. Sanders Y V, Eikenboom J, de Wee E M, van der Bom J G, Cnossen M H, Degenaar-Dujardin M E, Fijnvandraat K, Kamphuisen P W, Laros-van Gorkom B A, Meijer K, Mauser-Bunschoten E P, Leebeek F W and Wi N S G. Reduced prevalence of arterial thrombosis in von Willebrand disease. *Journal of thrombosis and haemostasis: JTH.* 2013; 11:845-54.
7. Nimjee S M, Rusconi C P and Sullenger B A. Aptamers: an emerging class of therapeutics. *Annual review of medicine.* 2005;56:555-83.

8. Nimjee S M, Rusconi C P, Harrington R A and Sullenger B A. The potential of aptamers as anticoagulants. *Trends in cardiovascular medicine.* 2005; 15:41-5.
9. Nimjee S M, Oney S, Volovyk Z, Bompiani K M, Long S B, Hoffman M and Sullenger B A. Synergistic effect of aptamers that inhibit exosites 1 and 2 on thrombin. *Rna.* 2009; 15:2105-11.
10. Rusconi C P, Roberts J D, Pitoc G A, Nimjee S M, White R R, Quick G, Jr., Scardino E, Fay W P and Sullenger B A. Antidote-mediated control of an anticoagulant aptamer in vivo. *Nature biotechnology.* 2004; 22:1423-8.
11. Rusconi C P, Scardino E, Layzer J, Pitoc G A, Ortel T L, Monroe D and Sullenger B A. RNA aptamers as reversible antagonists of coagulation factor IXa. *Nature.* 2002;419:90-4.
12. Oney S, Nimjee S M, Layzer J, Que-Gewirth N, Ginsburg D, Becker R C, Arepally G and Sullenger B A. Antidote-controlled platelet inhibition targeting von Willebrand factor with aptamers. *Oligonucleotides.* 2007; 17:265-74.
13. Nimjee S M, Lohrmann J D, Wang H, Snyder D J, Cummings T J, Becker R C, Oney S and Sullenger B A. Rapidly regulating platelet activity in vivo with an antidote controlled platelet inhibitor. *Molecular therapy: the journal of the American Society of Gene Therapy.* 2012;20:391-7.
14. Ortel T L, James A H, Thames E H, Moore K D and Greenberg C S. Assessment of primary hemostasis by PFA-100 analysis in a tertiary care center. *Thrombosis and haemostasis.* 2000;84:93-7.
15. Daidone V, Barbon G, Cattini M G, Pontara E, Romualdi C, Di Pasquale I, Hosokawa K and Casonato A. Usefulness of the Total Thrombus-Formation Analysis System (T-TAS) in the diagnosis and characterization of von Willebrand disease. *Haemophilia: the official journal of the World Federation of Hemophilia.* 2016;22:949-956.
16. Monroe D M and Hoffman M. A mouse bleeding model to study oral anticoagulants. *Thrombosis research.* 2014;133 Suppl 1:S6-8.
17. Orset C, Macrez R, Young A R, Panthou D, Angles-Cano E, Maubert E, Agin V and Vivien D. Mouse model of in situ thromboembolic stroke and reperfusion. *Stroke.* 2007;38:2771-8.
18. Yamaguchi Y, Moriki T, Igari A, Matsubara Y, Ohnishi T, Hosokawa K and Murata M. Studies of a microchip flow-chamber system to characterize whole blood thrombogenicity in healthy individuals. *Thrombosis research.* 2013; 132:263-70.
19. Nimjee S M, White R R, Becker R C and Sullenger B A. Aptamers as Therapeutics. *Annual review of pharmacology and toxicology.* 2017;57:61-79.
20. Zheng Y, Chen J and Lopez J A. Flow-driven assembly of VWF fibres and webs in in vitro microvessels. *Nature communications.* 2015;6:7858.
21. Topol E J. Novel antithrombotic approaches to coronary artery disease. *The American journal of cardiology.* 1995;75:27B-33B.
22. Ciccone A, Motto C, Abraha I, Cozzolino F and Santilli I. Glycoprotein IIb-IIIa inhibitors for acute ischaemic stroke. *The Cochrane database of systematic reviews.* 2014;3:CD005208.
23. Markus H S, McCollum C, Imray C, Goulder M A, Gilbert J and King A. The von Willebrand inhibitor ARC1779 reduces cerebral embolization after carotid endarterectomy: a randomized trial. *Stroke.* 2011;42: 2149-53.
24. Diaz J A, Wrobleski S K, Alvarado C M, Hawley A E, Doornbos N K, Lester P A, Lowe S E, Gabriel J E, Roelofs K J, Henke P K, Schaub R G, Wakefield T W and Myers D D, Jr. P-selectin inhibition therapeutically promotes thrombus resolution and prevents vein wall fibrosis better than enoxaparin and an inhibitor to von Willebrand factor. *Arteriosclerosis, thrombosis, and vascular biology.* 2015;35:829-37.

We claim:

1. A method for treating a blood clot in a subject comprising administering to the subject a VWF-targeting aptamer in a therapeutically effective amount to reduce the blood clot in the subject, wherein the VWF-targeting aptamer comprises a polynucleotide comprising from 5' to 3' (a) a polynucleotide having at least 70% sequence identity to SEQ ID NO: 1 comprising a first stem forming region comprising 3 nucleotides, a first loop region comprising the nucleotide sequence AAC, a second stem forming region comprising 3 nucleotides, a second loop region comprising the nucleotide sequence CC and a third stem forming region consisting of 2-8 nucleotides, (b) a third loop region consisting of 1-12 nucleotides or a spacer sequence, and (c) a polynucleotide having at least 70% sequence identity to SEQ ID NO: 2 comprising a fourth stem forming region consisting of 2-8 nucleotides and forming a stem with the third stem forming region, a fourth loop region comprising the nucleotide C, a fifth stem forming region comprising 3 nucleotides and forming a stem with the second stem forming region, a fifth loop region comprising the nucleotide sequence CAGA, and a sixth stem forming region comprising 3 nucleotides and forming a stem with the first stem forming region, wherein the polynucleotide comprises an unmodified form or comprises a modified form comprising at least one nucleotide base modification, and wherein the aptamer is no more than 53 nucleotides in length.

2. The method of claim 1, wherein the subject suffers a Deep Vein Thrombosis, a stroke, a heart attack, or a pulmonary embolism.

3. The method of claim 1, further comprising administering to the subject an antidote in a therapeutically effective amount to neutralize the VWF-targeting aptamer.

4. The method of claim 3, wherein the antidote comprises a polynucleotide having at least 90% sequence identity to SEQ ID NO: 157, wherein the antidote is no more than 24 nucleotides in length.

5. The method of claim 1, wherein the subject is a mammal.

6. The method of claim 5, wherein the mammal is a human.

7. The method of claim 1, wherein the aptamer comprises from 5' to 3' SEQ ID NO: 1, a variable nucleotide sequence consisting of 1 12 nucleotides and SEQ ID NO: 2.

8. The method of claim 1, wherein the aptamer comprises a polynucleotide having at least 90% sequence identity to any one of SEQ ID NOS: or 4.

9. The method of claim 1, wherein the dissociation constant ($K_D$) of the aptamer for the human VWF protein is less than 100 nanomolar (nM).

10. The method of claim 1, wherein the aptamer comprises a tail nucleotide sequence at the 5' end or the 3' end of the polynucleotide which is not capable of base pairing with 3 or more consecutive nucleotides in the polynucleotide, wherein the tail nucleotide sequence consists of 2-12 nucleotides.

11. The method of claim 10, wherein the tail nucleotide sequence is at the 3' end of the polynucleotide and consists of the nucleotide sequence (U/T) (U/T) (U/T) (U/T) (U/T).

12. The method of claim 1, wherein the aptamer is no more than 39 nucleotides in length.

13. The method of claim 1, wherein the aptamer comprises an RNA polynucleotide.

14. The method of claim 1, wherein the aptamer comprises at least one nucleotide base modification selected from the group consisting of a 2'fluoro modification, a 2'O-methyl modification, a 5' modification, and a 3'modification.

15. The method of claim 14, wherein the aptamer comprises SEQ ID NO: 7, SEQ ID NO: 8, or SEQ ID NO: 9.

16. The method of claim 14, wherein the 5' modification and/or the 3' modification comprise a 5' linker and/or a 3' linker.

17. The method of claim 1, wherein the aptamer further comprises a stability agent.

18. The method of claim 1, wherein the VWF-aptamer is SEQ ID NO: 7.

19. The method of claim 3, wherein the antidote comprises a sequence reverse complementary to and capable of hybridizing to at least 8 nucleotides of an aptamer comprising a polynucleotide of SEQ ID NO: 3, or a polynucleotide with at least 90% sequence identity to SEQ ID NO: 3 and wherein the antidote is not more than 24 nucleotides in length.

20. The method of claim 3, wherein the antidote is SEQ ID NO: 157.

* * * * *